United States Patent
McEwen

(10) Patent No.: US 11,999,992 B2
(45) Date of Patent: Jun. 4, 2024

(54) NUCLEIC ACID STABILIZATION REAGENT, KITS, AND METHODS OF USE THEREOF

(71) Applicant: Berkeley Lights, Inc., Emeryville, CA (US)

(72) Inventor: Jason M. McEwen, El Cerrito, CA (US)

(73) Assignee: Bruker Cellular Analysis, Inc., Emeryville, CA (US)

( * ) Notice: Subject to any disclaimer, the term of this patent is extended or adjusted under 35 U.S.C. 154(b) by 19 days.

(21) Appl. No.: 16/130,634

(22) Filed: Sep. 13, 2018

(65) Prior Publication Data

US 2019/0085375 A1 Mar. 21, 2019

Related U.S. Application Data

(63) Continuation of application No. PCT/US2017/025065, filed on Mar. 30, 2017.

(60) Provisional application No. 62/316,514, filed on Mar. 31, 2016.

(51) Int. Cl.
| | |
|---|---|
| *C12Q 1/6806* | (2018.01) |
| *B01L 3/00* | (2006.01) |
| *C12N 5/0781* | (2010.01) |
| *C12N 5/0783* | (2010.01) |
| *C12N 5/0786* | (2010.01) |
| *C12Q 1/686* | (2018.01) |

(52) U.S. Cl.
CPC .......... *C12Q 1/6806* (2013.01); *B01L 3/5027* (2013.01); *C12N 5/0635* (2013.01); *C12N 5/0636* (2013.01); *C12N 5/0645* (2013.01); *C12N 5/0646* (2013.01); *C12Q 1/686* (2013.01)

(58) Field of Classification Search
None
See application file for complete search history.

(56) References Cited

U.S. PATENT DOCUMENTS

| | | | |
|---|---|---|---|
| 6,204,375 B1 | 3/2001 | Lader | |
| 2002/0197637 A1 | 12/2002 | Willson et al. | |
| 2005/0170373 A1* | 8/2005 | Monforte | C12Q 1/6809 435/6.14 |
| 2005/0267023 A1 | 12/2005 | Sinclair et al. | |
| 2012/0184725 A1 | 7/2012 | Forman et al. | |
| 2012/0225936 A1 | 9/2012 | Steward et al. | |
| 2013/0059380 A1* | 3/2013 | Ho | A01N 1/021 435/374 |
| 2013/0260369 A1* | 10/2013 | Fischer | C12Q 2523/308 435/5 |
| 2015/0166326 A1 | 6/2015 | Chapman et al. | |
| 2018/0334703 A1 | 11/2018 | Feng et al. | |

FOREIGN PATENT DOCUMENTS

| | | |
|---|---|---|
| CN | 1503910 A | 6/2004 |
| CN | 101360822 A | 2/2009 |
| CN | 105121643 A | 12/2015 |
| CN | 105158455 A | 12/2015 |
| EP | 1658140 B1 | 6/2013 |
| JP | 2002541767 A | 12/2002 |
| JP | 2003513733 A | 4/2003 |
| JP | 2007506403 A | 3/2007 |
| JP | 2011500092 A | 1/2011 |
| JP | 2011512871 A | 4/2011 |
| JP | 2013510127 A | 3/2013 |
| JP | 2015180657 A | 10/2015 |
| JP | 7019590 B2 | 2/2022 |
| WO | 0039314 A1 | 7/2000 |
| WO | 2002033129 A2 | 4/2002 |
| WO | 2002056030 A2 | 7/2002 |
| WO | 2001035819 A9 | 11/2002 |
| WO | 2005005044 A1 | 1/2005 |
| WO | 2007075253 A2 | 7/2007 |
| WO | 2009055732 A1 | 4/2009 |
| WO | 2009114185 A2 | 9/2009 |
| WO | 2012024658 A3 | 5/2012 |
| WO | 2014122629 A2 | 8/2014 |
| WO | 2014146782 A1 | 9/2014 |
| WO | 2015002729 A2 | 1/2015 |
| WO | 2015061497 A1 | 4/2015 |
| WO | 2015155230 A1 | 10/2015 |
| WO | 2015188171 A1 | 12/2015 |
| WO | 2015191633 A1 | 12/2015 |
| WO | 2016011798 A1 | 1/2016 |
| WO | 2017173105 A1 | 10/2017 |

OTHER PUBLICATIONS

Chan, J. et al., "Eukaryotic protein synthesis inhibitors identified by comparison of cytotoxicity profiles", RNA 10:528-543 (2004).
Cox, M. et al., "Assessment of Fixatives, Fixation, and Tissue Processing on Morphology and RNA Integrity", Exp. & Molec. Pathol. 80:183-191 (2006).
Entner, N. et al., "Inhibition of Protein Synthesis: A Mechanism of Amebicide Actionof Emetine and Other Structurally Related Compounds", J. Protozool. 20(1):160-163 (1973).
Grollman, A.,"Effects of Emetine on Protein and Nucleic Acid Biosynthesis in HeLa Cells", J. Biol. Chem. 243(15):4089-94 (1968).
Harvey, J. et al., "Dual actions of the metabolic inhibitor, sodium azide on KATPchannel currents in the rat CRI-G1 insulinoma cell line", Brit. J. Pharmacol. 126:51-60 (1999).
McKeehan, W. et al., "The Mechanism of Cycloheximide Inhibition of Protein Synthesis in Rabbit Reticulocytes", Biochem. Biophys. Res. Comm. 36(4):625-30 (1969).

(Continued)

*Primary Examiner* — Samuel C Woolwine
*Assistant Examiner* — Carolyn L Greene
(74) *Attorney, Agent, or Firm* — McNeill Baur PLLC

(57) ABSTRACT

Reagents for stabilizing the nucleic acids of a biological cell, compositions, kits and methods of use thereof are described. The stabilization reagents may prepare the nucleic acids within the biological cell for storage and preserve the representative population of the nucleic acids for later isolation and analysis.

21 Claims, 16 Drawing Sheets

(56) References Cited

OTHER PUBLICATIONS

Tsubaki, M. et al., "Fourier-Transform Infrared Study of Azide Binding to the Fe(a3)—Cu(B) Binuclear Site of Bovine Heart Cytochrome c Oxidase: New Evidence for a Redox-Linked Conformational Change at the Binuclear Site", Biochem. 32:174-182 (1993).
European Patent Office, Extended European Search Report for Application No. 17776666.4, dated Nov. 8, 2019.
Bowler et al., How azide inhibits ATP hydrolysis by the F-ATPases, PNAS 103(23): 8646-8649 (2006).
Vispe et al., Triptolide is an inhibitor of RNA polymerase I and II-dependent transcription leading predominantly to down-regulation of short-lived mRNA, Mol Cancer Ther 8(10): 2780-2790 (2009).
Wang et al., Triptolide (TPL) Inhibits Global Transcription by Inducing Proteasome-Dependent Degradation of RNA Polymerase II (Pol II), PLoS ONE 6(9): 1-7 (2011).
International Search Report and Written Opinion for PCT Application Serial No. PCT/2017/025065 (Jun. 28, 2017), 8 pages.
Schneider-Poetsch et al., Inhibition of Eukaryotic Translation Elongation by Cycloheximide and Lactimidomycin, Nat Chem Biol., 6(3): 209-217 (2010).
Zhang et al, "Rapid Changes in the Translatome during the Conversion of Growth Cones to Synaptic Terminals," Cell Reports, 2016, 14:1258-1271.
Machine translation of CN105158455, Dec. 16, 2015, 15 pages.
Bensaude, "Inhibiting eukaryotic transcription: Which compound to choose? How to evaluate its activity?," Transcription, 2011, 2(3):103-108.
Grollman, "Structural Basis for Inhibition of Protein Synthesis by Emetine and Cycloheximide Based on an Analogy Between Ipecac Alkaloids and Glutarimide Antibiotics," PNAS, 1966, 56(6):1867-1874.
Ross, J., "A hypothesis to explain why translation inhibitors stabilize mRNAs in mammalian cells: mRNA stability and mitosis", Bioessays, 1997, 19(6):527-9.
Office Action in Japanese Patent Application No. 2022-014717, dated Jul. 12, 2023, 3 pages.

* cited by examiner

FIG. 6

| Ct1-2 | In3-2 | 0.995 |
|---|---|---|
| Ct1-2 | Ct3-2 | 0.996 |
| Ct1-2 | Ct2-2 | 0.998 |
| Ct1-2 | In2-2 | 0.992 |
| Ct1-2 | In1-2 | 0.992 |
| Ct2-2 | In2-2 | 0.993 |
| Ct2-2 | Ct3-2 | 0.998 |
| Ct2-2 | In1-2 | 0.993 |
| Ct2-2 | In3-2 | 0.995 |
| Ct3-2 | In3-2 | 0.996 |
| Ct3-2 | In1-2 | 0.993 |
| Ct3-2 | In2-2 | 0.993 |
| In1-2 | In2-2 | 0.996 |
| In1-2 | In3-2 | 0.996 |
| In2-2 | In3-2 | 0.996 |

*FIG. 7*

| Ct1-2 | NA2-2 | 0.99510879 |
|---|---|---|
| Ct1-2 | Ct2-2 | 0.9975867 |
| Ct1-2 | NA3-2 | 0.99489313 |
| Ct1-2 | NA1-2 | 0.99603307 |
| Ct1-2 | Ct3-2 | 0.99619579 |
| Ct2-2 | NA2-2 | 0.99348246 |
| Ct2-2 | NA3-2 | 0.99512259 |
| Ct2-2 | NA1-2 | 0.99566519 |
| Ct2-2 | Ct3-2 | 0.99755989 |
| Ct3-2 | NA2-2 | 0.99413358 |
| Ct3-2 | NA1-2 | 0.99561707 |
| Ct3-2 | NA3-2 | 0.99549209 |
| NA1-2 | NA3-2 | 0.99763707 |
| NA1-2 | NA2-2 | 0.99559868 |
| NA2-2 | NA3-2 | 0.99597901 |

*FIG. 8*

| Ct1-2 | Ct2-2 | 0.9975867 |
|---|---|---|
| Ct1-2 | Wln3-2 | 0.95585096 |
| Ct1-2 | Ct3-2 | 0.99619579 |
| Ct1-2 | Wln2-2 | 0.96703788 |
| Ct1-2 | Wln1-2 | 0.94162487 |
| Ct2-2 | Wln1-2 | 0.92947092 |
| Ct2-2 | Wln3-2 | 0.94598904 |
| Ct2-2 | Ct3-2 | 0.99755989 |
| Ct2-2 | Wln2-2 | 0.95941539 |
| Ct3-2 | Wln1-2 | 0.92655694 |
| Ct3-2 | Wln3-2 | 0.94474515 |
| Ct3-2 | Wln2-2 | 0.95787811 |
| Wln1-2 | Wln3-2 | 0.99399028 |
| Wln1-2 | Wln2-2 | 0.99142989 |
| Wln2-2 | Wln3-2 | 0.99311974 |

FIG. 9

| Ct1-2 | W1-2 | 0.96478842 |
| Ct1-2 | Ct2-2 | 0.9975867 |
| Ct1-2 | W2-2 | 0.97508251 |
| Ct1-2 | W3-2 | 0.96281811 |
| Ct1-2 | Ct3-2 | 0.99619579 |
| Ct2-2 | W1-2 | 0.95522503 |
| Ct2-2 | Ct3-2 | 0.99755989 |
| Ct2-2 | W3-2 | 0.95470146 |
| Ct2-2 | W2-2 | 0.96823323 |
| Ct3-2 | W1-2 | 0.95141461 |
| Ct3-2 | W2-2 | 0.96575062 |
| Ct3-2 | W3-2 | 0.95163553 |
| W1-2 | W2-2 | 0.99527076 |
| W1-2 | W3-2 | 0.99610766 |
| W2-2 | W3-2 | 0.99650047 |

NUCLEIC ACID STABILIZATION REAGENT, KITS, AND METHODS OF USE THEREOF

This application is a continuation of International Patent Application No. PCT/US2017/025065, filed Mar. 30, 2017, which claims the benefit under 35 U.S.C. 119(e) of U.S. Provisional Application No. 62/316,514, filed on Mar. 31, 2016, the disclosure of which is herein incorporated by reference in its entirety.

BACKGROUND

In biosciences and related fields, it can be useful to store biological cells for periods of time ranging from several hours to overnight to several days before isolating a population of nucleic acids from the biological cells for analysis. It is desirable that the population of nucleic acids, or at least a portion thereof, being analyzed are representative of the state of the cell prior to storage. Changes of nucleic acid expression due to storage are preferably minimized. Some embodiments of the present disclosure include reagents and processes for stabilizing nucleic acids within a biological cell for later isolation, advantageously reducing the incidence of altered nucleic acid expression due to intervening storage.

SUMMARY

Kits for stabilizing nucleic acid within a biological cell are described herein where the kit includes at least one irreversible protein translation inhibitor; at least one ribonucleic acid transcription inhibitor; and at least one electron transport chain agent chosen from an electron transport chain inhibitor and an electron transport chain decoupling agent.

In another aspect, a method is described for stabilizing nucleic acid in a biological cell, including contacting the biological cell with at least one irreversible protein translation inhibitor; at least one ribonucleic acid transcription inhibitor; and at least one electron transport chain agent comprising an electron transport chain inhibitor and/or an electron transport chain decoupling agent, wherein the contacting is performed for a period of time sufficient to stabilize the population of nucleic acids and thereby convert the biological cell to a stabilized biological cell. The at least one irreversible protein translation inhibitor; at least one ribonucleic acid transcription inhibitor; and at least one electron transport chain agent comprising an electron transport chain inhibitor and/or an electron transport chain decoupling agent may be components of a nucleic acid stabilization reagent, which can be any nucleic acid stabilization reagent described herein. In various embodiments, the method may further include storing the stabilized biological cell in the presence of each of the at least one irreversible protein translation inhibitor, at least one ribonucleic acid transcription inhibitor, and at least one electron transport chain agent for any period of time as described herein. In some embodiments, the step of storing may be performed at a temperature lower than 20° C. In various embodiments, the step of storing may be performed at a temperature of 0° C. to about 4° C.

In another aspect, a method is described for stabilizing nucleic acid in a biological cell located within a microfluidic device having an enclosure, including the steps of: disposing the biological cell within the enclosure of the microfluidic device, wherein the enclosure comprises a flow region and at least one chamber and at least one chamber fluidically connected to the flow region, wherein the flow region and at least one chamber are configured to contain a fluidic medium; and contacting the biological cell with at least one irreversible protein translation inhibitor; at least one ribonucleic acid transcription inhibitor; and at least one electron transport chain agent comprising an electron transport chain inhibitor and/or an electron transport chain decoupling agent, wherein the contacting is performed for a period of time sufficient to stabilize the population of nucleic acids in the biological cell, and thereby convert the biological cell to a stabilized biological cell. The at least one irreversible protein translation inhibitor; at least one ribonucleic acid transcription inhibitor; and at least one electron transport chain agent comprising an electron transport chain inhibitor and/or an electron transport chain decoupling agent may be components of a nucleic acid stabilization reagent, which can be any nucleic acid stabilization reagent described herein. The at least one chamber can be a sequestration pen. The flow region can be a microfluidic channel.

BRIEF DESCRIPTION OF THE DRAWINGS

FIG. 6 is a tabular representation of the Differential Expression (DE) for cells treated with the stabilization reagent (In) compared to that of the Lysis Control samples (LC) in Example 1.

FIG. 7 is a tabular representation of the Differential Expression (DE) for Lysis Control cells (LC) stored at −80° C. compared to that of cells stored at 4° C. with no stabilization reagent (NA) in Example 1.

FIG. 8 is a tabular representation of the Differential Expression (DE) for cells washed into PBS with subsequent addition of the stabilization reagent of Example 1 (WIn) and storage at 4° C., compared to that of the Lysis Control cells (LC) stored at −80° C.

FIG. 9 is a tabular representation of the Differential Expression (DE) for cells washed into PBS having nothing added (W), with storage at 4° C., compared to that of the Lysis Control samples (LC), stored at −80° C., of Example 1.

DETAILED DESCRIPTION OF EXEMPLARY EMBODIMENTS

Figure 1A:
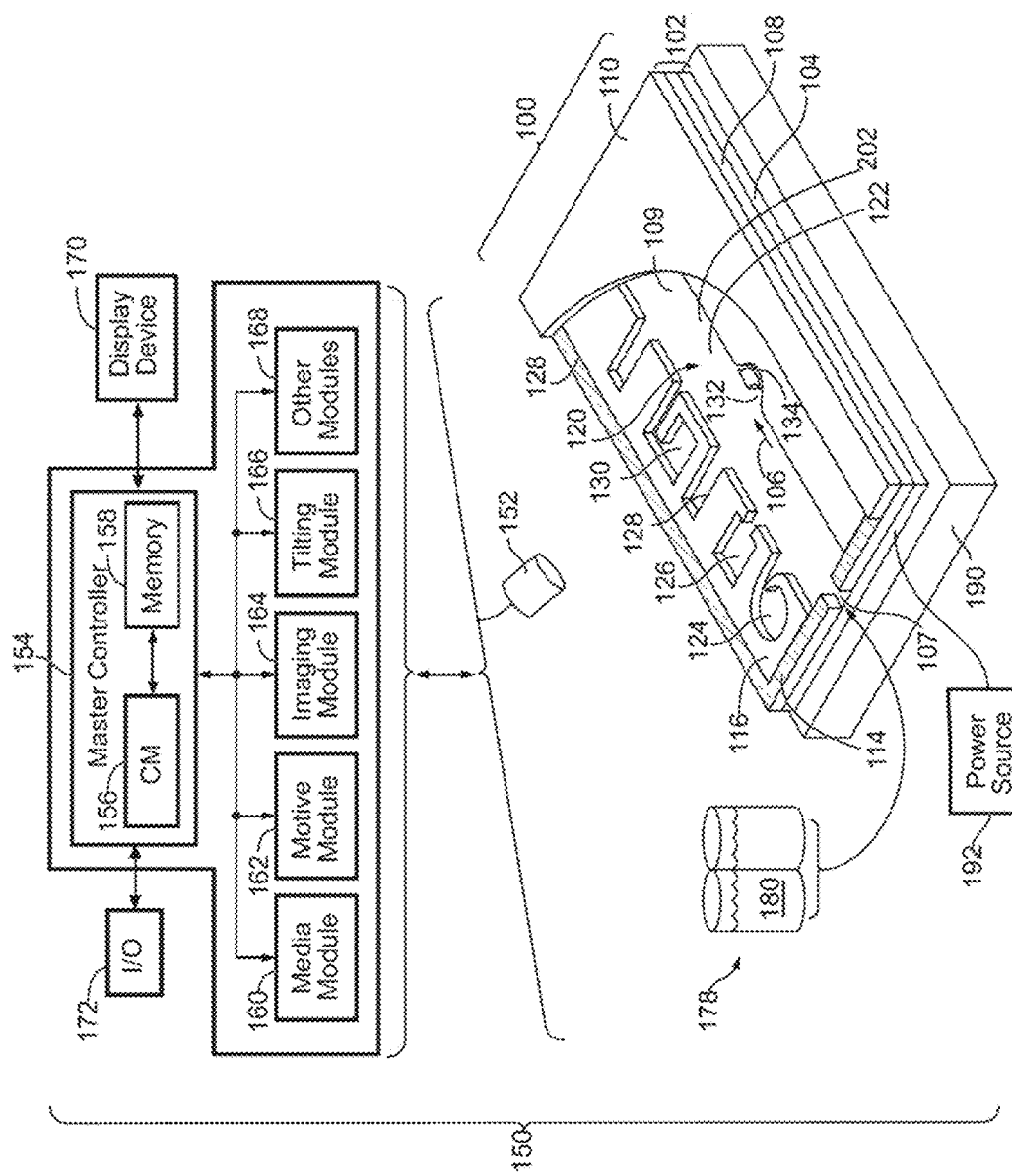
FIG. 1A illustrates an example of a system for use with a microfluidic device and associated control equipment according to some embodiments of the disclosure.

This specification describes exemplary embodiments and applications of the disclosure. The disclosure, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. In addition, where reference is made to a list of elements (e.g., elements a, b, c), such reference is intended to include any one of the listed elements by itself, any combination of less than all of the listed elements, and/or a combination of all of the listed elements.

Section divisions in the specification are for ease of review only and do not limit any combination of elements discussed.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

As used herein, the term "ones" means more than one. As used herein, the term "plurality" can be 2, 3, 4, 5, 6, 7, 8, 9, 10, or more.

As used herein, the term "disposed" encompasses within its meaning "located."

As used herein, a "microfluidic device" or "microfluidic apparatus" is a device that includes one or more discrete microfluidic circuits configured to hold a fluid, each microfluidic circuit comprised of fluidically interconnected circuit elements, including but not limited to region(s), flow path(s), channel(s), chamber(s), and/or pen(s), and at least two ports configured to allow the fluid (and, optionally, micro-objects suspended in the fluid) to flow into and/or out of the microfluidic device. Typically, a microfluidic circuit of a microfluidic device will include at least one microfluidic channel and at least one chamber, and will hold a volume of fluid of less than about 1 mL, e.g., less than about 750, 500, 250, 200, 150, 100, 75, 50, 25, 20, 15, 10, 9, 8, 7, 6, 5, 4, 3, or 2 μL. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300 μL.

As used herein, a "nanofluidic device" or "nanofluidic apparatus" is a type of microfluidic device having a microfluidic circuit that contains at least one circuit element configured to hold a volume of fluid of less than about 1 μL, e.g., less than about 750, 500, 250, 200, 150, 100, 75, 50, 25, 20, 15, 10, 9, 8, 7, 6, 5, 4, 3, 2, 1 nL or less. Typically, a nanofluidic device will comprise a plurality of circuit elements (e.g., at least 2, 3, 4, 5, 6, 7, 8, 9, 10, 15, 20, 25, 50, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, or more). In certain embodiments, one or more (e.g., all) of the at least one circuit elements may be configured to hold a volume of fluid of about 100 pL to 1 nL, 100 pL to 2 nL, 100 pL to 5 nL, 250 pL to 2 nL, 250 pL to 5 nL, 250 pL to 10 nL, 500 pL to 5 nL, 500 pL to 10 nL, 500 pL to 15 nL, 750 pL to 10 nL, 750 pL to 15 nL, 750 pL to 20 nL, 1 to 10 nL, 1 to 15 nL, 1 to 20 nL, 1 to 25 nL, or 1 to 50 nL. In other embodiments, one or more (e.g., all) of the at least one circuit elements may be configured to hold a volume of fluid of about 100 to 200 nL, 100 to 300 nL, 100 to 400 nL, 100 to 500 nL, 200 to 300 nL, 200 to 400 nL, 200 to 500 nL, 200 to 600 nL, 200 to 700 nL, 250 to 400 nL, 250 to 500 nL, 250 to 600 nL, or 250 to 750 nL.

A microfluidic device or a nanofluidic device may be referred to herein as a "microfluidic chip" or a "chip"; or "nanofluidic chip" or "chip".

A "microfluidic channel" or "flow channel" as used herein refers to flow region of a microfluidic device having a length that is significantly longer than both the horizontal and vertical dimensions. For example, the flow channel can be at least 5 times the length of either the horizontal or vertical dimension, e.g., at least 10 times the length, at least 25 times the length, at least 100 times the length, at least 200 times the length, at least 500 times the length, at least 1,000 times the length, at least 5,000 times the length, or longer. In some embodiments, the length of a flow channel is in the range of from about 100,000 microns to about 500,000 microns, including any range therebetween. In some embodiments, the horizontal dimension is in the range of from about 100 microns to about 1000 microns (e.g., about 150 to about 500 microns) and the vertical dimension is in the range of from about 25 microns to about 200 microns, e.g., from about 40 to about 150 microns. It is noted that a flow channel may have a variety of different spatial configurations in a microfluidic device, and thus is not restricted to a perfectly linear element. For example, a flow channel may be, or include one or more sections having, the following configurations: curve, bend, spiral, incline, decline, fork (e.g., multiple different flow paths), and any combination thereof. In addition, a flow channel may have different cross-sectional areas along its path, widening and constricting to provide a desired fluid flow therein.

As used herein, the term "obstruction" refers generally to a bump or similar type of structure that is sufficiently large so as to partially (but not completely) impede movement of target micro-objects between two different regions or circuit elements in a microfluidic device. The two different regions/circuit elements can be, for example, a microfluidic sequestration pen and a microfluidic channel, or a connection region and an isolation region of a microfluidic sequestration pen.

As used herein, the term "constriction" refers generally to a narrowing of a width of a circuit element (or an interface between two circuit elements) in a microfluidic device. The constriction can be located, for example, at the interface between a microfluidic sequestration pen and a microfluidic channel, or at the interface between an isolation region and a connection region of a microfluidic sequestration pen.

As used herein, the term "transparent" refers to a material which allows visible light to pass through without substantially altering the light as is passes through.

As used herein, the term "micro-object" refers generally to any microscopic object that may be isolated and/or manipulated in accordance with the present disclosure. Non-limiting examples of micro-objects include: inanimate micro-objects such as microparticles; microbeads (e.g., polystyrene beads, Luminex™ beads, or the like); magnetic beads; microrods; microwires; quantum dots, and the like; biological micro-objects such as cells; biological organelles; vesicles, or complexes; synthetic vesicles; liposomes (e.g., synthetic or derived from membrane preparations); lipid nanorafts, and the like; or a combination of inanimate micro-objects and biological micro-objects (e.g., microbeads attached to cells, liposome-coated micro-beads, liposome-coated magnetic beads, or the like). Beads may include moieties/molecules covalently or non-covalently attached, such as fluorescent labels, proteins, carbohydrates, antigens, small molecule signaling moieties, or other chemical/biological species capable of use in an assay. Lipid nanorafts have been described, for example, in Ritchie et al. (2009) "Reconstitution of Membrane Proteins in Phospholipid Bilayer Nanodiscs," Methods Enzymol., 464:211-231.

As used herein, the term "cell" is used interchangeably with the term "biological cell." Non-limiting examples of biological cells include eukaryotic cells, plant cells, animal cells, such as mammalian cells, reptilian cells, avian cells, fish cells, or the like, prokaryotic cells, bacterial cells, fungal cells, protozoan cells, or the like, cells dissociated from a tissue, such as muscle, cartilage, fat, skin, liver, lung, neural tissue, and the like, immunological cells, such as T cells, B cells, natural killer cells, macrophages, and the like, embryos (e.g., zygotes), oocytes, ova, sperm cells, hybridomas, cultured cells, cells from a cell line, cancer cells, infected cells, transfected and/or transformed cells, reporter cells, and the like. A mammalian cell can be, for example, from a human, a mouse, a rat, a horse, a goat, a sheep, a cow, a primate, or the like.

A colony of biological cells is "clonal" if all of the living cells in the colony that are capable of reproducing are daughter cells derived from a single parent cell. In certain embodiments, all the daughter cells in a clonal colony are derived from the single parent cell by no more than 10 divisions. In other embodiments, all the daughter cells in a clonal colony are derived from the single parent cell by no more than 14 divisions. In other embodiments, all the daughter cells in a clonal colony are derived from the single parent cell by no more than 17 divisions. In other embodiments, all the daughter cells in a clonal colony are derived from the single parent cell by no more than 20 divisions. The term "clonal cells" refers to cells of the same clonal colony.

As used herein, a "colony" of biological cells refers to 2 or more cells (e.g. about 2 to about 20, about 4 to about 40, about 6 to about 60, about 8 to about 80, about 10 to about 100, about 20 to about 200, about 40 to about 400, about 60 to about 600, about 80 to about 800, about 100 to about 1000, or greater than 1000 cells).

As used herein, the term "maintaining (a) cell(s)" refers to providing an environment comprising both fluidic and gaseous components and, optionally a surface, that provides the conditions necessary to keep the cells viable and/or expanding.

As used herein, the term "expanding" when referring to cells, refers to increasing in cell number.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein, "capture moiety" is a chemical or biological species, functionality, or motif that provides a recognition site for a micro-object. A selected class of micro-objects may recognize the in situ-generated capture moiety and may bind or have an affinity for the in situ-generated capture moiety. Non-limiting examples include antigens, antibodies, and cell surface binding motifs.

As used herein, "flowable polymer" is a polymer monomer or macromer that is soluble or dispersible within a fluidic medium (e.g., a pre-polymer solution). The flowable polymer may be input into a microfluidic flow region and flow with other components of a fluidic medium therein.

As used herein, "photoinitiated polymer" refers to a polymer (or a monomeric molecule that can be used to generate the polymer) that upon exposure to light, is capable of crosslinking covalently, forming specific covalent bonds, changing regiochemistry around a rigidified chemical motif, or forming ion pairs which cause a change in physical state, and thereby forming a polymer network. In some instances, a photoinitiated polymer may include a polymer segment bound to one or more chemical moieties capable of crosslinking covalently, forming specific covalent bonds, changing regiochemistry around a rigidified chemical motif, or forming ion pairs which cause a change in physical state. In some instances, a photoinitiated polymer may require a photoactivatable radical initiator to initiate formation of the polymer network (e.g., via polymerization of the polymer).

As used herein, "antibody" refers to an immunoglobulin (Ig) and includes both polyclonal and monoclonal antibodies; primatized (e.g., humanized); murine; mouse-human; mouse-primate; and chimeric; and may be an intact molecule, a fragment thereof (such as scFv, Fv, Fd, Fab, Fab' and F(ab)'2 fragments), or multimers or aggregates of intact molecules and/or fragments; and may occur in nature or be produced, e.g., by immunization, synthesis or genetic engineering. An "antibody fragment," as used herein, refers to fragments, derived from or related to an antibody, which bind antigen and which in some embodiments may be derivatized to exhibit structural features that facilitate clearance and uptake, e.g., by the incorporation of galactose residues. This includes, e.g., F(ab), F(ab)'2, scFv, light chain variable region (VL), heavy chain variable region (VH), and combinations thereof.

As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that, averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the device.

As used herein, a "flow path" refers to one or more fluidically connected circuit elements (e.g. channel(s), region(s), chamber(s) and the like) that define, and are subject to, the trajectory of a flow of medium. A flow path is thus an example of a swept region of a microfluidic device. Other circuit elements (e.g., unswept regions) may be fluidically connected with the circuit elements that comprise the flow path without being subject to the flow of medium in the flow path.

As used herein, "isolating a micro-object" confines a micro-object to a defined area within the microfluidic device.

A microfluidic (or nanofluidic) device can comprise "swept" regions and "unswept" regions. As used herein, a "swept" region is comprised of one or more fluidically interconnected circuit elements of a microfluidic circuit, each of which experiences a flow of medium when fluid is flowing through the microfluidic circuit. The circuit elements of a swept region can include, for example, regions, channels, and all or parts of chambers. As used herein, an "unswept" region is comprised of one or more fluidically interconnected circuit element of a microfluidic circuit, each of which experiences substantially no flux of fluid when fluid is flowing through the microfluidic circuit. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region. For example, a flow channel of a micro-fluidic device is an example of a swept region while an isolation region (described in further detail below) of a microfluidic device is an example of an unswept region.

The capability of biological micro-objects (e.g., biological cells) to produce specific biological materials (e.g., proteins, such as antibodies) can be assayed in such a microfluidic device. In a specific embodiment of an assay, sample material comprising biological micro-objects (e.g., cells) to be assayed for production of an analyte of interest can be loaded into a swept region of the microfluidic device. Ones of the biological micro-objects (e.g., mammalian cells, such as human cells) can be selected for particular characteristics and disposed in unswept regions. The remaining sample material can then be flowed out of the swept region and an assay material flowed into the swept region. Because the selected biological micro-objects are in unswept regions, the selected biological micro-objects are not substantially affected by the flowing out of the remaining sample material or the flowing in of the assay material. The selected biological micro-objects can be allowed to produce the analyte of interest, which can diffuse from the unswept regions into the swept region, where the analyte of interest can react with the assay material to produce localized detectable reactions, each of which can be correlated to a particular unswept region. Any unswept region associated with a detected reaction can be analyzed to determine which, if any, of the biological micro-objects in the unswept region are sufficient producers of the analyte of interest.

As referred to herein, a "stabilized biological cell" is a biological cell maintained under conditions different from typical culturing conditions or in-vivo conditions, wherein such conditions (i.e. "maintenance conditions") stabilize the nucleic acids or the transcriptome of the cell such that the population of nucleic acids or transcriptome is substantially the same as the population of nucleic acids or a transcriptome of the cell under typical culture conditions or in-vivo conditions. The maintenance conditions may include conditions conducive to storage of the stabilized biological cell, including storage at reduced temperatures. In certain embodiments, the stabilized transcriptome of the stabilized biological cell is substantially the same as the transcriptome of a corresponding cell (i.e. of the same type and/or provenance) growing under typical culture conditions or in-vivo conditions.

As used herein, a "reversible" inhibitor inhibits the activity of a biomolecule (e.g., protein, nucleic acid, ribozyme, complex or the like) by binding non-covalently with the biomolecule, thereby reducing or eliminating the activity of the biomolecule while bound. A reversible inhibitor has a characteristic set of kinetic parameters (e.g., binding affinity, association rate or "on rate", and dissociation rate or "off rate") relative to the inhibited biomolecule. Accordingly, different reversible inhibitors of a particular biomolecule may have different binding affinities, association rates and/or dissociation rates. Differences in such kinetic parameters reflect differences in the chemical interactions between the reversible inhibitors and the target biomolecule, such as binding to different portions of the target biomolecule.

As referred to herein, an "irreversible" inhibitor inhibits the activity of a biomolecule by either forming covalent bonds to the biomolecule or by having such a high binding affinity for the biomolecule that the inhibitor does not dissociate from the biomolecule within any reasonable experimental time period and is therefore essentially irreversible.

As referred to herein, "cell membrane permeable" refers to the ability of a molecule to passively diffuse through a cell membrane in sufficient amounts to be effectively intracellularly active, and is a function of the ionic nature (charge), polarity, and size (molar mass) of the molecule. Smaller, more lipid soluble molecules may be more permeable that larger, more charged molecules.

As referred to herein, a "master mix" is a premixed, ready to use combination of reagents. A master mix for a stabilization reagent may have all components of the reagent (e.g., protein translation inhibitor(s), nucleic acid transcription inhibitors, and optional protease inhibitors). The master mix may have the components present at a concentration anywhere from about 1× to about 1000× (e.g., 2×, 5×, 10×, 20×, 100×, or 1000×) the concentration actually used within the stabilizing reaction. In some other embodiments, a master mix may have some (e.g., 2, 3, etc.) components needed for the complete reagent, where the remaining components may be added just prior to use.

Nucleic acid stabilization reagent and methods of use thereof. It may be desired to isolate a population of nucleic acids from a biological cell after the cell has been stored for a period of time, ranging from a few hours to several days. Upon storage, typically at reduced temperatures, subsets of the nucleic acids of the biological cell may be damaged, under produced (e.g., in reduced proportions), or overproduced as a result of the cell's exposure to the storage conditions or contact with agents used to prepare the cell for storage. In some embodiments, detection of the nucleic acids via sequencing or hybridization experiments may lead to meaningful information about the state of the biological cell only if the nucleic acids that are retrieved are representative in type and in population frequency of the nucleic acids present in the cell prior to storage. Currently available treatments for preparing cells for storage usually include cross-linking of proteins, nucleic acids, etc., but it is an improvement to be able to stabilize cells for storage without cross-linking, as recovery of the desired nucleic acids from within the mass of crosslinked materials of a "fixed" cell (e.g., treated with a crosslinking reagent) can be impaired and lead to reduced amounts of materials. This is particularly a problem for retrieval of nucleic acids from single cells.

Described herein are compositions, methods and kits for stabilizing the nucleic acids present in a biological cell, prior to subjecting the biological cell to storage. Stabilizing includes stopping cellular processes which could lead to production of different nucleic acids or altered amounts of the same nucleic acids relative to what the biological cell had been producing under its normative conditions. Exposure to temperature changes or preservatives may induce physical changes (e.g. crystallization of aqueous components), chemical changes, or biological changes such as induction of stress or cell death pathways. Thus, detection of these exogenously induced nucleic acids retrieved from the biological cell may not permit true understanding of the state of the cell prior to storage.

It has been surprisingly discovered by Applicant that a stabilization reagent containing a mixture of agents designed to stop intracellular nucleic acid production and/or function can stabilize nucleic acids during storage (and for post-storage isolation) by retaining the pattern and levels of their production at levels substantially similar to levels observed prior to exposure to the storage conditions/stabilization reagent.

In some embodiments, the stabilization reagent may be used to stabilize deoxynucleic acids for storage and subsequent DNA isolation. In other embodiments, the stabilization reagent may stabilize ribonucleic acid (RNA) for storage and subsequent isolation. In some embodiments, the stabilization reagent may stabilize messenger RNA (mRNA) for storage and subsequent isolation. In some embodiments, the stabilization reagent may stabilize both DNA and RNA (e.g., mRNA).

Stabilization Reagent. In some embodiments, the stabilization reagent includes at least one irreversible protein translation inhibitor, at least one ribonucleic acid transcription inhibitor, and at least one electron transport chain agent. The electron transport chain agent may be either an electron transport chain inhibitor or it may be an electron transport decoupling agent. In some embodiments, the stabilization reagent may include a second protein translation inhibitor, different from the first irreversible protein translation inhibitor. The second protein translation inhibitor may be a reversible inhibitor and/or may be fast-acting compared to the irreversible protein translation inhibitor.

Irreversible protein translation inhibitor. At least one irreversible protein translation inhibitor may be a component of the stabilization reagent. The irreversible protein translation inhibitor may substantially prevent synthesis of new proteins. Irreversibility is desirable to stop protein synthesis at the point of reagent introduction and before exposure to any other storage conditions or reagents, either of which might initiate changes in protein synthesis in response to the exposure. The irreversible inhibitor may be either fast-acting (e.g., taking effect within a period of about 10 mins to about 30 mins) or slow-acting (taking effect within one or more hours). The irreversible protein translation inhibitor may be cell membrane permeable, e.g., having solubility in lipid phases, in order to diffuse more easily into the cell and enter the cell in an amount sufficient to inhibit protein translation. The irreversible protein translation inhibitor may be selected from an aminoglycoside antibiotic (including but not limited to amikacin, gentamicin, kanamycin, neomycin, streptomycin, and tobramycin), D-galactosamine, and/or emetine (CAS No. 483-18-1). In some embodiments, the irreversible protein translation inhibitor may be emetine. The irreversible protein translation inhibitor may inhibit protein translation by binding to ribosomes, and causing ribosome stalling, thereby stopping protein synthesis. In one non-limiting example, emetine binds irreversibly to the 40S subunit of the eukaryotic (including, but not limited to mammalian or human) ribosome to initiate ribosome stalling. The irreversible protein translation inhibitor may contact the biological cell by addition of a solution in which the irreversible protein translation inhibitor is present in a concentration from about 1.0 micromolar to about 100 millimolar; about 1.0 micromolar to about 50 millimolar; about 1.0 micromolar to about 5 millimolar; about 5 micromolar to about 15 millimolar; about 5 micromolar to about 10 millimolar; about 0.1 millimolar to about 5 millimolar; or any value in between these ranges.

The second protein translation inhibitor. A second protein translation inhibitor may be a component of the stabilization reagent. The second protein translation inhibitor is different from the first protein translation inhibitor of the stabilization reagent. The second protein translation inhibitor may be an irreversible or a reversible protein translation inhibitor. The second protein translation inhibitor may be cell membrane permeable, e.g., sufficiently lipid soluble to be able to cross the cell membrane and enter the cell in an amount sufficient to inhibit protein translation. The second protein translation inhibitor may act via the same mechanism to stop new protein synthesis or by a different mechanism than that of the irreversible protein translation inhibitor component of the stabilization reagent. The second protein translation inhibitor may be fast acting. By fast acting, the application means that the inhibitor substantially stops protein synthesis (substantially stops protein synthesis meaning at least 90% termination of protein synthesis) within 30 minutes of being added to the biological cell. Thus, in some embodiments, a fast acting protein translation inhibitor may substantially stop protein synthesis within a period of about 1 min, 2 min, 3 min, 5 min, or about 10 min to about 30 min. In some embodiments, the second protein translation inhibitor may be selected from diazooxide, a glutarimide antibiotic, and/or an ipecac alkaloid. Glutarimide antibiotics may include but are not limited to cycloheximide, acetoxycycloheximide, streptimidone, streptovitacins, inactone, epiderstatin, acetiketal and dorrigocin. In some embodiments, the second protein translation inhibitor may be cycloheximide (CAS No. 66-81-9). Cycloheximide is a reversible inhibitor, and can inhibit translation elongation by binding to 60S ribosomal unit and blocking the movement of peptidyl-RNA from the acceptor (aminoacyl) to the donor (peptidyl) site on the ribosome. The second protein translation inhibitor may contact the biological cell by addition of a solution in which the second protein translation inhibitor is present at a concentration from about 1.0 micromolar to about 100 millimolar; about 1.0 micromolar to about 50 millimolar; about 1.0 micromolar to about 5 millimolar; about 5 micromolar to about 15 millimolar; about 5 micromolar to about 10 millimolar; about 0.1 millimolar to about 5 millimolar; or any value in between these ranges.

Ribonucleic acid transcription inhibitor. At least one ribonucleic acid transcription inhibitor may be a component of the stabilization reagent. The ribonucleic acid transcription inhibitor may be an irreversible or a reversible ribonucleic acid transcription inhibitor. Reversible ribonucleic acid transcription inhibitors may include, but are not limited to CDK9 inhibitors (e.g., 5,6-dichloro-1-beta-D-ribofuranosylbenzimidazole (DRB)) and flavorpiridol. Irreversible ribonucleic acid transcription inhibitors may include but are not limited to aureothricin, thiolutin, aminitin, or triptolide. In other embodiments, an irreversible ribonucleic acid transcription inhibitor may be Actinomycin. In various embodiments, the ribonucleic acid transcription inhibitor may be triptolide (CAS no. 38748-32-2). The ribonucleic acid transcription inhibitor may be cell membrane permeable and enter the cell in an amount sufficient to inhibit ribonucleic acid transcription. The ribonucleic acid transcription inhibitor may be either fast-acting (e.g., takes effect within a period of about 1, 2, 3, 5, 10 mins to about 30 mins) or may be slow-acting (taking effect within one or more hours). In some embodiments, the ribonucleic acid transcription inhibitor may be fast-acting. The ribonucleic acid transcription inhibitor may contact the biological cell by addition of a solution in which the ribonucleic acid transcription inhibitor is present at a concentration from about 10 nanomolar to about 50 millimolar; about 0.01 micromolar to about 50 millimolar; about 0.1 micromolar to about 500 micromolar; about 0.1 micromolar to about 50 micromolar; or any value in between these ranges.

Electron transport chain agent. At least one electron transport chain agent may be a component of the stabilization reagent. The electron transport chain agent may be cell membrane permeable and enter the cell in an amount sufficient to disrupt the electron transport chain. The electron transport chain agent may be either fast-acting (e.g., takes effect within a period of about 1, 2, 3, 5, 10 mins to about 30 mins) or may be slow-acting (taking effect within one or more hours). In some embodiments, the electron transport chain agent may be fast-acting. The electron transport chain agent may have reversible or irreversible activity upon the electron transport chain. The electron transport chain agent may be an electron transport chain inhibitor, examples of which include, but are not limited to rotenone, antimycin $A_1$, 2-thenoyltrifluoroacetone, carboxin, cyanide, sodium azide, and oligomycin. Alternatively, the electron transport chain agent may be an electron transport chain decoupling agent, examples of which include, but are not limited to 2,4 dinitrophenol, dicumarol, and carbonylcyanide-4-(trifluoromethoxy)-phenylhydrazone. Electron transport decoupling agents may be selected as the electron transfer chain agent due to their general characteristic of lipid solubility. In some embodiments, the electron transfer chain agent may be sodium azide. The electron transport chain agent may contact the biological cell by addition of a solution in which the electron transport chain agent is present at a concentration from about 0.1 micromolar to about 100 millimolar; about 10 micromolar to about 50 millimolar; about 0.3 millimolar to about 25 millimolar; about 0.3 millimolar to about 15 millimolar; about 0.5 millimolar to about 10 millimolar; about 1 millimolar to about 5 millimolar; or any value in between these ranges.

The stabilization reagent may provide the at least one irreversible protein translation inhibitor, at least one ribonucleic acid transcription inhibitor, and at least one electron transport chain agent within a single solution, or may have less than all of the at least one irreversible protein translation inhibitor, at least one ribonucleic acid transcription inhibitor, and at least one electron transport chain agent within a single solution. The individual components of the stabilization reagent may be provided each as a separate solution. The individual components of the stabilization reagent may contact the biological cell sequentially or simultaneously. In some embodiments, the components of the stabilization reagent contact the biological cell simultaneously, e.g., are present in the same solution, thereby being added simultaneously. In other embodiments, the components may be added sequentially by adding the ribonucleic acid transcription inhibitor first, followed by the other components of the stabilization reagent.

Other components of the stabilization reagent. In some embodiments, the stabilization reagent may not include a RNase inhibitor. The combination of the protein translation inhibitor(s), ribonucleic acid transcription inhibitor, and electron transport chain agent may sufficiently stop intracellular processes, thereby stabilizing the nucleic acids, without requiring addition of a RNase inhibitor.

RNase inhibitors. In other embodiments, the stabilization reagent may include one or more RNase inhibitors. Any suitable RNase inhibitor may be included, which may include but is not limited to a ribonuclease inhibitor protein (e. g., the 49 kDA, leucine and cysteine rich protein; ortholog; or homolog thereof) or the active component(s) or agent(s) of any of the following commercially available reagents: RNasin® Ribonuclease Inhibitor (Promega); RNasin® Plus Ribonuclease Inhibitor (Promega); SUPERase·In™ RNase inhibitor (ThermoFisher Scientific); RNaseOUT™ Recombinant ribonuclease inhibitor (ThermoFisher Scientific); ANTI-RNase (ThermoFisher Scientific); RNAsecure™ reagent (ThermoFisher Scientific)

Protease inhibitor. In various embodiments, the stabilization reagent for stabilizing nucleic acids in the biological cell may further include a protease inhibitor. The protease inhibitor may be a serine, cysteine, aspartic, or metalloprotease inhibitor. In other embodiments, the protease inhibitor may be a threonine or glutamic protease inhibitor.

Serine protease inhibitor. The serine protease inhibitor may be a reversible or an irreversible inhibitor. The serine protease inhibitor may be cell membrane permeable (e.g., may be able to diffuse through the cell membrane and enter the cell in amount sufficient to inhibit the serine protease). Serine protease inhibitors include but are not limited to phenylmethylsulfonyl fluoride (PMSF), 3,4, dichloroisocoumarin, diisopropylfluoro phosphate, N-p-tosyl-L-lysine chloromethylketone (TLCK), and N-p-tosyl-L-phenylalanine chloromethylketone (TPCK).

Cysteine protease inhibitor. The cysteine protease inhibitor may be a reversible or an irreversible inhibitor, and may further be cell membrane permeable (e.g., may be able to diffuse through the cell membrane and enter the cell in amount sufficient to inhibit the cysteine protease). The cysteine protease inhibitor may be an inhibitor of caspase proteases or an inhibitor of cathepsin cysteine proteases. A cysteine protease inhibitor may be, but is not limited to any of E-64 (N-(trans-epoxysuccinyl)-L-leucine-4-guanidinobutylamide, Selleck Chem), N-benzoyl phenylalanine fluoromethyl ketone (Z-FA-FMK), and N-benzoyl valinyl alaninyl aspartic fluoromethyl ketone (Z-VAD-FMK).

Metalloprotease inhibitor. The metalloprotease inhibitor may be a reversible or an irreversible inhibitor. The metalloprotease inhibitor may be cell membrane permeable (e.g., may be able to diffuse through the cell membrane and enter the cell in amount sufficient to inhibit the metalloprotease). Examples of suitable metalloprotease inhibitors include but are not limited to phosphoramidon, bestatin, ethylenediamine tetraacetic acid (EDTA), marimistat, batimastat, zinc methacrylate, and MMP inhibitor III (CAS No. 927827-98-3, N'-hydroxy-N-(1-methylcarbamoyl)-3-phenyl-propyl)-2-(2-methylpropyl)butanediamide).

Buffers and media for the stabilization reagent. The stabilization reagent may include aqueous and/or non-aqueous solvents to solubilize the components of the stabilization reagent. These solvents may be selected to permit long term storage of the combinations of inhibitors and energy transfer chain agent. Useful solvents may include dimethylsulfoxide (DMSO), glycerol, water, ethyl alcohol, and the like. If a non-aqueous solvent is used, buffers may not be required. Buffering of aqueous solutions will be configured to both prevent deterioration of the components of the stabilization reagent and to provide a suitable pH range for the stabilizing reaction itself. If storage at reduced temperatures such as −20° C. is desirable, anti-freezing additives or solvents, such as, but not limited to glycerol or DMSO, may be included in the stabilization reagent.

Methods of Stabilizing Nucleic Acids. When isolating cells from a biological sample such as a tissue sample, fine needle aspirate sample, lavage sample, and the like, it may be desirable to partially process cells from the sample and then to store the cells, for convenience or other reasons, before performing the step of extracting nucleic acids for further analysis. Methods are provided for stabilizing nucleic acids within a biological cell prior to (and during) storage. Subsequent to storage, the nucleic acids, or a population thereof, of the biological cell may be isolated from the cell. In various embodiments, the nucleic acids to be stabilized for isolation after storage may be deoxynucleic acid (DNA). In other embodiments, the nucleic acids to be stabilized for isolation after storage may be ribonucleic acid (RNA). In some embodiments, the RNA to be stabilized for isolation after storage may be messenger RNA (mRNA). mRNA may be isolated from the stabilized nucleic acids of the stabilized cell in order to analyze the transcriptome of the biological cell. Analysis of the transcriptome of the biological cell may be used to identify genes that are differentially expressed by the biological cell. The differential expression may be in comparison to an expression level of a comparable "healthy" cell or to the expression level of a different cell type. The transcriptome of the biological cell is preferably not substantially disrupted during the process of stabilization and storage, thus allowing examination the amount and identities of RNA operant within the biological cell.

Accordingly, a method of stabilizing a population of nucleic acids in a biological cell is provided, which includes the steps of contacting the biological cell with at least one irreversible protein translation inhibitor; at least one ribonucleic acid transcription inhibitor; and at least one electron transport chain agent which may be an electron transport chain inhibitor and/or an electron transport chain decoupling agent, where the contacting is performed for a period of time sufficient to stabilize the population of nucleic acids and thereby convert the biological cell to a stabilized biological cell. The at least one irreversible protein translation inhibitor; at least one ribonucleic acid transcription inhibitor; and at least one electron transport chain agent which may be an electron transport chain inhibitor and/or an electron transport chain decoupling agent are provided as a nucleic acid stabilization reagent, which includes more than one inhibiting or decoupling agents targeting different portions of the intracellular machinery for production and degradation of nucleic acids of the biological cell. The nucleic acids of the stabilized biological cell are stabilized upon treatment with the stabilization reagent including at least the at least one irreversible protein translation inhibitor; at least one ribonucleic acid transcription inhibitor; and at least one electron transport chain agent which may be an electron transport chain inhibitor and/or an electron transport chain decoupling agent. The electron transport chain agent may be an electron transport chain inhibitor and/or it may be an electron transport decoupling agent. In some embodiments, the stabilization reagent may further include a second protein translation inhibitor, different from the first irreversible protein translation inhibitor. The second protein translation inhibitor may be a reversible inhibitor. The irreversible protein translation inhibitor, ribonucleic acid transcription inhibitor, electron transport chain agent, and, optionally, second protein translation inhibitor may be any suitable inhibitor or electron transport chain agent as described herein and may be selected independently in any combination. The stabilization reagent may contain any of the additional components (e.g., protease inhibitors, RNase inhibitor, buffer, etc.) described herein, selected independently and in any combination. In some embodiments, the stabilization reagent does not contain a RNase inhibitor.

The biological cell is contacted with the stabilization reagent including at least the at least one irreversible protein translation inhibitor; at least one ribonucleic acid transcription inhibitor; and at least one electron transport chain agent which may be an electron transport chain inhibitor and/or an electron transport chain decoupling agent. The contact may be made by adding a pre-made solution of some or all of the components of the stabilization reagent (e.g., a master mix) to a container (e.g., a tube, well, chamber, incubation chamber) that contains the biological cell. In other embodiments, contact with the biological cell may be performed by adding a plurality of solutions, each with less than all of the components (e.g., some components are present in different solutions to be pipetted in individually) at the initiation of the stabilizing reaction. Accordingly, in some embodiments, contacting the biological cell with each component of the stabilization reagent may be performed simultaneously. In other embodiments, contacting the biological cell may be performed sequentially with subsets of the components of the stabilization reagent. The concentration of components of the pre-made solutions may be about 1×, 2×, 5×, 10×, 20×, 50×, 100× or about 1000× the final concentration needed in the stabilizing reaction itself.

In any of the methods described herein, the at least one irreversible protein translation inhibitor may be present at a concentration from about 1.0 micromolar to about 100 millimolar; about 1.0 micromolar to about 50 millimolar; about 1.0 micromolar to about 5 millimolar; about 5 micromolar to about 15 millimolar; about 5 micromolar to about 10 millimolar; about 0.1 millimolar to about 5 millimolar; or any value in between these ranges.

In any of the methods described herein, the ribonucleic acid transcription inhibitor may be present in a concentration at a range from about 10 nanomolar to about 50 millimolar; about 0.01 micromolar to about 50 millimolar; about 0.1 micromolar to about 500 micromolar; about 0.1 micromolar to about 50 micromolar; or any value in between these ranges.

In any of the methods described herein, the electron transport chain agent may be present in a concentration at a range from about 0.1 micromolar to about 100 millimolar; about 10 micromolar to about 50 millimolar; about 0.3 millimolar to about 25 millimolar; about 0.3 millimolar to about 15 millimolar; about 0.5 millimolar to about 10 millimolar; about 1 millimolar to about 5 millimolar; or any value in between these ranges.

In any of the methods described herein, the second protein translation inhibitor may be present in a concentration at a range from about 1.0 micromolar to about 100 millimolar; about 1.0 micromolar to about 50 millimolar; about 1.0 micromolar to about 5 millimolar; about 5 micromolar to about 15 millimolar; about 5 micromolar to about 10 millimolar; about 0.1 millimolar to about 5 millimolar; or any value in between these ranges.

The step of contacting the biological cell with the stabilization reagent including at least the at least one irreversible protein translation inhibitor; at least one ribonucleic acid transcription inhibitor; and at least one electron transport chain agent which may be an electron transport chain inhibitor and/or an electron transport chain decoupling agent may be performed for a period of about 5 min, 10 min, 15 min, 20 min, 30 min, 45 min, 1 h, 2 h, 4 h or more. In some embodiments, the period of contact may be in the range of about 5 min to about 1 h, about 5 min to about 45 min, about 5 min to about 30 min, or about 5 min to about 15 min. The step of contacting may be performed at about 38° C., 37° C., 35° C., 30° C., 25° C., 20° C., 15° C., 10° C., 5° C., or about 0° C.

After contacting the biological cell with the stabilization reagent, the population of nucleic acids may now be stabilized and the biological cell is converted to a stabilized biological cell, e.g., intracellular processes of transcription and translation may be disrupted. The cell may then be stored for any desired period of time, e.g., a few hours to days or even longer. A stabilized cell may be stored for about 2 h, 5 h, 8 h, 14 h, 20 h, 1 day, 2 days, 3 days, 4 days, 5 days, 6 days, 7 days, 2 weeks, 3 weeks, 4 weeks, months, or any time therebetween. In some embodiments, the stabilized cell may be stored for more than about 2 h and less than about 1 week; more than about 8 h and less than about 2 weeks; more than about 8 h and less than about 1 week; or more than about 14 h and less than about 5 days. In some embodiments, a stabilized cell may be stored for about 1 h to about 24 h, about 6 h to about 18 h, about 12 h to about 24 h, about 18 h to about 30 h, about 24 h to about 36 h, about 30 h to about 42 h, about 36 h to about 48 h, about 42 h to about 54 h, about 48 to about 60 h, or any length of time within any of these ranges. It may be desirable to store the stabilized cell at a temperature lower than typical room temperature, e.g., 20° C. In some embodiments, the cell may be stored at a temperature in the range of about 0° C. to about 10° C. (e.g., about 0° C. to about 5° C. or about 2° C. to about 5° C.). In other embodiments, the cell may be stored at a temperature in the range of about −30° C. to about −25° C., about −30° C. to about 0° C., about −25° C. to about 0° C., about −25° C. to about 4° C., or any selected temperature in these ranges.

The method of stabilizing nucleic acids may further include a step of lysing the stabilized biological cell by contacting the stabilized biological cell with a lysis reagent. The lysis reagent may be configured to isolate a population of DNA or a population of RNA. The lysis reagent for isolating DNA may further be configured to isolate all DNA, selectively isolate genomic DNA (gDNA) or mitochondrial DNA (mDNA). The lysis reagent for isolating RNA may be configured to isolate all RNA or preferentially only one type of RNA, which may be messenger RNA (mRNA), ribosomal RNA (rRNA) or transfer RNA (tRNA). In some embodiments, the stabilized biological cell may be washed with media or aqueous wash solution to remove excess stabilization reagent and other soluble materials in the medium surrounding the biological cell, before treating the stabilized biological cell with the lysis reagent. In some embodiments, the step of lysing the stabilized biological cell may further include additional manipulations to prepare the lysed biological cell for retrieval of the desired nucleic acid from the lysed biological cell.

The method of stabilizing nucleic acids may further include isolating at least a portion of the stabilized population of nucleic acids released from the lysed stabilized biological cell. Isolating may be performed by precipitation, solvent extraction, specific capture onto matrices or beads having oligonucleotide capture ligands, or affinity capture onto charge capture matrices.

The method may further include analyzing at least a portion of the population of nucleic acids isolated from the lysed stabilized biological cell. All classes of the population of isolated nucleic acid may be analyzed or only a selected class of nucleic acid may be analyzed. Any of gDNA, mDNA, mRNA, rRNA, and/or tRNA may be analyzed. Analysis may include sequencing (e.g., electrophoretic, Next-Gen sequencing which may include sequencing by synthesis, single molecule, ion semiconductor, pyrosequecing, nanopore sequencing and the like), hybridization experiments (including but not limited to in-situ hybridization, FISH, qPCR, dPCR, TaqMan® (ThermoFisher Scientific), molecular beacon and other fluorescent probe analyses), footprinting, capture onto arrays, and gel electrophoresis. In one particular embodiment, mRNA is analyzed by sequencing to perform transcriptome analysis. Transcriptome analysis can be useful to examine global gene expression changes in a biological cell, which may be useful for identifying pathological cell states and/or exploring options to address the pathology.

In some embodiments, these methods may include manipulating a biological cell within a microfluidic environment. Therefore, a method is provided herein for stabilizing a population of nucleic acids in a biological cell within a microfluidic device. The microfluidic device may be configured like any of the microfluidic devices described herein (e.g., devices 100, 200, 240, 290, any of which may include a DEP configuration and/or an electrowetting configuration as described below), which may be optically actuated. The microfluidic device may have an enclosure, where the enclosure includes a flow region configured to contain a fluidic medium; and at least one chamber configured to contain the fluidic medium, where the chamber is fluidically connected to said flow region. The biological cell may be disposed within the microfluidic device, and may further be disposed within the at least one chamber within the enclosure. The biological cell may be introduced into the microfluidic device using a dielectrophoretic force (DEP). Further, when the biological cell is introduced into the at least one chamber within the enclosure of the microfluidic device, the step of disposing within the chamber may be performed using a DEP force. The cell may be contacted with at least one irreversible protein translation inhibitor; at least one ribonucleic acid transcription inhibitor; and at least one electron transport chain agent comprising an electron transport chain inhibitor and/or an electron transport chain decoupling agent, wherein the contacting is performed for a period of time sufficient to stabilize the population of nucleic acids. A stabilization reagent including the at least one irreversible protein translation inhibitor; at least one ribonucleic acid transcription inhibitor; and at least one electron transport chain agent comprising an electron transport chain inhibitor and/or an electron transport chain decoupling agent may be used in the step of contacting the biological cell and may be any embodiment of the stabilization reagent described herein. The method may further include any of the steps described above for the method of stabilizing a biological cell outside of a microfluidic device.

In some embodiments, the chamber within the enclosure may be a sequestration pen having an isolation region and a connection region fluidically connecting the isolation region to the flow region (e.g. a microfluidic channel), with the isolation and connection regions configured such that components of the medium are exchanged between the flow region and the isolation region of the sequestration pen substantially only by diffusion. In some embodiments, the biological cell may be disposed within the isolation region of a sequestration pen of the microfluidic device. The stabilization reagent may be flowed into the flow region (which may be a channel) of the microfluidic device, and it subsequently may contact the biological cell by diffusing into the chamber (or, if the chamber is a sequestration pen, by diffusing into the isolation region of the sequestration pen).

The step of contacting the biological cell with the stabilization reagent including at least the at least one irreversible protein translation inhibitor; at least one ribonucleic acid transcription inhibitor; and at least one electron transport chain agent which may be an electron transport chain inhibitor and/or an electron transport chain decoupling agent may be performed for a period of about 5 min, 10 min, 15 min, 20 min, 30 min, 45 min, 1 h, 2 h, 4 h or more. In some embodiments, the period of contact may be in the range of about 5 min to about 1 h, about 5 min to about 45 min, about 5 min to about 30 min, or about 5 min to about 15 min. The step of contacting may be performed at about 38° C., 37° C., 35° C., 30° C., 25° C., 20° C., 15° C., 10° C., 5° C., or about 0° C.

The methods may include storing the stabilized biological cell for a period of time. The cell may be stored within the microfluidic device, e.g., the stabilized cell is not moved from the chamber (or the isolation region of a sequestration pen) during storage. Thus, the entire microfluidic device may be stored. The cell may be stored within the microfluidic device for about 2 h, 5 h, 8 h, 14 h, 20 h, 1 day, 2 days, 3 days 4 days, 5 days, 6 days, 7 days, 2 weeks, 3 weeks, 4 weeks, months, or any time therebetween. In some embodiments, a stabilized cell may be stored for about 1 h to about 24 h, about 6 h to about 18 h, about 12 h to about 24 h, about 18 h to about 30 h, about 24 h to about 36 h, about 30 h to about 42 h, about 36 h to about 48 h, about 42 h to about 54 h, about 48 to about 60 h, or any length of time within any of these ranges. It may be desirable to store the stabilized cell onboard the microfluidic device at a temperature lower than typical room temperature, e.g., 20° C. In some embodiments, the cell may be stored within the microfluidic device at a temperature in the range of about 0° C. to about 4° C. 0° C. to about 10° C. (e.g., about 0° C. to about 5° C. or about 2° C. to about 5° C.). In other embodiments, the cell may be stored at a temperature in the range of about −30° C. to about −25° C., about −30° C. to about 0° C., about −25° C. to about 0° C., about −25° C. to about 4° C., or any selected temperature in these ranges.

The method of stabilizing nucleic acid in a biological cell within a microfluidic device may further include lysing the stabilized biological cell. For example, the stabilized biological cell may be lysed by contacting the biological cell with a lysis reagent. The stabilized biological cell may be contacted with the lysis reagent within the microfluidic device or outside of the microfluidic device (e.g., after exporting the stabilized biological cell from the microfluidic device). The lysis reagent for isolating DNA may further be configured to isolate all DNA, selectively isolate genomic DNA (gDNA) or mitochondrial DNA (mDNA). The lysis reagent for isolating RNA may be configured to isolate all RNA or preferentially only one type of RNA, which may be messenger RNA (mRNA), ribosomal RNA (rRNA) or transfer RNA (tRNA). Contact of the lysis reagent with the stabilized biological cell may include flowing the lysis reagent into the flow region of the microfluidic device (which may be a channel). Thus, the lysis reagent may contact the biological cell by diffusing from the flow region into the chamber (or, if the chamber is a sequestration pen, by diffusing into the isolation region of the sequestration pen). The stabilized biological cell may be washed to remove excess stabilization reagents or other components of the medium surrounding the stabilized cell within the chamber (or isolation region of a sequestration pen) before flowing in the lysis reagent into the flow region of the microfluidic device. Washing may be accomplished by flowing wash solution or buffer into and/or through the flow region (channel) of the microfluidic device, whereupon the excess stabilization reagent and/or other components of the medium surrounding the cell may exchange by diffusion into the medium in the flow region (channel) thereby removing it from the environment surrounding the stabilized cell. In some embodiments, the step of lysing the stabilized biological cell may further include additional manipulations to prepare the lysed biological cell for retrieval of the desired stabilized population of nucleic acid from the lysed biological cell. Alternatively, the stabilized biological cell may be exported from the microfluidic device into the wash solution or buffer. Exportation of the stabilized biological cell may be performed using a dielectrophoretic force. The dielectrophoretic force may be optically actuated.

The methods of stabilizing nucleic acid within a biological cell within a microfluidic device may further include isolating at least a portion of the stabilized population of nucleic acids released from the lysed biological cell. Isolation of the stabilized nucleic acid may be accomplished by capturing the released population of stabilized nucleic acid to a capture matrix (including but not limited to a capture oligonucleotide on a bead or capture oligonucleotides, which may be primers, printed onto the surface of the microfluidic device). In embodiments in which the stabilized biological cell is lysed within the microfluidic device, the released stabilized nucleic acid may be captured within the microfluidic device. For example, in embodiments in which the microfluidic device includes a DEP configuration, the capture matrix (e.g., beads) can be located within the same chamber/sequestration pen as the stabilized biological cell when the cell is being lysed or, alternatively, the capture matrix can be moved into the chamber/sequestration pen after the stabilized biological cell is lysed. The capture matrix may be disposed into the chamber/sequestration pen with the stabilized/lysed biological cell by a dielectrophoretic force, which, in some embodiments, may be optically actuated. In embodiments in which the microfluidic device includes an electro-wetting configuration (e. g., a opto-electrowetting configuration), isolation of the nucleic acids of the lysed cell may be accomplished by introducing the capture matrix into a droplet of aqueous medium encompassing the nucleic acid (e.g., by merging a droplet containing the capture matrix with the droplet encompassing the released nucleic acid); by moving the droplet of aqueous medium encompassing the released nucleic acids to another region on the microfluidic device where the capture matrix is located or by exporting the droplet out of the microfluidic device for further processing. When the droplet of aqueous medium encompassing the released nucleic acids is moved to another region on the microfluidic device to be captured, the released nucleic acids may be captured by capture matrices such as capture beads or the released nucleic acids may be captured by capture oligonucleotides, which may be primers, which may be immobilized (e.g., printed) to the surface of the microfluidic device. Printed primers may be located within the region where lysing has been performed or in another region of the microfluidic device). Alternatively, nucleic acid may be isolated by moving a droplet of aqueous medium encompassing beads capturing the released nucleic acids to another region of the microfluidic device or by exporting the droplet containing the beads capturing the released nucleic acids out of the microfluidic device.

The method may further include analyzing at least one class of nucleic acid from the at least a portion of the population of stabilized nucleic acids released from the lysed biological cell. Analysis may be performed off-chip, by exporting the nucleic acids or capture matrix to which the nucleic acids are bound as described or may be performed on-chip in another region of the microfluidic device. On-chip analysis may include hybridization assays or other fluorescent detection methods (e.g., in-situ hybridization, FISH, qPCR, dPCR, TaqMan, molecular beacons and the like).

Analysis performed outside of the microfluidic device may include, but is not limited to sequencing, hybridization experiments (including but not limited to in-situ hybridization, FISH, qPCR, dPCR, TaqMan® (ThermoFisher Scientific), molecular beacon and other fluorescent probe analyses), footprinting, capture onto arrays, and gel electrophoresis. In some embodiments, mRNA is analyzed by sequencing to perform transcriptome analysis.

Cells. The biological cell may be any kind of biological cell, prokaryote or eukaryote. In some embodiments, the biological cell may be mammalian. The mammalian biological cell may be human, primate, porcine, murine, rat, canine or the like. The biological cell may be derived from a subject having a cellular disorder, including a proliferative, infectious, autoimmune, and/or endocrine disorder. The biological cell may be derived from a normal subject or from a genetically engineered subject. The biological cell may be derived from a hybridoma, cultured cell sample, or a cell line, such as a Chinese Hamster Ovary (CHO) cell line. Alternatively, the biological cell may be derived from blood, urine, tears, sweat or feces of a subject, in particular, a human subject. In yet other embodiments, the biological cell may be derived from a tissue sample excised from the subject, including but not limited to a resected tumor sample and a biopsy sample, a fine needle aspirate and a formalin-fixed paraffin embedded (FFPE) tissue sample. The biological cell may be an immunological cell (such as a leukocyte, a T cell, a B cell, a macrophage, Natural Killer cell, dendritic cell, or the like), breast cell, pancreatic cell, prostate cell, lung cell, or a tumor cell, such as a circulating tumor cell, of any type including but not limited to melanoma, breast, etc.

Compositions. In some embodiments, compositions are provided. A composition may include a biological cell and a stabilization reagent as described herein. The stabilization reagent may include at least one irreversible protein translation inhibitor, at least one ribonucleic acid transcription inhibitor, and at least one electron transport chain agent. In some embodiments, the stabilization reagent may further include a second protein translation inhibitor. The at least one irreversible protein translation inhibitor, at least one ribonucleic acid transcription inhibitor, at least one electron transport chain agent, and, optionally, the second protein translation inhibitor may be any suitable species of each class as described above. The composition may further include any of the additionally described components of the stabilization reagent (e.g., protease inhibitor, RNase inhibitor, buffer, and the like.

Kits. In some embodiments, a kit for stabilizing a population of nucleic acid within a cell may be provided. The kit may include a stabilization reagent including at least one protein translation inhibitor; at least one ribonucleic acid transcription inhibitor; and at least one electron transport chain agent chosen from an electron transport chain inhibitor and an electron transport chain decoupling agent. The at least first protein translation inhibitor may be an irreversible inhibitor.

In some embodiments, the kit may provide a stabilization reagent to stabilize deoxynucleic acids for storage and subsequent DNA isolation. In other embodiments, the kit may provide a stabilization reagent which will stabilize ribonucleic acid (RNA) for storage and subsequent isolation. In some embodiments, the kit may provide a stabilization reagent to stabilize messenger RNA (mRNA) for storage and subsequent isolation. The stabilization reagent may be any stabilization reagent as described herein.

In various embodiments of the kit, the at least one protein translation inhibitor (e.g., irreversible) may be cell membrane permeable. The irreversible protein translation inhibitor may be chosen from aminoglycoside antibiotics, D-galactosamine, and emetine. In some embodiments, the irreversible protein translation inhibitor may be emetine.

The at least one ribonucleic acid transcription inhibitor of the kit may be cell membrane permeable. The ribonucleic acid transcription inhibitor may be chosen from CDK9 inhibitors, aurethricin, thiolutin, amanitin, and/or triptolide. In various embodiments, the ribonucleic acid transcription inhibitor may be an irreversible inhibitor. In some embodiments, the ribonucleic acid transcription inhibitor may be triptolide.

The at least one electron transport chain agent of the kit may be an electron transport chain inhibitor or an electron transport chain decoupling agent. The electron transport chain agent may have reversible activity against its target. In some other embodiments, the electron transport chain agent may have irreversible activity against its target. The electron transport chain agent may be cell membrane soluble. The electron transport chain agent may be any suitable electron transport chain agent including, but not limited to any of the electron transport chain agents described above. In some embodiments, the electron transport chain agent may be an electron transport chain inhibitor. In some embodiments, the electron transport chain agent may be sodium azide. In some embodiments, more than one electron transport chain agent may be included in the kit.

The kit may further include a second protein translation inhibitor. The second protein translation inhibitor is different from the first protein translation inhibitor. In some embodiments, the second protein translation inhibitor may be any suitable protein translation inhibitor. The second protein translation inhibitor may be an irreversible inhibitor. In some embodiments, the second protein translation inhibitor may be a reversible protein translation inhibitor. The second protein translation inhibitor may be fast acting, e.g., the effects of the inhibition are seen within a period of about 1, 2, 3, 5, 10 min to about 30 min. The second protein translation inhibitor may be cell membrane permeable. The second protein translation inhibitor may be chosen from diazooxide, a glutarimide antibiotic, and an ipecac alkaloid. In various embodiments, the second protein translation inhibitor may be cycloheximide.

In various embodiments of the kit, some or all of the components of the stabilization reagent may be provided as a pre-made solution (e.g., a master mix) including more than one of the at least one irreversible protein translation inhibitor, the at least one ribonucleic acid transcription inhibitor, and the at least one electron transport chain agent of the stabilization reagent. In some embodiments, the master mix may include the at least one irreversible protein translation inhibitor, the at least one ribonucleic acid transcription inhibitor, and the at least one electron transport chain agent of the stabilization reagent. The master mix may further include any other component of any stabilization reagent as described herein. The concentration of the components of the stabilization reagent in the master mix may be about 1×, 2×, 5×, 10×, 20×, 50×, 100× or about 1000× the final concentration needed in the stabilizing reaction itself.

Other components of the kit. In various embodiments, the kit does not include a RNase inhibitor. The kit may further include a protease inhibitor. The protease inhibitor may be incorporated within the stabilization reagent or may be provided as a stand-alone component of the kit. The protease inhibitor may be a cysteine protease, a serine protease inhibitor, or a metalloprotease inhibitor. The protease inhibitor may be any suitable protease inhibitor, including but not limited to any of the protease inhibitors described above.

Lysis buffer. The kit further may further include a lysis buffer. The lysis buffer is not included in the stabilization reagent or any of the solutions comprising the stabilization reagent. The lysis buffer may be provided in a separate container from the other components of the kit. The lysis buffer may be configured to isolate genomic or mitochondrial DNA. In other embodiments, the lysis buffer may be designed to isolate total RNA or a subset of RNA. The lysis buffer may be denaturing. The lysis buffer may include a detergent which may be non-ionic or zwitterionic. In some embodiments, an ionic detergent may be used, for example, when isolating DNA. A suitable lysis buffer detergent may include, but is not limited to, sodium dodecyl sulfate (SDS), Tris(hydroxymethyl)aminomethane hydrochloride (Tris-HCl), sodium deoxycholate, 3-[(3-cholamidopropyl)dimethylammonio]-1-propanesulfonate (CHAPS), polysorbate 20, polyoxyethylene sorbitan monolaurate, PEG (20) sorbitan monolaurate (Tween 20), nonyl phenoxypolyethoxylethanol (NP40), octyl phenoxypolyethoxylethanol (Nonidet P-40), or Polyethylene glycol tert-octylphenyl ether (Triton™ X-100). In some embodiments, the lysis buffer detergent may include SDS.

The lysis buffer may further include chelating agents such as EDTA. The lysis buffer may include protease inhibitors, and may further include a mixture of protease inhibitors. In some embodiments, the lysis buffer may include one or more phosphatase inhibitors.

RNA isolation. Lysis buffers may be buffered between pH 7-8 when RNA is being isolated. The lysis buffer for RNA may include phenol (to prevent RNA degradation) and guanidinium isothiocyanate (a chaotrope which also denatures RNase and DNase enzymes). The lysis buffer may include one or more RNase inhibitors.

In some embodiments of the kit, the at least one irreversible protein translation inhibitor, the ribonucleic acid transcription inhibitor, and the electron transport chain agent may be provided in a solution. Each of the at least first irreversible protein translation inhibitor, the ribonucleic acid transcription inhibitor, and the electron transport chain agent may be provided either as a separate solution in separate containers or may be provided as a mixture of one or more of the components of the kit, in any combination. The kit may further include one or more protease inhibitors, which may be any suitable protease inhibitor (including but not limited to the protease inhibitors described herein). The kit may further include one or more RNase inhibitors, which may be any suitable RNase inhibitor (including but not limited to the RNase inhibitors described herein). In some embodiments, all of the components of the stabilization reagent are provided in the kit as a single solution. When any or all of the components of the stabilization reagent are provided as solution(s), concentration of the components may be at 1×, 2×, 5×, 10×, 20×, 50×, 100× or about 1000× of the final concentration to be used for stabilizing the nucleic acids of the cell, therefore permitting dilution of the solution(s) of the kit prior to addition to the biological cell.

In various embodiments of the kit, the at least one irreversible protein translation inhibitor may be present within the solution at a concentration from about 1.0 micromolar to about 2 M; about 1.0 micromolar to about 0.5 M; about 1.0 micromolar to about 500 millimolar; about 1.0 micromolar to about 250 millimolar; about 0.1 millimolar to about 150 millimolar; about 0.1 millimolar to about 50 millimolar; about 1 millimolar to about 100 millimolar; about 1 millimolar to about 50 millimolar, about 10 millimolar to about 1 molar, or any value in between these ranges.

In various embodiments of the kit, the at least one ribonucleic acid transcription inhibitor is present within the solution in a concentration from about 10 nanomolar to about 500 millimolar; about 0.01 micromolar to about 500 millimolar; about 0.1 micromolar to about 50 millimolar; about 0.1 micromolar to about 5 millimolar; about 0.1 micromolar to about 500 micromolar; or any value in between these ranges.

In various embodiments of the kit, the at least one electron transport chain agent is present in a concentration of about 0.1 micromolar to about 5 M; about 0.1 micromolar to about 1 M; about 0.1 micromolar to about 500 millimolar; about 0.3 millimolar to about 250 millimolar; about 0.3 millimolar to about 150 millimolar; about 0.5 millimolar to about 100 millimolar; about 1.0 micromolar to about 500 millimolar; about 1.0 millimolar to about 100 millimolar; or any value in between these ranges.

In various embodiments of the kit, the second protein translation inhibitor may be present within the solution in a concentration from about 1.0 micromolar to about 2 M; about 1.0 micromolar to about 0.5 M; about 1.0 micromolar to about 500 millimolar; about 1.0 micromolar to about 250 millimolar; about 0.1 millimolar to about 150 millimolar; about 0.1 millimolar to about 50 millimolar; about 1 millimolar to about 100 millimolar; about 1 millimolar to about 50 millimolar, about 10 millimolar to about 1 molar, or any value in between these ranges.

Microfluidic devices and systems for operating and observing such devices. FIG. 1A illustrates an example of a microfluidic device 100 and a system 150 which can be used for maintaining, expanding and assaying micro-objects according to embodiments of the disclosure. A perspective view of the microfluidic device 100 is shown having a partial cut-away of its cover 110 to provide a partial view into the microfluidic device 100. The microfluidic device 100 generally comprises a microfluidic circuit 120 comprising a flow path 106 through which a fluidic medium 180 can flow, optionally carrying one or more micro-objects (not shown) into and/or through the microfluidic circuit 120. Although a single microfluidic circuit 120 is illustrated in FIG. 1A, suitable microfluidic devices can include a plurality (e.g., 2 or 3) of such microfluidic circuits. Regardless, the microfluidic device 100 can be configured to be a nanofluidic device. As illustrated in FIG. 1A, the microfluidic circuit 120 may include a plurality of microfluidic sequestration pens 124, 126, 128, and 130, where each sequestration pens may have one or more openings in fluidic communication with flow path 106. In some embodiments of the device of FIG. 1A, the sequestration pens may have only a single opening in fluidic communication with the flow path 106. As discussed further below, the microfluidic sequestration pens comprise various features and structures that have been optimized for retaining micro-objects in the microfluidic device, such as microfluidic device 100, even when a medium 180 is flowing through the flow path 106. Before turning to the foregoing, however, a brief description of microfluidic device 100 and system 150 is provided.

As generally illustrated in FIG. 1A, the microfluidic circuit 120 is defined by an enclosure 102. Although the enclosure 102 can be physically structured in different configurations, in the example shown in FIG. 1A the enclosure 102 is depicted as comprising a support structure 104 (e.g., a base), a microfluidic circuit structure 108, and a cover 110. The support structure 104, microfluidic circuit structure 108, and cover 110 can be attached to each other. For example, the microfluidic circuit structure 108 can be disposed on an inner surface 109 of the support structure 104, and the cover 110 can be disposed over the microfluidic circuit structure 108. Together with the support structure 104 and cover 110, the microfluidic circuit structure 108 can define the elements of the microfluidic circuit 120.

The support structure 104 can be at the bottom and the cover 110 at the top of the microfluidic circuit 120 as illustrated in FIG. 1A. Alternatively, the support structure 104 and the cover 110 can be configured in other orientations. For example, the support structure 104 can be at the top and the cover 110 at the bottom of the microfluidic circuit 120. Regardless, there can be one or more ports 107 each comprising a passage into or out of the enclosure 102. Examples of a passage include a valve, a gate, a pass-through hole, or the like. As illustrated, port 107 is a pass-through hole created by a gap in the microfluidic circuit structure 108. However, the port 107 can be situated in other components of the enclosure 102, such as the cover 110. Only one port 107 is illustrated in FIG. 1A but the microfluidic circuit 120 can have two or more ports 107. For example, there can be a first port 107 that functions as an inlet for fluid entering the microfluidic circuit 120, and there can be a second port 107 that functions as an outlet for fluid exiting the microfluidic circuit 120. Whether a port 107 function as an inlet or an outlet can depend upon the direction that fluid flows through flow path 106.

The support structure 104 can comprise one or more electrodes (not shown) and a substrate or a plurality of interconnected substrates. For example, the support structure 104 can comprise one or more semiconductor substrates, each of which is electrically connected to an electrode (e.g., all or a subset of the semiconductor substrates can be electrically connected to a single electrode). The support structure 104 can further comprise a printed circuit board assembly ("PCBA"). For example, the semiconductor substrate(s) can be mounted on a PCBA.

The microfluidic circuit structure 108 can define circuit elements of the microfluidic circuit 120. Such circuit elements can comprise spaces or regions that can be fluidly interconnected when microfluidic circuit 120 is filled with fluid, such as flow regions (which may include or be one or more flow channels), chambers, pens, traps, and the like. In the microfluidic circuit 120 illustrated in FIG. 1A, the microfluidic circuit structure 108 comprises a frame 114 and a microfluidic circuit material 116. The frame 114 can partially or completely enclose the microfluidic circuit material 116. The frame 114 can be, for example, a relatively rigid structure substantially surrounding the microfluidic circuit material 116. For example, the frame 114 can comprise a metal material.

The microfluidic circuit material 116 can be patterned with cavities or the like to define circuit elements and interconnections of the microfluidic circuit 120. The microfluidic circuit material 116 can comprise a flexible material, such as a flexible polymer (e.g. rubber, plastic, elastomer, silicone, polydimethylsiloxane ("PDMS"), or the like), which can be gas permeable. Other examples of materials that can compose microfluidic circuit material 116 include molded glass, an etchable material such as silicone (e.g. photo-patternable silicone or "PPS"), photo-resist (e.g., SU8), or the like. In some embodiments, such materials—and thus the microfluidic circuit material 116—can be rigid and/or substantially impermeable to gas. Regardless, microfluidic circuit material 116 can be disposed on the support structure 104 and inside the frame 114.

The cover 110 can be an integral part of the frame 114 and/or the microfluidic circuit material 116. Alternatively, the cover 110 can be a structurally distinct element, as illustrated in FIG. 1A. The cover 110 can comprise the same or different materials than the frame 114 and/or the microfluidic circuit material 116. Similarly, the support structure 104 can be a separate structure from the frame 114 or microfluidic circuit material 116 as illustrated, or an integral part of the frame 114 or microfluidic circuit material 116. Likewise, the frame 114 and microfluidic circuit material 116 can be separate structures as shown in FIG. 1A or integral portions of the same structure.

In some embodiments, the cover 110 can comprise a rigid material. The rigid material may be glass or a material with similar properties. In some embodiments, the cover 110 can comprise a deformable material. The deformable material can be a polymer, such as PDMS. In some embodiments, the cover 110 can comprise both rigid and deformable materials. For example, one or more portions of cover 110 (e.g., one or more portions positioned over sequestration pens 124, 126, 128, 130) can comprise a deformable material that interfaces with rigid materials of the cover 110. In some embodiments, the cover 110 can further include one or more electrodes. The one or more electrodes can comprise a conductive oxide, such as indium-tin-oxide (ITO), which may be coated on glass or a similarly insulating material. Alternatively, the one or more electrodes can be flexible electrodes, such as single-walled nanotubes, multi-walled nanotubes, nanowires, clusters of electrically conductive nanoparticles, or combinations thereof, embedded in a deformable material, such as a polymer (e.g., PDMS). Flexible electrodes that can be used in microfluidic devices have been described, for example, in U.S. 2012/0325665 (Chiou et al.), the contents of which are incorporated herein by reference. In some embodiments, the cover 110 can be modified (e.g., by conditioning all or part of a surface that faces inward toward the microfluidic circuit 120) to support cell adhesion, viability and/or growth. The modification may include a coating of a synthetic or natural polymer. In some embodiments, the cover 110 and/or the support structure 104 can be transparent to light. The cover 110 may also include at least one material that is gas permeable (e.g., PDMS or PPS).

FIG. 1A also shows a system 150 for operating and controlling microfluidic devices, such as microfluidic device 100. System 150 includes an electrical power source 192, an imaging device 194 (incorporated within imaging module 164, where device 194 is not illustrated in FIG. 1A, per se), and a tilting device 190 (part of tilting module 166, where device 190 is not illustrated in FIG. 1A).

The electrical power source 192 can provide electric power to the microfluidic device 100 and/or tilting device 190, providing biasing voltages or currents as needed. The electrical power source 192 can, for example, comprise one or more alternating current (AC) and/or direct current (DC) voltage or current sources. The imaging device 194 (part of imaging module 164, discussed below) can comprise a device, such as a digital camera, for capturing images inside microfluidic circuit 120. In some instances, the imaging device 194 further comprises a detector having a fast frame rate and/or high sensitivity (e.g. for low light applications). The imaging device 194 can also include a mechanism for directing stimulating radiation and/or light beams into the microfluidic circuit 120 and collecting radiation and/or light beams reflected or emitted from the microfluidic circuit 120 (or micro-objects contained therein). The emitted light beams may be in the visible spectrum and may, e.g., include fluorescent emissions. The reflected light beams may include reflected emissions originating from an LED or a wide spectrum lamp, such as a mercury lamp (e.g. a high-pressure mercury lamp) or a Xenon arc lamp. As discussed with respect to FIG. 3B, the imaging device 194 may further include a microscope (or an optical train), which may or may not include an eyepiece.

System 150 further comprises a tilting device 190 (part of tilting module 166, discussed below) configured to rotate a microfluidic device 100 about one or more axes of rotation. In some embodiments, the tilting device 190 is configured to support and/or hold the enclosure 102 comprising the microfluidic circuit 120 about at least one axis such that the microfluidic device 100 (and thus the microfluidic circuit 120) can be held in a level orientation (i.e. at 0° relative to x- and y-axes), a vertical orientation (i.e. at 90° relative to the x-axis and/or the y-axis), or any orientation therebetween. The orientation of the microfluidic device 100 (and the microfluidic circuit 120) relative to an axis is referred to herein as the "tilt" of the microfluidic device 100 (and the microfluidic circuit 120). For example, the tilting device 190 can tilt the microfluidic device 100 at 0.1°, 0.2°, 0.3°, 0.4°, 0.5°, 0.6°, 0.7°, 0.8°, 0.9°, 1°, 2°, 3°, 4°, 5°, 10°, 15°, 20°, 25°, 30°, 35°, 40°, 45°, 50°, 55°, 60°, 65°, 70°, 75°, 80°, 90° relative to the x-axis or any degree therebetween. The level orientation (and thus the x- and y-axes) is defined as normal to a vertical axis defined by the force of gravity. The tilting device can also tilt the microfluidic device 100 (and the microfluidic circuit 120) to any degree greater than 90° relative to the x-axis and/or y-axis, or tilt the microfluidic device 100 (and the microfluidic circuit 120) 180° relative to the x-axis or the y-axis in order to fully invert the microfluidic device 100 (and the microfluidic circuit 120). Similarly, in some embodiments, the tilting device 190 tilts the microfluidic device 100 (and the microfluidic circuit 120) about an axis of rotation defined by flow path 106 or some other portion of microfluidic circuit 120.

In some instances, the microfluidic device 100 is tilted into a vertical orientation such that the flow path 106 is positioned above or below one or more sequestration pens. The term "above" as used herein denotes that the flow path 106 is positioned higher than the one or more sequestration pens on a vertical axis defined by the force of gravity (i.e. an object in a sequestration pen above a flow path 106 would have a higher gravitational potential energy than an object in the flow path). The term "below" as used herein denotes that the flow path 106 is positioned lower than the one or more sequestration pens on a vertical axis defined by the force of gravity (i.e. an object in a sequestration pen below a flow path 106 would have a lower gravitational potential energy than an object in the flow path).

In some instances, the tilting device 190 tilts the microfluidic device 100 about an axis that is parallel to the flow path 106. Moreover, the microfluidic device 100 can be tilted to an angle of less than 90° such that the flow path 106 is located above or below one or more sequestration pens without being located directly above or below the sequestration pens. In other instances, the tilting device 190 tilts the microfluidic device 100 about an axis perpendicular to the flow path 106. In still other instances, the tilting device 190 tilts the microfluidic device 100 about an axis that is neither parallel nor perpendicular to the flow path 106.

System 150 can further include a media source 178. The media source 178 (e.g., a container, reservoir, or the like) can comprise multiple sections or containers, each for holding a different fluidic medium 180. Thus, the media source 178 can be a device that is outside of and separate from the microfluidic device 100, as illustrated in FIG. 1A. Alternatively, the media source 178 can be located in whole or in part inside the enclosure 102 of the microfluidic device 100. For example, the media source 178 can comprise reservoirs that are part of the microfluidic device 100.

FIG. 1A also illustrates simplified block diagram depictions of examples of control and monitoring equipment 152 that constitute part of system 150 and can be utilized in conjunction with a microfluidic device 100. As shown, examples of such control and monitoring equipment 152 include a master controller 154 comprising a media module 160 for controlling the media source 178, a motive module 162 for controlling movement and/or selection of micro-objects (not shown) and/or medium (e.g., droplets of medium) in the microfluidic circuit 120, an imaging module 164 for controlling an imaging device 194 (e.g., a camera, microscope, light source or any combination thereof) for capturing images (e.g., digital images), and a tilting module 166 for controlling a tilting device 190. The control equipment 152 can also include other modules 168 for controlling, monitoring, or performing other functions with respect to the microfluidic device 100. As shown, the equipment 152 can further include a display device 170 and an input/output device 172.

The master controller 154 can comprise a control module 156 and a digital memory 158. The control module 156 can comprise, for example, a digital processor configured to operate in accordance with machine executable instructions (e.g., software, firmware, source code, or the like) stored as non-transitory data or signals in the memory 158. Alternatively, or in addition, the control module 156 can comprise hardwired digital circuitry and/or analog circuitry. The media module 160, motive module 162, imaging module 164, tilting module 166, and/or other modules 168 can be similarly configured. Thus, functions, processes acts, actions, or steps of a process discussed herein as being performed with respect to the microfluidic device 100 or any other microfluidic apparatus can be performed by any one or more of the master controller 154, media module 160, motive module 162, imaging module 164, tilting module 166, and/or other modules 168 configured as discussed above. Similarly, the master controller 154, media module 160, motive module 162, imaging module 164, tilting module 166, and/or other modules 168 may be communicatively coupled to transmit and receive data used in any function, process, act, action or step discussed herein.

The media module 160 controls the media source 178. For example, the media module 160 can control the media source 178 to input a selected fluidic medium 180 into the enclosure 102 (e.g., through an inlet port 107). The media module 160 can also control removal of media from the enclosure 102 (e.g., through an outlet port (not shown)). One or more media can thus be selectively input into and removed from the microfluidic circuit 120. The media module 160 can also control the flow of fluidic medium 180 in the flow path 106 inside the microfluidic circuit 120. For example, in some embodiments media module 160 stops the flow of media 180 in the flow path 106 and through the enclosure 102 prior to the tilting module 166 causing the tilting device 190 to tilt the microfluidic device 100 to a desired angle of incline.

The motive module 162 can be configured to control selection, trapping, and movement of micro-objects (not shown) in the microfluidic circuit 120. As discussed below with respect to FIGS. 1B and 1C, the enclosure 102 can comprise a dielectrophoresis (DEP), optoelectronic tweezers (OET) and/or opto-electrowetting (OEW) configuration (not shown in FIG. 1A), and the motive module 162 can control the activation of electrodes and/or transistors (e.g., phototransistors) to select and move micro-objects (not shown) and/or droplets of medium (not shown) in the flow path 106 and/or sequestration pens 124, 126, 128, 130.

The imaging module 164 can control the imaging device 194. For example, the imaging module 164 can receive and process image data from the imaging device 194. Image data from the imaging device 194 can comprise any type of information captured by the imaging device 194 (e.g., the presence or absence of micro-objects, droplets of medium, accumulation of label, such as fluorescent label, etc.). Using the information captured by the imaging device 194, the imaging module 164 can further calculate the position of objects (e.g., micro-objects, droplets of medium) and/or the rate of motion of such objects within the microfluidic device 100.

The tilting module 166 can control the tilting motions of tilting device 190. Alternatively, or in addition, the tilting module 166 can control the tilting rate and timing to optimize transfer of micro-objects to the one or more sequestration pens via gravitational forces. The tilting module 166 is communicatively coupled with the imaging module 164 to receive data describing the motion of micro-objects and/or droplets of medium in the microfluidic circuit 120. Using this data, the tilting module 166 may adjust the tilt of the microfluidic circuit 120 in order to adjust the rate at which micro-objects and/or droplets of medium move in the microfluidic circuit 120. The tilting module 166 may also use this data to iteratively adjust the position of a micro-object and/or droplet of medium in the microfluidic circuit 120.

In the example shown in FIG. 1A, the microfluidic circuit 120 is illustrated as comprising a microfluidic channel 122 and sequestration pens 124, 126, 128, 130. Each pen comprises an opening to channel 122, but otherwise is enclosed such that the pens can substantially isolate micro-objects inside the pen from fluidic medium 180 and/or micro-objects in the flow path 106 of channel 122 or in other pens. The walls of the sequestration pen extend from the inner surface 109 of the base to the inside surface of the cover 110 to provide enclosure. The opening of the pen to the microfluidic channel 122 is oriented at an angle to the flow 106 of fluidic medium 180 such that flow 106 is not directed into the pens. The flow may be tangential or orthogonal to the plane of the opening of the pen. In some instances, pens 124, 126, 128, 130 are configured to physically corral one or more micro-objects within the microfluidic circuit 120. Sequestration pens in accordance with the present disclosure can comprise various shapes, surfaces and features that are optimized for use with DEP, OET, OEW, fluid flow, and/or gravitational forces, as will be discussed and shown in detail below.

The microfluidic circuit 120 may comprise any number of microfluidic sequestration pens. Although five sequestration pens are shown, microfluidic circuit 120 may have fewer or more sequestration pens. As shown, microfluidic sequestration pens 124, 126, 128, and 130 of microfluidic circuit 120 each comprise differing features and shapes which may provide one or more benefits useful for maintaining, isolating, assaying or culturing biological micro-objects. In some embodiments, the microfluidic circuit 120 comprises a plurality of identical microfluidic sequestration pens.

In the embodiment illustrated in FIG. 1A, a single channel 122 and flow path 106 is shown. However, other embodiments may contain multiple channels 122, each configured to comprise a flow path 106. The microfluidic circuit 120 further comprises an inlet valve or port 107 in fluid communication with the flow path 106 and fluidic medium 180, whereby fluidic medium 180 can access channel 122 via the inlet port 107. In some instances, the flow path 106 comprises a single path. In some instances, the single path is arranged in a zigzag pattern whereby the flow path 106 travels across the microfluidic device 100 two or more times in alternating directions.

In some instances, microfluidic circuit 120 comprises a plurality of parallel channels 122 and flow paths 106, wherein the fluidic medium 180 within each flow path 106 flows in the same direction. In some instances, the fluidic medium within each flow path 106 flows in at least one of a forward or reverse direction. In some instances, a plurality of sequestration pens is configured (e.g., relative to a channel 122) such that the sequestration pens can be loaded with target micro-objects in parallel.

In some embodiments, microfluidic circuit 120 further comprises one or more micro-object traps 132. The traps 132 are generally formed in a wall forming the boundary of a channel 122, and may be positioned opposite an opening of one or more of the microfluidic sequestration pens 124, 126, 128, 130. In some embodiments, the traps 132 are configured to receive or capture a single micro-object from the flow path 106. In some embodiments, the traps 132 are configured to receive or capture a plurality of micro-objects from the flow path 106. In some instances, the traps 132 comprise a volume approximately equal to the volume of a single target micro-object.

The traps 132 may further comprise an opening which is configured to assist the flow of targeted micro-objects into the traps 132. In some instances, the traps 132 comprise an opening having a height and width that is approximately equal to the dimensions of a single target micro-object, whereby larger micro-objects are prevented from entering into the micro-object trap. The traps 132 may further comprise other features configured to assist in retention of targeted micro-objects within the trap 132. In some instances, the trap 132 is aligned with and situated on the opposite side of a channel 122 relative to the opening of a microfluidic sequestration pen, such that upon tilting the microfluidic device 100 about an axis parallel to the microfluidic channel 122, the trapped micro-object exits the trap 132 at a trajectory that causes the micro-object to fall into the opening of the sequestration pen. In some instances, the trap 132 comprises a side passage 134 that is smaller than the target micro-object in order to facilitate flow through the trap 132 and thereby increase the likelihood of capturing a micro-object in the trap 132.

In some embodiments, dielectrophoretic (DEP) forces are applied across the fluidic medium 180 (e.g., in the flow path and/or in the sequestration pens) via one or more electrodes (not shown) to manipulate, transport, separate and sort micro-objects located therein. For example, in some embodiments, DEP forces are applied to one or more portions of microfluidic circuit 120 in order to transfer a single micro-object from the flow path 106 into a desired microfluidic sequestration pen. In some embodiments, DEP forces are used to prevent a micro-object within a sequestration pen (e.g., sequestration pen 124, 126, 128, or 130) from being displaced therefrom. Further, in some embodiments, DEP forces are used to selectively remove a micro-object from a sequestration pen that was previously collected in accordance with the embodiments of the current disclosure. In some embodiments, the DEP forces comprise optoelectronic tweezer (OET) forces.

In other embodiments, optoelectrowetting (OEW) forces are applied to one or more positions in the support structure 104 (and/or the cover 110) of the microfluidic device 100 (e.g., positions helping to define the flow path and/or the sequestration pens) via one or more electrodes (not shown) to manipulate, transport, separate and sort droplets located in the microfluidic circuit 120. For example, in some embodiments, OEW forces are applied to one or more positions in the support structure 104 (and/or the cover 110) in order to transfer a single droplet from the flow path 106 into a desired microfluidic sequestration pen. In some embodiments, OEW forces are used to prevent a droplet within a sequestration pen (e.g., sequestration pen 124, 126, 128, or 130) from being displaced therefrom. Further, in some embodiments, OEW forces are used to selectively remove a droplet from a sequestration pen that was previously collected in accordance with the embodiments of the current disclosure.

In some embodiments, DEP and/or OEW forces are combined with other forces, such as flow and/or gravitational force, so as to manipulate, transport, separate and sort micro-objects and/or droplets within the microfluidic circuit 120. For example, the enclosure 102 can be tilted (e.g., by tilting device 190) to position the flow path 106 and micro-objects located therein above the microfluidic sequestration pens, and the force of gravity can transport the micro-objects and/or droplets into the pens. In some embodiments, the DEP and/or OEW forces can be applied prior to the other forces. In other embodiments, the DEP and/or OEW forces can be applied after the other forces. In still other instances, the DEP and/or OEW forces can be applied at the same time as the other forces or in an alternating manner with the other forces.

Figure 1B:
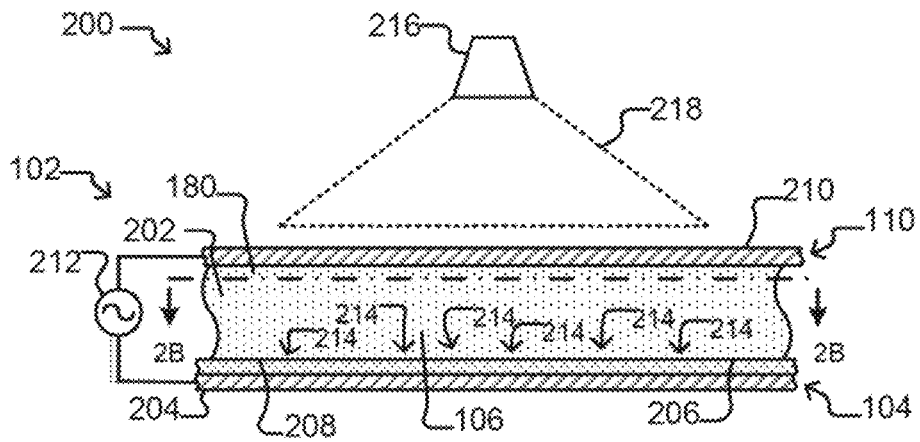
FIGS. 1B and 1C illustrate a microfluidic device according to some embodiments of the disclosure.

FIGS. 1B, 1C, and 2A-2H illustrates various embodiments of microfluidic devices that can be used in the practice of the embodiments of the present disclosure. FIG. 1B depicts an embodiment in which the microfluidic device 200 is configured as an optically-actuated electrokinetic device. A variety of optically-actuated electrokinetic devices are known in the art, including devices having an optoelectronic tweezer (OET) configuration and devices having an optoelectrowetting (OEW) configuration. Examples of suitable OET configurations are illustrated in the following U.S. patent documents, each of which is incorporated herein by reference in its entirety: U.S. Pat. No. RE 44,711 (Wu et al.) (originally issued as U.S. Pat. No. 7,612,355); and U.S. Pat. No. 7,956,339 (Ohta et al.). Examples of OEW configurations are illustrated in U.S. Pat. No. 6,958,132 (Chiou et al.) and U.S. Patent Application Publication No. 2012/0024708 (Chiou et al.), both of which are incorporated by reference herein in their entirety. Yet another example of an optically-actuated electrokinetic device includes a combined OET/OEW configuration, examples of which are shown in U.S. Patent Publication Nos. 20150306598 (Khandros et al.) and 20150306599 (Khandros et al.) and their corresponding PCT Publications WO2015/164846 and WO2015/164847, all of which are incorporated herein by reference in their entirety.

Examples of microfluidic devices having pens in which biological micro-objects can be placed, cultured, and/or monitored have been described, for example, in US 2014/0116881 (application Ser. No. 14/060,117, filed Oct. 22, 2013), US 2015/0151298 (application Ser. No. 14/520,568, filed Oct. 22, 2014), and US 2015/0165436 (application Ser. No. 14/521,447, filed Oct. 22, 2014), each of which is incorporated herein by reference in its entirety. U.S. application Ser. Nos. 14/520,568 and 14/521,447 also describe exemplary methods of analyzing secretions of cells cultured in a microfluidic device. Each of the foregoing applications further describes microfluidic devices configured to produce dielectrophoretic (DEP) forces, such as optoelectronic tweezers (OET) or configured to provide opto-electro wetting (OEW). For example, the optoelectronic tweezers device illustrated in FIG. 2 of US 2014/0116881 is an example of a device that can be utilized in embodiments of the present disclosure to select and move an individual biological micro-object or a group of biological micro-objects.

Microfluidic device motive configurations. As described above, the control and monitoring equipment of the system can comprise a motive module for selecting and moving objects, such as micro-objects or droplets, in the microfluidic circuit of a microfluidic device. The microfluidic device can have a variety of motive configurations, depending upon the type of object being moved and other considerations. For example, a dielectrophoresis (DEP) configuration can be utilized to select and move micro-objects in the microfluidic circuit. Thus, the support structure 104 and/or cover 110 of the microfluidic device 100 can comprise a DEP configuration for selectively inducing DEP forces on micro-objects in a fluidic medium 180 in the microfluidic circuit 120 and thereby select, capture, and/or move individual micro-objects or groups of micro-objects. Alternatively, the support structure 104 and/or cover 110 of the microfluidic device 100 can comprise an electrowetting (EW) configuration for selectively inducing EW forces on droplets in a fluidic medium 180 in the microfluidic circuit 120 and thereby select, capture, and/or move individual droplets or groups of droplets.

Figure 1C:
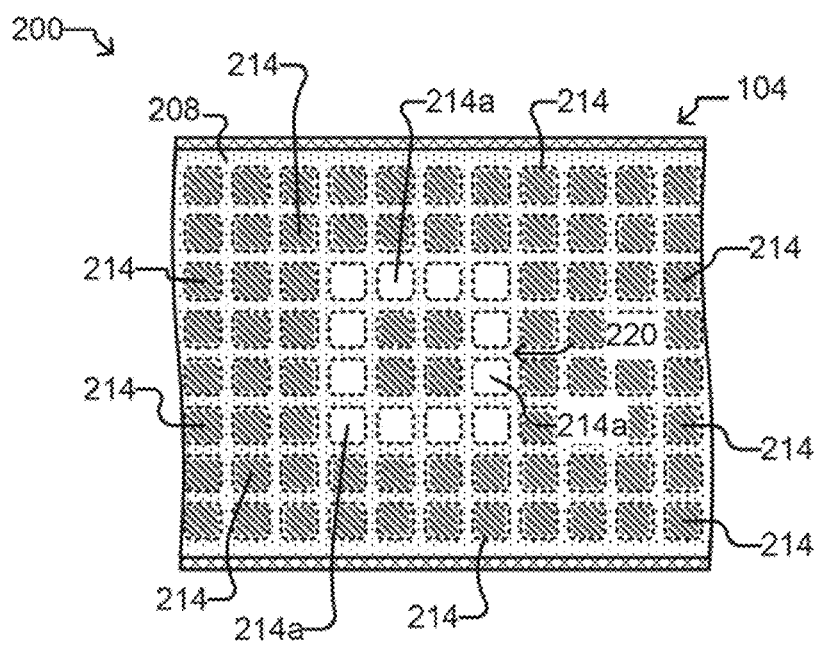

One example of a microfluidic device 200 comprising a DEP configuration is illustrated in FIGS. 1B and 1C. While for purposes of simplicity FIGS. 1B and 1C show a side cross-sectional view and a top cross-sectional view, respectively, of a portion of an enclosure 102 of the microfluidic device 200 having a region/chamber 202, it should be understood that the region/chamber 202 may be part of a fluidic circuit element having a more detailed structure, such as a growth chamber, a sequestration pen, a flow region, or a flow channel. Furthermore, the microfluidic device 200 may include other fluidic circuit elements. For example, the microfluidic device 200 can include a plurality of growth chambers or sequestration pens and/or one or more flow regions or flow channels, such as those described herein with respect to microfluidic device 100. A DEP configuration may be incorporated into any such fluidic circuit elements of the microfluidic device 200, or select portions thereof. It should be further appreciated that any of the above or below described microfluidic device components and system components may be incorporated in and/or used in combination with the microfluidic device 200. For example, system 150 including control and monitoring equipment 152, described above, may be used with microfluidic device 200, including one or more of the media module 160, motive module 162, imaging module 164, tilting module 166, and other modules 168.

As seen in FIG. 1B, the microfluidic device 200 includes a support structure 104 having a bottom electrode 204 and an electrode activation substrate 206 overlying the bottom electrode 204, and a cover 110 having a top electrode 210, with the top electrode 210 spaced apart from the bottom electrode 204. The top electrode 210 and the electrode activation substrate 206 define opposing surfaces of the region/chamber 202. A medium 180 contained in the region/chamber 202 thus provides a resistive connection between the top electrode 210 and the electrode activation substrate 206. A power source 212 configured to be connected to the bottom electrode 204 and the top electrode 210 and create a biasing voltage between the electrodes, as required for the generation of DEP forces in the region/chamber 202, is also shown. The power source 212 can be, for example, an alternating current (AC) power source.

In certain embodiments, the microfluidic device 200 illustrated in FIGS. 1B and 1C can have an optically-actuated DEP configuration. Accordingly, changing patterns of light 218 from the light source 216, which may be controlled by the motive module 162, can selectively activate and deactivate changing patterns of DEP electrodes at regions 214 of the inner surface 208 of the electrode activation substrate 206. (Hereinafter the regions 214 of a microfluidic device having a DEP configuration are referred to as "DEP electrode regions.") As illustrated in FIG. 1C, a light pattern 218 directed onto the inner surface 208 of the electrode activation substrate 206 can illuminate select DEP electrode regions 214a (shown in white) in a pattern, such as a square. The non-illuminated DEP electrode regions 214 (cross-hatched) are hereinafter referred to as "dark" DEP electrode regions 214. The relative electrical impedance through the DEP electrode activation substrate 206 (i.e., from the bottom electrode 204 up to the inner surface 208 of the electrode activation substrate 206 which interfaces with the medium 180 in the flow region 106) is greater than the relative electrical impedance through the medium 180 in the region/chamber 202 (i.e., from the inner surface 208 of the electrode activation substrate 206 to the top electrode 210 of the cover 110) at each dark DEP electrode region 214. An illuminated DEP electrode region 214a, however, exhibits a reduced relative impedance through the electrode activation substrate 206 that is less than the relative impedance through the medium 180 in the region/chamber 202 at each illuminated DEP electrode region 214a.

With the power source 212 activated, the foregoing DEP configuration creates an electric field gradient in the fluidic medium 180 between illuminated DEP electrode regions 214a and adjacent dark DEP electrode regions 214, which in turn creates local DEP forces that attract or repel nearby micro-objects (not shown) in the fluidic medium 180. DEP electrodes that attract or repel micro-objects in the fluidic medium 180 can thus be selectively activated and deactivated at many different such DEP electrode regions 214 at the inner surface 208 of the region/chamber 202 by changing light patterns 218 projected from a light source 216 into the microfluidic device 200. Whether the DEP forces attract or repel nearby micro-objects can depend on such parameters as the frequency of the power source 212 and the dielectric properties of the medium 180 and/or micro-objects (not shown).

The square pattern 220 of illuminated DEP electrode regions 214a illustrated in FIG. 1C is an example only. Any pattern of the DEP electrode regions 214 can be illuminated (and thereby activated) by the pattern of light 218 projected into the microfluidic device 200, and the pattern of illuminated/activated DEP electrode regions 214 can be repeatedly changed by changing or moving the light pattern 218.

In some embodiments, the electrode activation substrate 206 can comprise or consist of a photoconductive material. In such embodiments, the inner surface 208 of the electrode activation substrate 206 can be featureless. For example, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 µm. In such embodiments, the DEP electrode regions 214 can be created anywhere and in any pattern on the inner surface 208 of the electrode activation substrate 206, in accordance with the light pattern 218. The number and pattern of the DEP electrode regions 214 thus need not be fixed, but can correspond to the light pattern 218. Examples of microfluidic devices having a DEP configuration comprising a photoconductive layer such as discussed above have been described, for example, in U.S. Pat. No. RE 44,711 (Wu et al.) (originally issued as U.S. Pat. No. 7,612,355), the entire contents of which are incorporated herein by reference.

In other embodiments, the electrode activation substrate 206 can comprise a substrate comprising a plurality of doped layers, electrically insulating layers (or regions), and electrically conductive layers that form semiconductor integrated circuits, such as is known in semiconductor fields. For example, the electrode activation substrate 206 can comprise a plurality of phototransistors, including, for example, lateral bipolar phototransistors, each phototransistor corresponding to a DEP electrode region 214. Alternatively, the electrode activation substrate 206 can comprise electrodes (e.g., conductive metal electrodes) controlled by phototransistor switches, with each such electrode corresponding to a DEP electrode region 214. The electrode activation substrate 206 can include a pattern of such phototransistors or phototransistor-controlled electrodes. The pattern, for example, can be an array of substantially square phototransistors or phototransistor-controlled electrodes arranged in rows and columns, such as shown in FIG. 2B. Alternatively, the pattern can be an array of substantially hexagonal phototransistors or phototransistor-controlled electrodes that form a hexagonal lattice. Regardless of the pattern, electric circuit elements can form electrical connections between the DEP electrode regions 214 at the inner surface 208 of the electrode activation substrate 206 and the bottom electrode 210, and those electrical connections (i.e., phototransistors or electrodes) can be selectively activated and deactivated by the light pattern 218. When not activated, each electrical connection can have high impedance such that the relative impedance through the electrode activation substrate 206 (i.e., from the bottom electrode 204 to the inner surface 208 of the electrode activation substrate 206 which interfaces with the medium 180 in the region/chamber 202) is greater than the relative impedance through the medium 180 (i.e., from the inner surface 208 of the electrode activation substrate 206 to the top electrode 210 of the cover 110) at the corresponding DEP electrode region 214. When activated by light in the light pattern 218, however, the relative impedance through the electrode activation substrate 206 is less than the relative impedance through the medium 180 at each illuminated DEP electrode region 214, thereby activating the DEP electrode at the corresponding DEP electrode region 214 as discussed above. DEP electrodes that attract or repel micro-objects (not shown) in the medium 180 can thus be selectively activated and deactivated at many different DEP electrode regions 214 at the inner surface 208 of the electrode activation substrate 206 in the region/chamber 202 in a manner determined by the light pattern 218.

Examples of microfluidic devices having electrode activation substrates that comprise phototransistors have been described, for example, in U.S. Pat. No. 7,956,339 (Ohta et al.) (see, e.g., device 300 illustrated in FIGS. 21 and 22, and descriptions thereof), the entire contents of which are incorporated herein by reference. Examples of microfluidic devices having electrode activation substrates that comprise electrodes controlled by phototransistor switches have been described, for example, in U.S. Patent Publication No. 2014/0124370 (Short et al.) (see, e.g., devices 200, 400, 500, 600, and 900 illustrated throughout the drawings, and descriptions thereof), the entire contents of which are incorporated herein by reference.

In some embodiments of a DEP configured microfluidic device, the top electrode 210 is part of a first wall (or cover 110) of the enclosure 102, and the electrode activation substrate 206 and bottom electrode 204 are part of a second wall (or support structure 104) of the enclosure 102. The region/chamber 202 can be between the first wall and the second wall. In other embodiments, the electrode 210 is part of the second wall (or support structure 104) and one or both of the electrode activation substrate 206 and/or the electrode 210 are part of the first wall (or cover 110). Moreover, the light source 216 can alternatively be used to illuminate the enclosure 102 from below.

With the microfluidic device 200 of FIGS. 1B-1C having a DEP configuration, the motive module 162 can select a micro-object (not shown) in the medium 180 in the region/chamber 202 by projecting a light pattern 218 into the microfluidic device 200 to activate a first set of one or more DEP electrodes at DEP electrode regions 214a of the inner surface 208 of the electrode activation substrate 206 in a pattern (e.g., square pattern 220) that surrounds and captures the micro-object. The motive module 162 can then move the in situ-generated captured micro-object by moving the light pattern 218 relative to the microfluidic device 200 to activate a second set of one or more DEP electrodes at DEP electrode regions 214. Alternatively, the microfluidic device 200 can be moved relative to the light pattern 218.

In other embodiments, the microfluidic device 200 can have a DEP configuration that does not rely upon light activation of DEP electrodes at the inner surface 208 of the electrode activation substrate 206. For example, the electrode activation substrate 206 can comprise selectively addressable and energizable electrodes positioned opposite to a surface including at least one electrode (e.g., cover 110). Switches (e.g., transistor switches in a semiconductor substrate) may be selectively opened and closed to activate or inactivate DEP electrodes at DEP electrode regions 214, thereby creating a net DEP force on a micro-object (not shown) in region/chamber 202 in the vicinity of the activated DEP electrodes. Depending on such characteristics as the frequency of the power source 212 and the dielectric properties of the medium (not shown) and/or micro-objects in the region/chamber 202, the DEP force can attract or repel a nearby micro-object. By selectively activating and deactivating a set of DEP electrodes (e.g., at a set of DEP electrodes regions 214 that forms a square pattern 220), one or more micro-objects in region/chamber 202 can be trapped and moved within the region/chamber 202. The motive module 162 in FIG. 1A can control such switches and thus activate and deactivate individual ones of the DEP electrodes to select, trap, and move particular micro-objects (not shown) around the region/chamber 202. Microfluidic devices having a DEP configuration that includes selectively addressable and energizable electrodes are known in the art and have been described, for example, in U.S. Pat. No. 6,294,063 (Becker et al.) and 6,942,776 (Medoro), the entire contents of which are incorporated herein by reference.

As yet another example, the microfluidic device 200 can have an electrowetting (EW) configuration, which can be in place of the DEP configuration or can be located in a portion of the microfluidic device 200 that is separate from the portion which has the DEP configuration. The EW configuration can be an opto-electrowetting configuration (OEW) or an electrowetting on dielectric (EWOD) configuration, both of which are known in the art. In some EW configurations, the support structure 104 has an electrode activation substrate 206 sandwiched between a dielectric layer (not shown) and the bottom electrode 204. The dielectric layer can comprise a hydrophobic material and/or can be coated with a hydrophobic material, as described below. For microfluidic devices 200 that have an EW configuration, the inner surface 208 of the support structure 104 is the inner surface of the dielectric layer or its hydrophobic coating.

The dielectric layer (not shown) can comprise one or more oxide layers, and can have a thickness of about 50 nm to about 250 nm (e.g., about 125 nm to about 175 nm). In certain embodiments, the dielectric layer may comprise a layer of oxide, such as a metal oxide (e.g., aluminum oxide or hafnium oxide). In certain embodiments, the dielectric layer can comprise a dielectric material other than a metal oxide, such as silicon oxide or a nitride. Regardless of the exact composition and thickness, the dielectric layer can have an impedance of about 10 kOhms to about 50 kOhms.

In some embodiments, the surface of the dielectric layer that faces inward toward region/chamber 202 is coated with a hydrophobic material. The hydrophobic material can comprise, for example, fluorinated carbon molecules. Examples of fluorinated carbon molecules include perfluoro-polymers such as polytetrafluoroethylene (e.g., TEFLON®) or poly (2,3-difluoromethylenyl-perfluorotetrahydrofuran) (e.g., CYTOP™). Molecules that make up the hydrophobic material can be covalently bonded to the surface of the dielectric layer. For example, molecules of the hydrophobic material can be covalently bound to the surface of the dielectric layer by means of a linker such as a siloxane group, a phosphonic acid group, or a thiol group. Thus, in some embodiments, the hydrophobic material can comprise alkyl-terminated siloxane, alkyl-termination phosphonic acid, or alkyl-terminated thiol. The alkyl group can be long-chain hydrocarbons (e.g., having a chain of at least 10 carbons, or at least 16, 18, 20, 22, or more carbons). Alternatively, fluorinated (or perfluorinated) carbon chains can be used in place of the alkyl groups. Thus, for example, the hydrophobic material can comprise fluoroalkyl-terminated siloxane, fluoroalkyl-terminated phosphonic acid, or fluoroalkyl-terminated thiol. In some embodiments, the hydrophobic coating has a thickness of about 10 nm to about 50 nm. In other embodiments, the hydrophobic coating has a thickness of less than 10 nm (e.g., less than 5 nm, or about 1.5 to 3.0 nm).

In some embodiments, the cover 110 of a microfluidic device 200 having an electrowetting configuration is coated with a hydrophobic material (not shown) as well. The hydrophobic material can be the same hydrophobic material used to coat the dielectric layer of the support structure 104, and the hydrophobic coating can have a thickness that is substantially the same as the thickness of the hydrophobic coating on the dielectric layer of the support structure 104. Moreover, the cover 110 can comprise an electrode activation substrate 206 sandwiched between a dielectric layer and the top electrode 210, in the manner of the support structure 104. The electrode activation substrate 206 and the dielectric layer of the cover 110 can have the same composition and/or dimensions as the electrode activation substrate 206 and the dielectric layer of the support structure 104. Thus, the microfluidic device 200 can have two electrowetting surfaces.

In some embodiments, the electrode activation substrate 206 can comprise a photoconductive material, such as described above. Accordingly, in certain embodiments, the electrode activation substrate 206 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 μm. Alternatively, the electrode activation substrate 206 can comprise electrodes (e.g., conductive metal electrodes) controlled by phototransistor switches, as described above. Microfluidic devices having an opto-electrowetting configuration are known in the art and/or can be constructed with electrode activation substrates known in the art. For example, U.S. Pat. No. 6,958,132 (Chiou et al.), the entire contents of which are incorporated herein by reference, discloses opto-electrowetting configurations having a photoconductive material such as a-Si:H, while U.S. Patent Publication No. 2014/0124370 (Short et al.), referenced above, discloses electrode activation substrates having electrodes controlled by phototransistor switches.

The microfluidic device 200 thus can have an opto-electrowetting configuration, and light patterns 218 can be used to activate photoconductive EW regions or photoresponsive EW electrodes in the electrode activation substrate 206. Such activated EW regions or EW electrodes of the electrode activation substrate 206 can generate an electrowetting force at the inner surface 208 of the support structure 104 (i.e., the inner surface of the overlaying dielectric layer or its hydrophobic coating). By changing the light patterns 218 (or moving microfluidic device 200 relative to the light source 216) incident on the electrode activation substrate 206, droplets (e.g., containing an aqueous medium, solution, or solvent) contacting the inner surface 208 of the support structure 104 can be moved through an immiscible fluid (e.g., an oil medium) present in the region/chamber 202.

In other embodiments, microfluidic devices 200 can have an EWOD configuration, and the electrode activation substrate 206 can comprise selectively addressable and energizable electrodes that do not rely upon light for activation. The electrode activation substrate 206 thus can include a pattern of such electrowetting (EW) electrodes. The pattern, for example, can be an array of substantially square EW electrodes arranged in rows and columns, such as shown in FIG. 2B. Alternatively, the pattern can be an array of substantially hexagonal EW electrodes that form a hexagonal lattice. Regardless of the pattern, the EW electrodes can be selectively activated (or deactivated) by electrical switches (e.g., transistor switches in a semiconductor substrate). By selectively activating and deactivating EW electrodes in the electrode activation substrate 206, droplets (not shown) contacting the inner surface 208 of the overlaying dielectric layer or its hydrophobic coating can be moved within the region/chamber 202. The motive module 162 in FIG. 1A can control such switches and thus activate and deactivate individual EW electrodes to select and move particular droplets around region/chamber 202. Microfluidic devices having a EWOD configuration with selectively addressable and energizable electrodes are known in the art and have been described, for example, in U.S. Pat. No. 8,685,344 (Sundarsan et al.), the entire contents of which are incorporated herein by reference.

Regardless of the configuration of the microfluidic device 200, a power source 212 can be used to provide a potential (e.g., an AC voltage potential) that powers the electrical circuits of the microfluidic device 200. The power source 212 can be the same as, or a component of, the power source 192 referenced in FIG. 1. Power source 212 can be configured to provide an AC voltage and/or current to the top electrode 210 and the bottom electrode 204. For an AC voltage, the power source 212 can provide a frequency range and an average or peak power (e.g., voltage or current) range sufficient to generate net DEP forces (or electrowetting forces) strong enough to trap and move individual micro-objects (not shown) in the region/chamber 202, as discussed above, and/or to change the wetting properties of the inner surface 208 of the support structure 104 (i.e., the dielectric layer and/or the hydrophobic coating on the dielectric layer) in the region/chamber 202, as also discussed above. Such frequency ranges and average or peak power ranges are known in the art. See, e.g., U.S. Pat. No. 6,958,132 (Chiou et al.), U.S. Pat. No. RE44,711 (Wu et al.) (originally issued as U.S. Pat. No. 7,612,355), and US Patent Application Publication Nos. US2014/0124370 (Short et al.), US2015/0306598 (Khandros et al.), and US2015/0306599 (Khandros et al.).

Sequestration pens. Non-limiting examples of generic sequestration pens 224, 226, and 228 are shown within the microfluidic device 230 depicted in FIGS. 2A-2C. Each sequestration pen 224, 226, and 228 can comprise an isolation structure 232 defining an isolation region 240 and a connection region 236 fluidically connecting the isolation region 240 to a channel 122. The connection region 236 can comprise a proximal opening 234 to the microfluidic channel 122 and a distal opening 238 to the isolation region 240. The connection region 236 can be configured so that the maximum penetration depth of a flow of a fluidic medium (not shown) flowing from the microfluidic channel 122 into the sequestration pen 224, 226, 228 does not extend into the isolation region 240. Thus, due to the connection region 236, a micro-object (not shown) or other material (not shown) disposed in an isolation region 240 of a sequestration pen 224, 226, 228 can thus be isolated from, and not substantially affected by, a flow of medium 180 in the microfluidic channel 122.

Figure 2A:
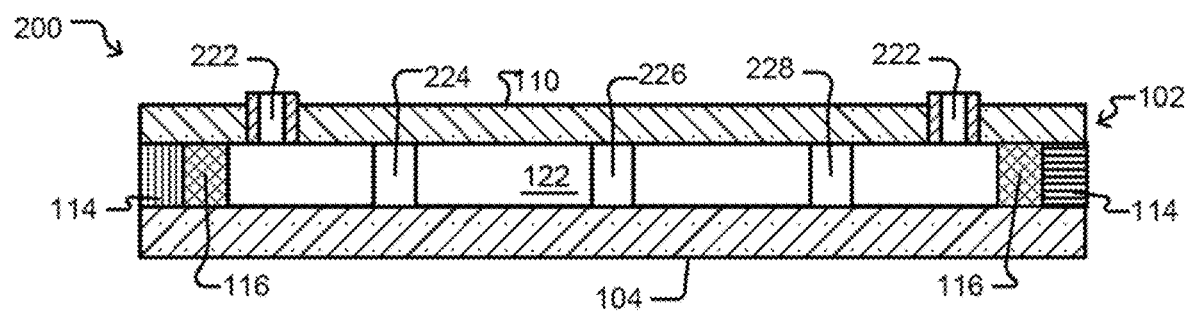
FIGS. 2A and 2B illustrate isolation pens according to some embodiments of the disclosure.
Figure 2B:
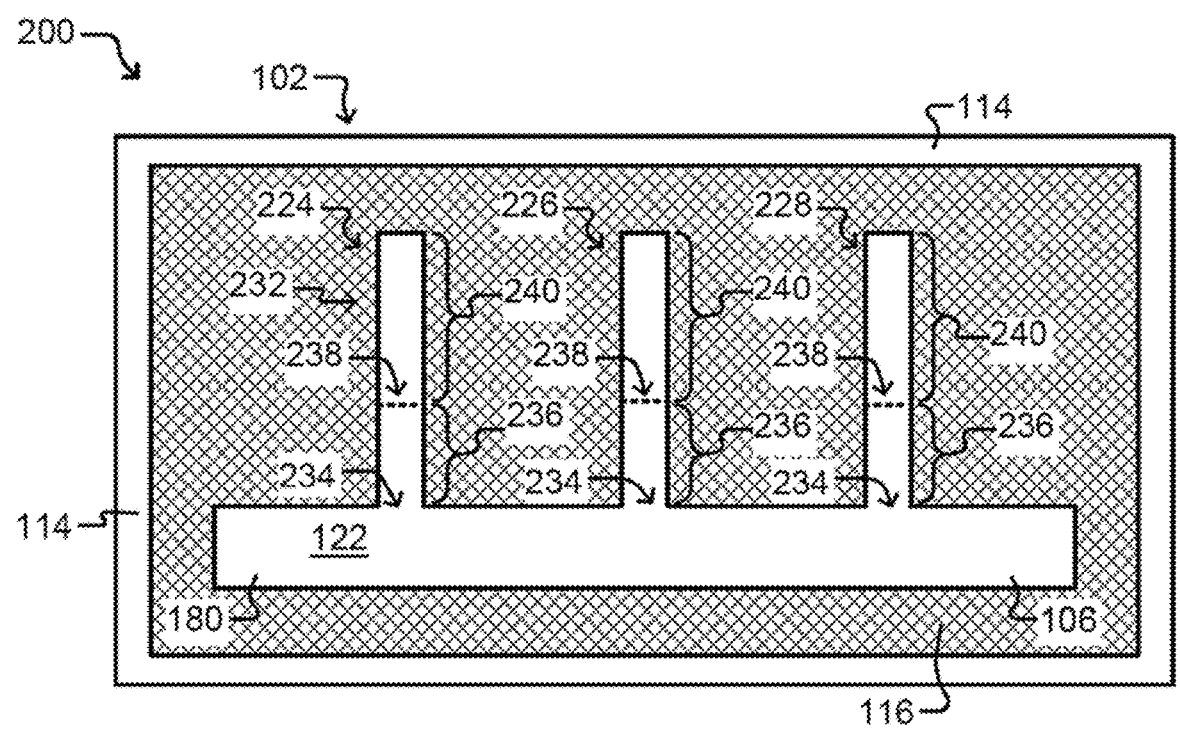
Figure 2C:
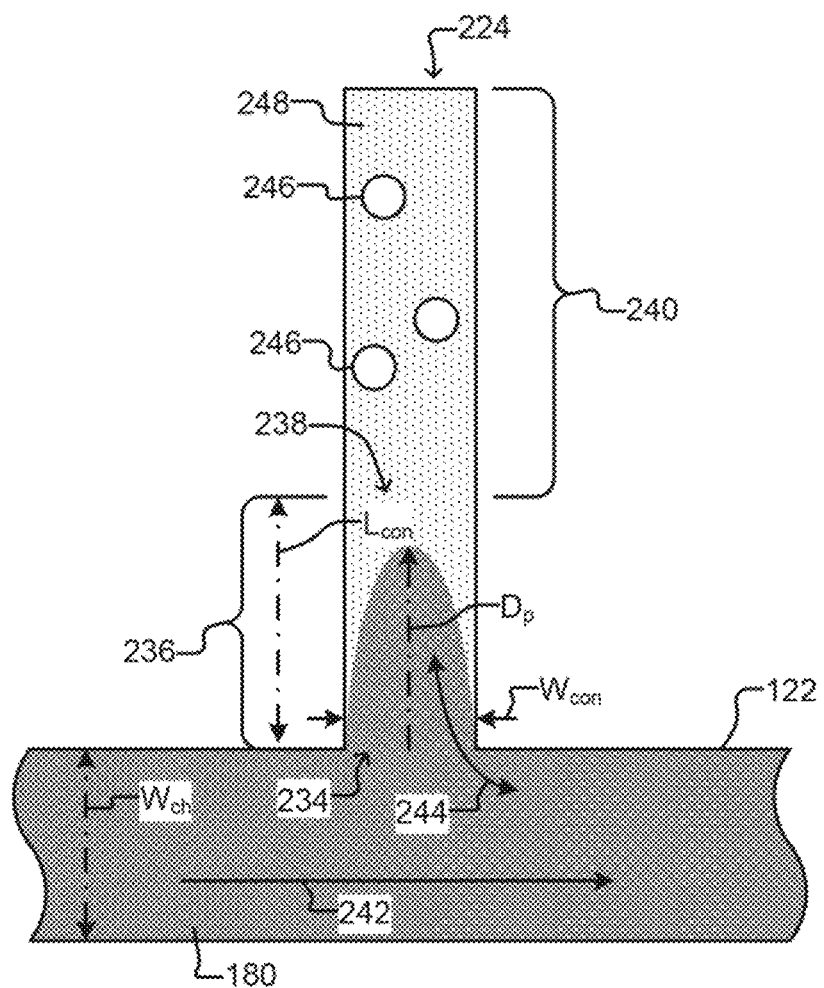
FIG. 2C illustrates a detailed sequestration pen according to some embodiments of the disclosure.

The sequestration pens 224, 226, and 228 of FIGS. 2A-2C each have a single opening which opens directly to the microfluidic channel 122. The opening of the sequestration pen opens laterally from the microfluidic channel 122. The electrode activation substrate 206 underlays both the microfluidic channel 122 and the sequestration pens 224, 226, and 228. The upper surface of the electrode activation substrate 206 within the enclosure of a sequestration pen, forming the floor of the sequestration pen, is disposed at the same level or substantially the same level of the upper surface the of electrode activation substrate 206 within the microfluidic channel 122 (or flow region if a channel is not present), forming the floor of the flow channel (or flow region, respectively) of the microfluidic device. The electrode activation substrate 206 may be featureless or may have an irregular or patterned surface that varies from its highest elevation to its lowest depression by less than about 3 microns, 2.5 microns, 2 microns, 1.5 microns, 1 micron, 0.9 microns, 0.5 microns, 0.4 microns, 0.2 microns, 0.1 microns or less. The variation of elevation in the upper surface of the substrate across both the microfluidic channel 122 (or flow region) and sequestration pens may be less than about 3%, 2%, 1%. 0.9%, 0.8%, 0.5%, 0.3% or 0.1% of the height of the walls of the sequestration pen or walls of the microfluidic device. While described in detail for the microfluidic device 200, this also applies to any of the microfluidic devices 100, 230, 250, 280, 290, 320, 400, 450, 500, 700 described herein.

The microfluidic channel 122 can thus be an example of a swept region, and the isolation regions 240 of the sequestration pens 224, 226, 228 can be examples of unswept regions. As noted, the microfluidic channel 122 and sequestration pens 224, 226, 228 can be configured to contain one or more fluidic media 180. In the example shown in FIGS. 2A-2B, the ports 222 are connected to the microfluidic channel 122 and allow a fluidic medium 180 to be introduced into or removed from the microfluidic device 230. Prior to introduction of the fluidic medium 180, the microfluidic device may be primed with a gas such as carbon dioxide gas. Once the microfluidic device 230 contains the fluidic medium 180, the flow 242 of fluidic medium 180 in the microfluidic channel 122 can be selectively generated and stopped. For example, as shown, the ports 222 can be disposed at different locations (e.g., opposite ends) of the microfluidic channel 122, and a flow 242 of medium can be created from one port 222 functioning as an inlet to another port 222 functioning as an outlet.

FIG. 2C illustrates a detailed view of an example of a sequestration pen 224 according to the present disclosure. Examples of micro-objects 246 are also shown.

As is known, a flow 242 of fluidic medium 180 in a microfluidic channel 122 past a proximal opening 234 of sequestration pen 224 can cause a secondary flow 244 of the medium 180 into and/or out of the sequestration pen 224. To isolate micro-objects 246 in the isolation region 240 of a sequestration pen 224 from the secondary flow 244, the length $L_{con}$ of the connection region 236 of the sequestration pen 224 (i.e., from the proximal opening 234 to the distal opening 238) should be greater than the penetration depth $D_p$ of the secondary flow 244 into the connection region 236. The penetration depth $D_p$ of the secondary flow 244 depends upon the velocity of the fluidic medium 180 flowing in the microfluidic channel 122 and various parameters relating to the configuration of the microfluidic channel 122 and the proximal opening 234 of the connection region 236 to the microfluidic channel 122. For a given microfluidic device, the configurations of the microfluidic channel 122 and the opening 234 will be fixed, whereas the rate of flow 242 of fluidic medium 180 in the microfluidic channel 122 will be variable. Accordingly, for each sequestration pen 224, a maximal velocity $V_{max}$ for the flow 242 of fluidic medium 180 in channel 122 can be identified that ensures that the penetration depth $D_p$ of the secondary flow 244 does not exceed the length $L_{con}$ of the connection region 236. As long as the rate of the flow 242 of fluidic medium 180 in the microfluidic channel 122 does not exceed the maximum velocity $V_{max}$, the resulting secondary flow 244 can be limited to the microfluidic channel 122 and the connection region 236 and kept out of the isolation region 240. The flow 242 of medium 180 in the microfluidic channel 122 will thus not draw micro-objects 246 out of the isolation region 240. Rather, micro-objects 246 located in the isolation region 240 will stay in the isolation region 240 regardless of the flow 242 of fluidic medium 180 in the microfluidic channel 122.

Moreover, as long as the rate of flow 242 of medium 180 in the microfluidic channel 122 does not exceed $V_{max}$, the flow 242 of fluidic medium 180 in the microfluidic channel 122 will not move miscellaneous particles (e.g., microparticles and/or nanoparticles) from the microfluidic channel 122 into the isolation region 240 of a sequestration pen 224. Having the length $L_{con}$ of the connection region 236 be greater than the maximum penetration depth $D_p$ of the secondary flow 244 can thus prevent contamination of one sequestration pen 224 with miscellaneous particles from the microfluidic channel 122 or another sequestration pen (e.g., sequestration pens 226, 228 in FIG. 2D).

Because the microfluidic channel 122 and the connection regions 236 of the sequestration pens 224, 226, 228 can be affected by the flow 242 of medium 180 in the microfluidic channel 122, the microfluidic channel 122 and connection regions 236 can be deemed swept (or flow) regions of the microfluidic device 230. The isolation regions 240 of the sequestration pens 224, 226, 228, on the other hand, can be deemed unswept (or non-flow) regions. For example, components (not shown) in a first fluidic medium 180 in the microfluidic channel 122 can mix with a second fluidic medium 248 in the isolation region 240 substantially only by diffusion of components of the first medium 180 from the microfluidic channel 122 through the connection region 236 and into the second fluidic medium 248 in the isolation region 240. Similarly, components (not shown) of the second medium 248 in the isolation region 240 can mix with the first medium 180 in the microfluidic channel 122 substantially only by diffusion of components of the second medium 248 from the isolation region 240 through the connection region 236 and into the first medium 180 in the microfluidic channel 122. In some embodiments, the extent of fluidic medium exchange between the isolation region of a sequestration pen and the flow region by diffusion is greater than about 90%, 91%, 92%, 93%, 94% 95%, 96%, 97%, 98%, or greater than about 99% of fluidic exchange. The first medium 180 can be the same medium or a different medium than the second medium 248. Moreover, the first medium 180 and the second medium 248 can start out being the same, then become different (e.g., through conditioning of the second medium 248 by one or more cells in the isolation region 240, or by changing the medium 180 flowing through the microfluidic channel 122).

The maximum penetration depth $D_p$ of the secondary flow 244 caused by the flow 242 of fluidic medium 180 in the microfluidic channel 122 can depend on a number of parameters, as mentioned above. Examples of such parameters include: the shape of the microfluidic channel 122 (e.g., the microfluidic channel can direct medium into the connection region 236, divert medium away from the connection region 236, or direct medium in a direction substantially perpendicular to the proximal opening 234 of the connection region 236 to the microfluidic channel 122); a width $W_{ch}$ (or cross-sectional area) of the microfluidic channel 122 at the proximal opening 234; and a width $W_{con}$ (or cross-sectional area) of the connection region 236 at the proximal opening 234; the velocity V of the flow 242 of fluidic medium 180 in the microfluidic channel 122; the viscosity of the first medium 180 and/or the second medium 248, or the like.

In some embodiments, the dimensions of the microfluidic channel 122 and sequestration pens 224, 226, 228 can be oriented as follows with respect to the vector of the flow 242 of fluidic medium 180 in the microfluidic channel 122: the microfluidic channel width $W_{ch}$ (or cross-sectional area of the microfluidic channel 122) can be substantially perpendicular to the flow 242 of medium 180; the width $W_{con}$ (or cross-sectional area) of the connection region 236 at opening 234 can be substantially parallel to the flow 242 of medium 180 in the microfluidic channel 122; and/or the length $L_{con}$ of the connection region can be substantially perpendicular to the flow 242 of medium 180 in the microfluidic channel 122. The foregoing are examples only, and the relative position of the microfluidic channel 122 and sequestration pens 224, 226, 228 can be in other orientations with respect to each other.

As illustrated in FIG. 2C, the width $W_{con}$ of the connection region 236 be uniform from the proximal opening 234 to the distal opening 238. The width $W_{con}$ of the connection region 236 at the distal opening 238 can thus be in any of the ranges identified herein for the width $W_{con}$ of the connection region 236 at the proximal opening 234. Alternatively, the width $W_{con}$ of the connection region 236 at the distal opening 238 can be larger than the width $W_{con}$ of the connection region 236 at the proximal opening 234.

As illustrated in FIG. 2C, the width of the isolation region 240 at the distal opening 238 can be substantially the same as the width $W_{con}$ of the connection region 236 at the proximal opening 234. The width of the isolation region 240 at the distal opening 238 can thus be in any of the ranges identified herein for the width $W_{con}$ of the connection region 236 at the proximal opening 234. Alternatively, the width of the isolation region 240 at the distal opening 238 can be larger or smaller than the width $W_{con}$ of the connection region 236 at the proximal opening 234. Moreover, the distal opening 238 may be smaller than the proximal opening 234 and the width $W_{con}$ of the connection region 236 may be narrowed between the proximal opening 234 and distal opening 238. For example, the connection region 236 may be narrowed between the proximal opening and the distal opening, using a variety of different geometries (e.g. chamfering the connection region, beveling the connection region). Further, any part or subpart of the connection region 236 may be narrowed (e.g. a portion of the connection region adjacent to the proximal opening 234).

Figure 2D:
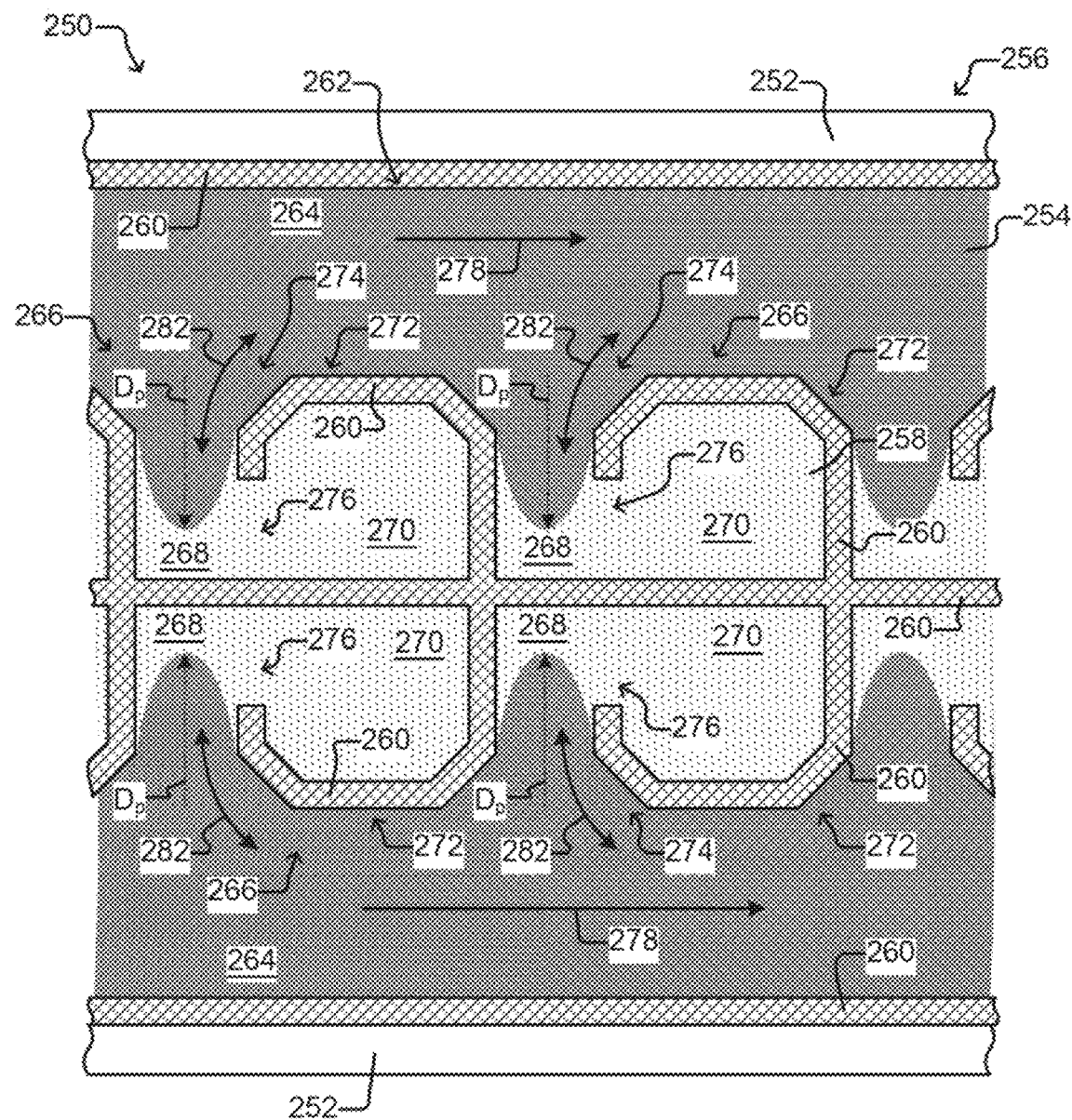
FIGS. 2D-F illustrate sequestration pens according to some other embodiments of the disclosure.
Figure 2E:
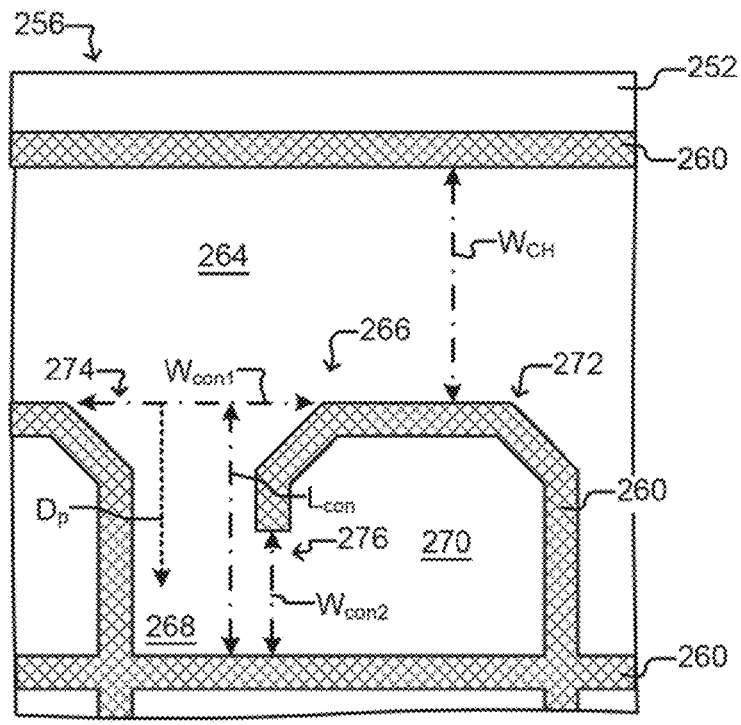
Figure 2F:
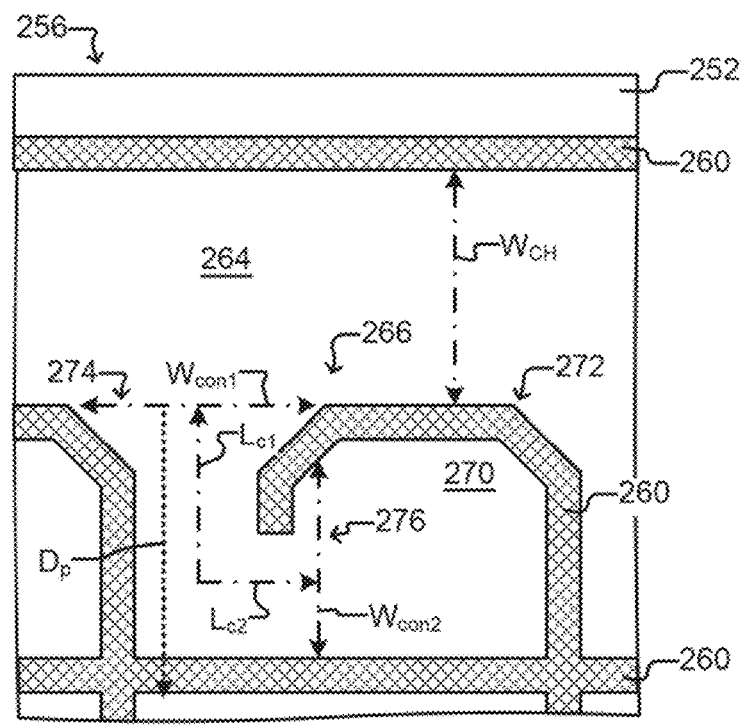

FIGS. 2D-2F depict another exemplary embodiment of a microfluidic device 250 containing a microfluidic circuit 262 and flow channels 264, which are variations of the respective microfluidic device 100, circuit 132 and channel 134 of FIG. 1A. The microfluidic device 250 also has a plurality of sequestration pens 266 that are additional variations of the above-described sequestration pens 124, 126, 128, 130, 224, 226 or 228. In particular, it should be appreciated that the sequestration pens 266 of device 250 shown in FIGS. 2D-2F can replace any of the above-described sequestration pens 124, 126, 128, 130, 224, 226 or 228 in devices 100, 200, 230, 280, 290, 300. Likewise, the microfluidic device 250 is another variant of the microfluidic device 100, and may also have the same or a different DEP configuration as the above-described microfluidic device 100, 200, 230, 280, 290, 300 as well as any of the other microfluidic system components described herein.

The microfluidic device 250 of FIGS. 2D-2F comprises a support structure (not visible in FIGS. 2D-2F, but can be the same or generally similar to the support structure 104 of device 100 depicted in FIG. 1A), a microfluidic circuit structure 256, and a cover (not visible in FIGS. 2D-2F, but can be the same or generally similar to the cover 122 of device 100 depicted in FIG. 1A). The microfluidic circuit structure 256 includes a frame 252 and microfluidic circuit material 260, which can be the same as or generally similar to the frame 114 and microfluidic circuit material 116 of device 100 shown in FIG. 1A. As shown in FIG. 2D, the microfluidic circuit 262 defined by the microfluidic circuit material 260 can comprise multiple channels 264 (two are shown but there can be more) to which multiple sequestration pens 266 are fluidically connected.

Each sequestration pen 266 can comprise an isolation structure 272, an isolation region 270 within the isolation structure 272, and a connection region 268. From a proximal opening 274 at the microfluidic channel 264 to a distal opening 276 at the isolation structure 272, the connection region 268 fluidically connects the microfluidic channel 264 to the isolation region 270. Generally, in accordance with the above discussion of FIGS. 2B and 2C, a flow 278 of a first fluidic medium 254 in a channel 264 can create secondary flows 282 of the first medium 254 from the microfluidic channel 264 into and/or out of the respective connection regions 268 of the sequestration pens 266.

As illustrated in FIG. 2E, the connection region 268 of each sequestration pen 266 generally includes the area extending between the proximal opening 274 to a channel 264 and the distal opening 276 to an isolation structure 272. The length $L_{con}$ of the connection region 268 can be greater than the maximum penetration depth $D_p$ of secondary flow 282, in which case the secondary flow 282 will extend into the connection region 268 without being redirected toward the isolation region 270 (as shown in FIG. 2D). Alternatively, at illustrated in FIG. 2F, the connection region 268 can have a length $L_{con}$ that is less than the maximum penetration depth $D_p$, in which case the secondary flow 282 will extend through the connection region 268 and be redirected toward the isolation region 270. In this latter situation, the sum of lengths $L_{c1}$ and $L_{c2}$ of connection region 268 is greater than the maximum penetration depth $D_p$, so that secondary flow 282 will not extend into isolation region 270. Whether length $L_{con}$ of connection region 268 is greater than the penetration depth $D_p$, or the sum of lengths $L_{c1}$ and $L_{c2}$ of connection region 268 is greater than the penetration depth $D_p$, a flow 278 of a first medium 254 in channel 264 that does not exceed a maximum velocity $V_{max}$ will produce a secondary flow having a penetration depth $D_p$, and micro-objects (not shown but can be the same or generally similar to the micro-objects 246 shown in FIG. 2C) in the isolation region 270 of a sequestration pen 266 will not be drawn out of the isolation region 270 by a flow 278 of first medium 254 in channel 264. Nor will the flow 278 in channel 264 draw miscellaneous materials (not shown) from channel 264 into the isolation region 270 of a sequestration pen 266. As such, diffusion is the only mechanism by which components in a first medium 254 in the microfluidic channel 264 can move from the microfluidic channel 264 into a second medium 258 in an isolation region 270 of a sequestration pen 266. Likewise, diffusion is the only mechanism by which components in a second medium 258 in an isolation region 270 of a sequestration pen 266 can move from the isolation region 270 to a first medium 254 in the microfluidic channel 264. The first medium 254 can be the same medium as the second medium 258, or the first medium 254 can be a different medium than the second medium 258. Alternatively, the first medium 254 and the second medium 258 can start out being the same, then become different, e.g., through conditioning of the second medium by one or more cells in the isolation region 270, or by changing the medium flowing through the microfluidic channel 264.

As illustrated in FIG. 2E, the width $W_{ch}$ of the microfluidic channels 264 (i.e., taken transverse to the direction of a fluid medium flow through the microfluidic channel indicated by arrows 278 in FIG. 2D) in the microfluidic channel 264 can be substantially perpendicular to a width $W_{con1}$ of the proximal opening 274 and thus substantially parallel to a width $W_{con2}$ of the distal opening 276. The width $W_{con1}$ of the proximal opening 274 and the width $W_{con2}$ of the distal opening 276, however, need not be substantially perpendicular to each other. For example, an angle between an axis (not shown) on which the width $W_{con1}$ of the proximal opening 274 is oriented and another axis on which the width $W_{con2}$ of the distal opening 276 is oriented can be other than perpendicular and thus other than 90°. Examples of alternatively oriented angles include angles in any of the following ranges: from about 30° to about 90°, from about 45° to about 90°, from about 60° to about 90°, or the like.

In various embodiments of sequestration pens (e.g. 124, 126, 128, 130, 224, 226, 228, or 266), the isolation region (e.g. 240 or 270) is configured to contain a plurality of micro-objects. In other embodiments, the isolation region can be configured to contain only one, two, three, four, five, or a similar relatively small number of micro-objects. Accordingly, the volume of an isolation region can be, for example, at least $1 \times 10^6$, $2 \times 10^6$, $4 \times 10^6$, $6 \times 10^6$ cubic microns, or more.

In various embodiments of sequestration pens, the width $W_{ch}$ of the microfluidic channel (e.g., 122) at a proximal opening (e.g. 234) can be within any of the following ranges: about 50-1000 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, and 100-120 microns. In some other embodiments, the width $W_{ch}$ of the microfluidic channel (e.g., 122) at a proximal opening (e.g. 234) can be of about 200-800 microns, 200-700 microns, or 200-600 microns. The foregoing are examples only, and the width $W_{ch}$ of the microfluidic channel 122 can be in other ranges (e.g., a range defined by any of the endpoints listed above). Moreover, the $W_{ch}$ of the microfluidic channel 122 can be selected to be in any of these ranges in regions of the microfluidic channel other than at a proximal opening of a sequestration pen.

In some embodiments, a sequestration pen has a height of about 30 to about 200 microns, or about 50 to about 150 microns. In some embodiments, the sequestration pen has a cross-sectional area of about $1 \times 10^4$-$3 \times 10^6$ square microns, $2 \times 10^4$-$2 \times 10^6$ square microns, $4 \times 10^4$-$1 \times 10^6$ square microns, $2 \times 10^4$-$5 \times 10^5$ square microns, $2 \times 10^4$-$1 \times 10^5$ square microns or about $2 \times 10^5$-$2 \times 10^6$ square microns.

In various embodiments of sequestration pens, the height $H_{ch}$ of the microfluidic channel (e.g., 122) at a proximal opening (e.g., 234) can be within any of the following ranges: 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height $H_{ch}$ of the microfluidic channel (e.g., 122) can be in other ranges (e.g., a range defined by any of the endpoints listed above). The height $H_{ch}$ of the microfluidic channel 122 can be selected to be in any of these ranges in regions of the microfluidic channel other than at a proximal opening of a sequestration pen.

In various embodiments of sequestration pens a cross-sectional area of the microfluidic channel (e.g., 122) at a proximal opening (e.g., 234) can be within any of the following ranges: 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the microfluidic channel (e.g., 122) at a proximal opening (e.g., 234) can be in other ranges (e.g., a range defined by any of the endpoints listed above).

In various embodiments of sequestration pens, the length $L_{con}$ of the connection region (e.g., 236) can be in any of the following ranges: about 1-600 microns, 5-550 microns, 10-500 microns, 15-400 microns, 20-300 microns, 20-500 microns, 40-400 microns, 60-300 microns, 80-200 microns, or about 100-150 microns. The foregoing are examples only, and length $L_{con}$ of a connection region (e.g., 236) can be in a different range than the foregoing examples (e.g., a range defined by any of the endpoints listed above).

In various embodiments of sequestration pens the width $W_{con}$ of a connection region (e.g., 236) at a proximal opening (e.g., 234) can be in any of the following ranges: 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-250 microns, 50-200 microns, 50-150 microns, 50-100 microns, 50-80 microns, 60-200 microns, 60-150 microns, 60-100 microns, 60-80 microns, 70-150 microns, 70-100 microns, and 80-100 microns. The foregoing are examples only, and the width $W_{con}$ of a connection region (e.g., 236) at a proximal opening (e.g., 234) can be different than the foregoing examples (e.g., a range defined by any of the endpoints listed above).

In various embodiments of sequestration pens, the width $W_{con}$ of a connection region (e.g., 236) at a proximal opening (e.g., 234) can be at least as large as the largest dimension of a micro-object (e.g., biological cell which may be a T cell, B cell, or an ovum) that the sequestration pen is intended for. The foregoing are examples only, and the width $W_{con}$ of a connection region (e.g., 236) at a proximal opening (e.g., 234) can be different than the foregoing examples (e.g., a range defined by any of the endpoints listed above).

In various embodiments of sequestration pens, the width $W_{pr}$ of a proximal opening of a connection region may be at least as large as the largest dimension of a micro-object (e.g., a biological micro-object such as a cell) that the sequestration pen is intended for. For example, the width $W_{pr}$ may be about 50 microns, about 60 microns, about 100 microns, about 200 microns, about 300 microns or may be of about 50-300 microns, about 50-200 microns, about 50-100 microns, about 75-150 microns, about 75-100 microns, or about 200-300 microns In various embodiments of sequestration pens, a ratio of the length L on of a connection region (e.g., 236) to a width $W_{con}$ of the connection region (e.g., 236) at the proximal opening 234 can be greater than or equal to any of the following ratios: 0.5, 1.0, 1.5, 2.0, 2.5, 3.0, 3.5, 4.0, 4.5, 5.0, 6.0, 7.0, 8.0, 9.0, 10.0, or more. The foregoing are examples only, and the ratio of the length L on of a connection region 236 to a width $W_{con}$ of the connection region 236 at the proximal opening 234 can be different than the foregoing examples.

In various embodiments of microfluidic devices 100, 200, 23, 250, 280, 290, 300, $V_{max}$ can be set around 0.2, 0.5, 0.7, 1.0, 1.3, 1.5, 2.0, 2.5, 3.0, 3.5, 4.0, 4.5, 5.0, 5.5, 6.0, 6.7, 7.0, 7.5, 8.0, 8.5, 9.0, 10, 11, 12, 13, 14, or 15 microliters/sec.

In various embodiments of microfluidic devices having sequestration pens, the volume of an isolation region (e.g., 240) of a sequestration pen can be, for example, at least $5 \times 10^5$, $8 \times 10^5$, $1 \times 10^6$, $2 \times 10^6$, $4 \times 10^6$, $6 \times 10^6$, $8 \times 10^6$, $1 \times 10^7$, $5 \times 10^7$, $1 \times 10^8$, $5 \times 10^8$, or $8 \times 10^8$ cubic microns, or more. In various embodiments of microfluidic devices having sequestration pens, the volume of a sequestration pen may be about $5 \times 10^5$, $6 \times 10^5$, $8 \times 10^5$, $1 \times 10^6$, $2 \times 10^6$, $4 \times 10^6$, $8 \times 10^6$, $1 \times 10^7$, $3 \times 10^7$, $5 \times 10^7$, or about $8 \times 10^7$ cubic microns, or more. In some other embodiments, the volume of a sequestration pen may be about 1 nanoliter to about 50 nanoliters, 2 nanoliters to about 25 nanoliters, 2 nanoliters to about 20 nanoliters, about 2 nanoliters to about 15 nanoliters, or about 2 nanoliters to about 10 nanoliters.

In various embodiment, the microfluidic device has sequestration pens configured as in any of the embodiments discussed herein where the microfluidic device has about 5 to about 10 sequestration pens, about 10 to about 50 sequestration pens, about 100 to about 500 sequestration pens; about 200 to about 1000 sequestration pens, about 500 to about 1500 sequestration pens, about 1000 to about 2000 sequestration pens, about 1000 to about 3500 sequestration pens, about 2500 to about 5000 sequestration pens, about 3000 to about 7000 sequestration pens, about 5000 to about 10,000 sequestration pens, or about 8000 to about 12,0000 sequestration pens. The sequestration pens need not all be the same size and may include a variety of configurations (e.g., different widths, different features within the sequestration pen).

Figure 2G:
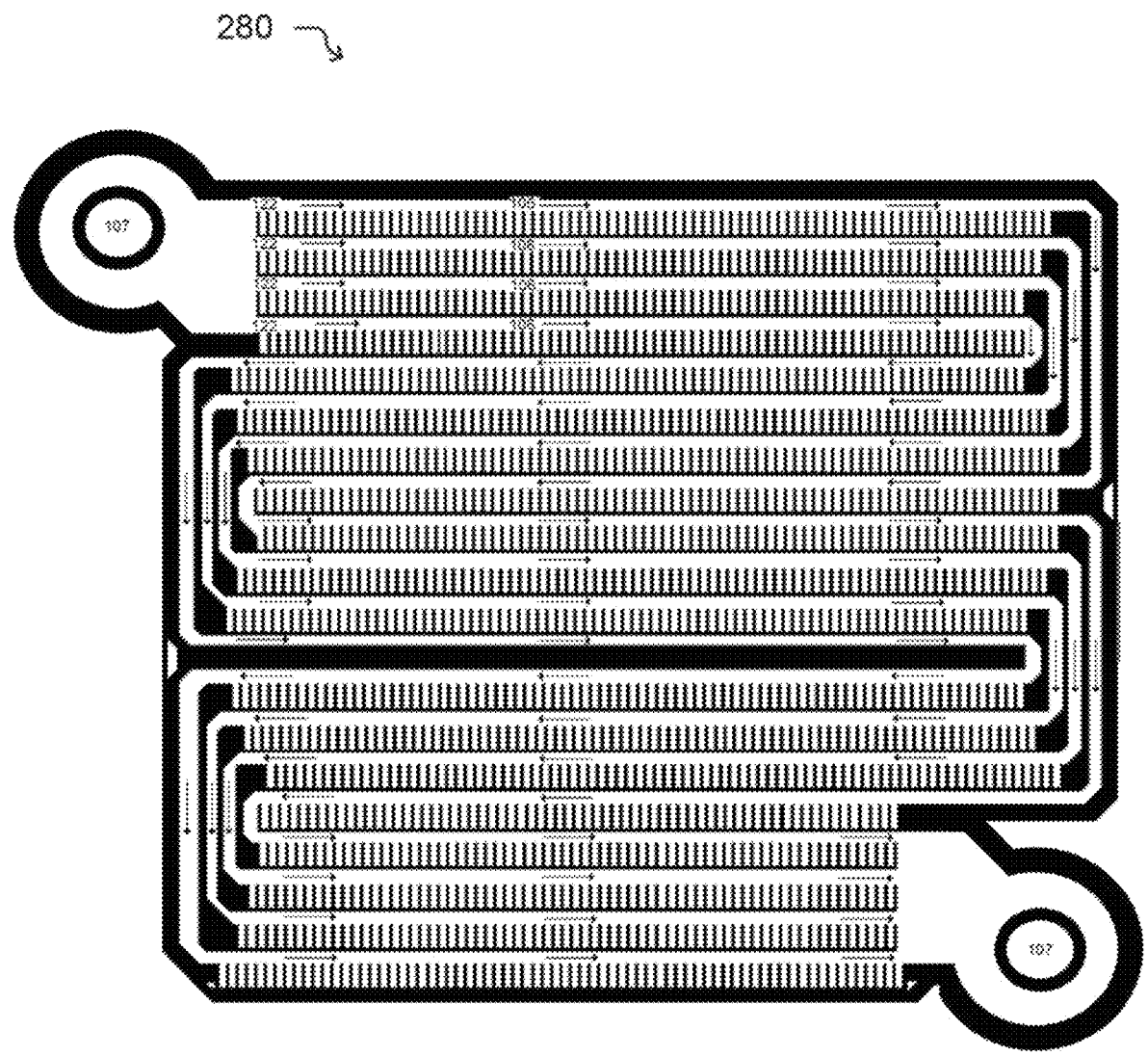
FIG. 2G illustrates a microfluidic device according to an embodiment of the disclosure.

FIG. 2G illustrates a microfluidic device 280 according to one embodiment. The microfluidic device 280 illustrated in FIG. 2G is a stylized diagram of a microfluidic device 100. In practice the microfluidic device 280 and its constituent circuit elements (e.g. channels 122 and sequestration pens 128) would have the dimensions discussed herein. The microfluidic circuit 120 illustrated in FIG. 2G has two ports 107, four distinct channels 122 and four distinct flow paths 106. The microfluidic device 280 further comprises a plurality of sequestration pens opening off of each channel 122. In the microfluidic device illustrated in FIG. 2G, the sequestration pens have a geometry similar to the pens illustrated in FIG. 2C and thus, have both connection regions and isolation regions. Accordingly, the microfluidic circuit 120 includes both swept regions (e.g. channels 122 and portions of the connection regions 236 within the maximum penetration depth $D_p$ of the secondary flow 244) and non-swept regions (e.g. isolation regions 240 and portions of the connection regions 236 not within the maximum penetration depth $D_p$ of the secondary flow 244).

Figure 3A:
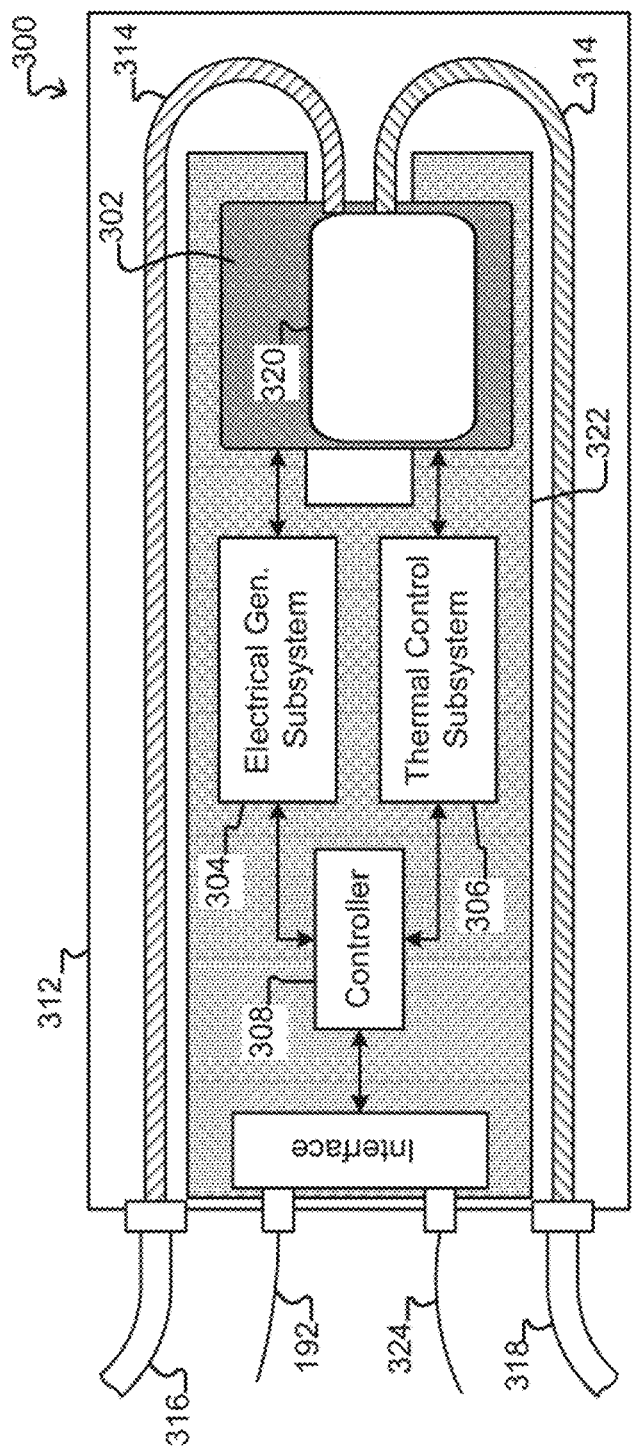
FIG. 3A illustrates a specific example of a system for use with a microfluidic device and associated control equipment according to some embodiments of the disclosure.
Figure 3B:
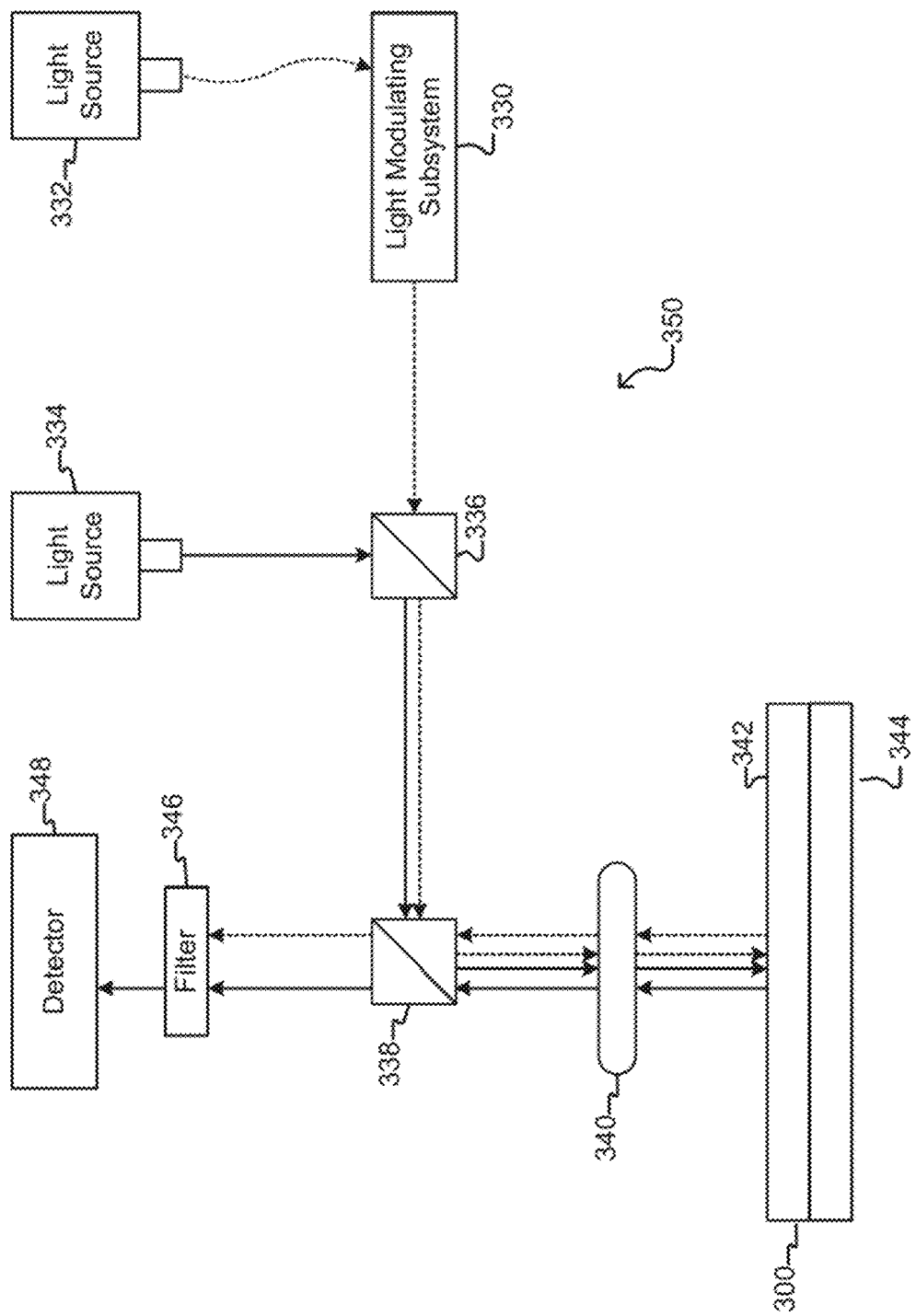
FIG. 3B illustrates an imaging device according to some embodiments of the disclosure.

FIGS. 3A through 3B shows various embodiments of system 150 which can be used to operate and observe microfluidic devices (e.g. 100, 200, 230, 250, 280, 290, 300) according to the present disclosure. As illustrated in FIG. 3A, the system 150 can include a structure ("nest") 300 configured to hold a microfluidic device 100 (not shown), or any other microfluidic device described herein. The nest 300 can include a socket 302 capable of interfacing with the microfluidic device 320 (e.g., an optically-actuated electro-kinetic device 100) and providing electrical connections from power source 192 to microfluidic device 320. The nest 300 can further include an integrated electrical signal generation subsystem 304. The electrical signal generation subsystem 304 can be configured to supply a biasing voltage to socket 302 such that the biasing voltage is applied across a pair of electrodes in the microfluidic device 320 when it is being held by socket 302. Thus, the electrical signal generation subsystem 304 can be part of power source 192. The ability to apply a biasing voltage to microfluidic device 320 does not mean that a biasing voltage will be applied at all times when the microfluidic device 320 is held by the socket 302. Rather, in most cases, the biasing voltage will be applied intermittently, e.g., only as needed to facilitate the generation of electrokinetic forces, such as dielectrophoresis or electro-wetting, in the microfluidic device 320.

As illustrated in FIG. 3A, the nest 300 can include a printed circuit board assembly (PCBA) 322. The electrical signal generation subsystem 304 can be mounted on and electrically integrated into the PCBA 322. The exemplary support includes socket 302 mounted on PCBA 322, as well.

Typically, the electrical signal generation subsystem 304 will include a waveform generator (not shown). The electrical signal generation subsystem 304 can further include an oscilloscope (not shown) and/or a waveform amplification circuit (not shown) configured to amplify a waveform received from the waveform generator. The oscilloscope, if present, can be configured to measure the waveform supplied to the microfluidic device 320 held by the socket 302. In certain embodiments, the oscilloscope measures the waveform at a location proximal to the microfluidic device 320 (and distal to the waveform generator), thus ensuring greater accuracy in measuring the waveform actually applied to the device. Data obtained from the oscilloscope measurement can be, for example, provided as feedback to the waveform generator, and the waveform generator can be configured to adjust its output based on such feedback. An example of a suitable combined waveform generator and oscilloscope is the Red Pitaya™.

In certain embodiments, the nest 300 further comprises a controller 308, such as a microprocessor used to sense and/or control the electrical signal generation subsystem 304. Examples of suitable microprocessors include the Arduino™ microprocessors, such as the Arduino Nano™ The controller 308 may be used to perform functions and analysis or may communicate with an external master controller 154 (shown in FIG. 1A) to perform functions and analysis. In the embodiment illustrated in FIG. 3A the controller 308 communicates with a master controller 154 through an interface 310 (e.g., a plug or connector).

In some embodiments, the nest 300 can comprise an electrical signal generation subsystem 304 comprising a Red Pitaya™ waveform generator/oscilloscope unit ("Red Pitaya unit") and a waveform amplification circuit that amplifies the waveform generated by the Red Pitaya unit and passes the amplified voltage to the microfluidic device 100. In some embodiments, the Red Pitaya unit is configured to measure the amplified voltage at the microfluidic device 320 and then adjust its own output voltage as needed such that the measured voltage at the microfluidic device 320 is the desired value. In some embodiments, the waveform amplification circuit can have a +6.5V to −6.5V power supply generated by a pair of DC-DC converters mounted on the PCBA 322, resulting in a signal of up to 13 Vpp at the microfluidic device 100.

As illustrated in FIG. 3A, the support structure 300 (e.g., nest) can further include a thermal control subsystem 306. The thermal control subsystem 306 can be configured to regulate the temperature of microfluidic device 320 held by the support structure 300. For example, the thermal control subsystem 306 can include a Peltier thermoelectric device (not shown) and a cooling unit (not shown). The Peltier thermoelectric device can have a first surface configured to interface with at least one surface of the microfluidic device 320. The cooling unit can be, for example, a cooling block (not shown), such as a liquid-cooled aluminum block. A second surface of the Peltier thermoelectric device (e.g., a surface opposite the first surface) can be configured to interface with a surface of such a cooling block. The cooling block can be connected to a fluidic path 314 configured to circulate cooled fluid through the cooling block. In the embodiment illustrated in FIG. 3A, the support structure 300 comprises an inlet 316 and an outlet 318 to receive cooled fluid from an external reservoir (not shown), introduce the cooled fluid into the fluidic path 314 and through the cooling block, and then return the cooled fluid to the external reservoir. In some embodiments, the Peltier thermoelectric device, the cooling unit, and/or the fluidic path 314 can be mounted on a casing 312 of the support structure 300. In some embodiments, the thermal control subsystem 306 is configured to regulate the temperature of the Peltier thermoelectric device so as to achieve a target temperature for the microfluidic device 320. Temperature regulation of the Peltier thermoelectric device can be achieved, for example, by a thermoelectric power supply, such as a Pololu™ thermoelectric power supply (Pololu Robotics and Electronics Corp.). The thermal control subsystem 306 can include a feedback circuit, such as a temperature value provided by an analog circuit. Alternatively, the feedback circuit can be provided by a digital circuit.

In some embodiments, the nest 300 can include a thermal control subsystem 306 with a feedback circuit that is an analog voltage divider circuit (not shown) which includes a resistor (e.g., with resistance 1 kOhm+/−0.1%, temperature coefficient+/−0.02 ppm/CO) and a NTC thermistor (e.g., with nominal resistance 1 kOhm+/−0.01%). In some instances, the thermal control subsystem 306 measures the voltage from the feedback circuit and then uses the calculated temperature value as input to an on-board PID control loop algorithm. Output from the PID control loop algorithm can drive, for example, both a directional and a pulse-width-modulated signal pin on a Pololu™ motor drive (not shown) to actuate the thermoelectric power supply, thereby controlling the Peltier thermoelectric device.

The nest 300 can include a serial port 324 which allows the microprocessor of the controller 308 to communicate with an external master controller 154 via the interface 310 (not shown). In addition, the microprocessor of the controller 308 can communicate (e.g., via a Plink tool (not shown)) with the electrical signal generation subsystem 304 and thermal control subsystem 306. Thus, via the combination of the controller 308, the interface 310, and the serial port 324, the electrical signal generation subsystem 304 and the thermal control subsystem 306 can communicate with the external master controller 154. In this manner, the master controller 154 can, among other things, assist the electrical signal generation subsystem 304 by performing scaling calculations for output voltage adjustments. A Graphical User Interface (GUI) (not shown) provided via a display device 170 coupled to the external master controller 154, can be configured to plot temperature and waveform data obtained from the thermal control subsystem 306 and the electrical signal generation subsystem 304, respectively. Alternatively, or in addition, the GUI can allow for updates to the controller 308, the thermal control subsystem 306, and the electrical signal generation subsystem 304.

As discussed above, system 150 can include an imaging device 194. In some embodiments, the imaging device 194 comprises a light modulating subsystem 330 (See FIG. 3B). The light modulating subsystem 330 can include a digital mirror device (DMD) or a microshutter array system (MSA), either of which can be configured to receive light from a light source 332 and transmits a subset of the received light into an optical train of microscope 350. Alternatively, the light modulating subsystem 330 can include a device that produces its own light (and thus dispenses with the need for a light source 332), such as an organic light emitting diode display (OLED), a liquid crystal on silicon (LCOS) device, a ferroelectric liquid crystal on silicon device (FLCOS), or a transmissive liquid crystal display (LCD). The light modulating subsystem 330 can be, for example, a projector. Thus, the light modulating subsystem 330 can be capable of emitting both structured and unstructured light. In certain embodiments, imaging module 164 and/or motive module 162 of system 150 can control the light modulating subsystem 330.

In certain embodiments, the imaging device 194 further comprises a microscope 350. In such embodiments, the nest 300 and light modulating subsystem 330 can be individually configured to be mounted on the microscope 350. The microscope 350 can be, for example, a standard research-grade light microscope or fluorescence microscope. Thus, the nest 300 can be configured to be mounted on the stage 344 of the microscope 350 and/or the light modulating subsystem 330 can be configured to mount on a port of microscope 350. In other embodiments, the nest 300 and the light modulating subsystem 330 described herein can be integral components of microscope 350.

In certain embodiments, the microscope 350 can further include one or more detectors 348. In some embodiments, the detector 348 is controlled by the imaging module 164. The detector 348 can include an eye piece, a charge-coupled device (CCD), a camera (e.g., a digital camera), or any combination thereof. If at least two detectors 348 are present, one detector can be, for example, a fast-frame-rate camera while the other detector can be a high sensitivity camera. Furthermore, the microscope 350 can include an optical train configured to receive reflected and/or emitted light from the microfluidic device 320 and focus at least a portion of the reflected and/or emitted light on the one or more detectors 348. The optical train of the microscope can also include different tube lenses (not shown) for the different detectors, such that the final magnification on each detector can be different.

In certain embodiments, imaging device 194 is configured to use at least two light sources. For example, a first light source 332 can be used to produce structured light (e.g., via the light modulating subsystem 330) and a second light source 334 can be used to provide unstructured light. The first light source 332 can produce structured light for optically-actuated electrokinesis and/or fluorescent excitation, and the second light source 334 can be used to provide bright field illumination. In these embodiments, the motive module 164 can be used to control the first light source 332 and the imaging module 164 can be used to control the second light source 334. The optical train of the microscope 350 can be configured to (1) receive structured light from the light modulating subsystem 330 and focus the structured light on at least a first region in a microfluidic device, such as an optically-actuated electrokinetic device, when the device is being held by the nest 300, and (2) receive reflected and/or emitted light from the microfluidic device and focus at least a portion of such reflected and/or emitted light onto detector 348. The optical train can be further configured to receive unstructured light from a second light source and focus the unstructured light on at least a second region of the microfluidic device, when the device is held by the nest 300. In certain embodiments, the first and second regions of the microfluidic device can be overlapping regions. For example, the first region can be a subset of the second region. In other embodiments, the second light source 334 may additionally or alternatively include a laser, which may have any suitable wavelength of light. The representation of the optical system shown in FIG. 3B is a schematic representation only, and the optical system may include additional filters, notch filters, lenses and the like. When the second light source 334 includes one or more light source(s) for brightfield and/or fluorescent excitation, as well as laser illumination the physical arrangement of the light source(s) may vary from that shown in FIG. 3B, and the laser illumination may be introduced at any suitable physical location within the optical system. The schematic locations of light source 432 and light source 402/light modulating subsystem 404 may be interchanged as well.

In FIG. 3B, the first light source 332 is shown supplying light to a light modulating subsystem 330, which provides structured light to the optical train of the microscope 350 of system 355 (not shown). The second light source 334 is shown providing unstructured light to the optical train via a beam splitter 336. Structured light from the light modulating subsystem 330 and unstructured light from the second light source 334 travel from the beam splitter 336 through the optical train together to reach a second beam splitter (or dichroic filter 338, depending on the light provided by the light modulating subsystem 330), where the light gets reflected down through the objective 336 to the sample plane 342. Reflected and/or emitted light from the sample plane 342 then travels back up through the objective 340, through the beam splitter and/or dichroic filter 338, and to a dichroic filter 346. Only a fraction of the light reaching dichroic filter 346 passes through and reaches the detector 348.

In some embodiments, the second light source 334 emits blue light. With an appropriate dichroic filter 346, blue light reflected from the sample plane 342 is able to pass through dichroic filter 346 and reach the detector 348. In contrast, structured light coming from the light modulating subsystem 330 gets reflected from the sample plane 342, but does not pass through the dichroic filter 346. In this example, the dichroic filter 346 is filtering out visible light having a wavelength longer than 495 nm. Such filtering out of the light from the light modulating subsystem 330 would only be complete (as shown) if the light emitted from the light modulating subsystem did not include any wavelengths shorter than 495 nm. In practice, if the light coming from the light modulating subsystem 330 includes wavelengths shorter than 495 nm (e.g., blue wavelengths), then some of the light from the light modulating subsystem would pass through filter 346 to reach the detector 348. In such an embodiment, the filter 346 acts to change the balance between the amount of light that reaches the detector 348 from the first light source 332 and the second light source 334. This can be beneficial if the first light source 332 is significantly stronger than the second light source 334. In other embodiments, the second light source 334 can emit red light, and the dichroic filter 346 can filter out visible light other than red light (e.g., visible light having a wavelength shorter than 650 nm).

Coating solutions and coating agents. Without intending to be limited by theory, maintenance of a biological micro-object (e.g., a biological cell) within a microfluidic device (e.g., a DEP-configured and/or EW-configured microfluidic device) may be facilitated (i.e., the biological micro-object exhibits increased viability, greater expansion and/or greater portability within the microfluidic device) when at least one or more inner surfaces of the microfluidic device have been conditioned or coated so as to present a layer of organic and/or hydrophilic molecules that provides the primary interface between the microfluidic device and biological micro-object(s) maintained therein. In some embodiments, one or more of the inner surfaces of the microfluidic device (e.g. the inner surface of the electrode activation substrate of a DEP-configured microfluidic device, the cover of the microfluidic device, and/or the surfaces of the circuit material) may be treated with or modified by a coating solution and/or coating agent to generate the desired layer of organic and/or hydrophilic molecules.

The coating may be applied before or after introduction of biological micro-object(s), or may be introduced concurrently with the biological micro-object(s). In some embodiments, the biological micro-object(s) may be imported into the microfluidic device in a fluidic medium that includes one or more coating agents. In other embodiments, the inner surface(s) of the microfluidic device (e.g., a DEP-configured microfluidic device) are treated or "primed" with a coating solution comprising a coating agent prior to introduction of the biological micro-object(s) into the microfluidic device.

In some embodiments, at least one surface of the microfluidic device includes a coating material that provides a layer of organic and/or hydrophilic molecules suitable for maintenance and/or expansion of biological micro-object(s) (e.g. provides a conditioned surface as described below). In some embodiments, substantially all the inner surfaces of the microfluidic device include the coating material. The coated inner surface(s) may include the surface of a flow region (e.g., channel), chamber, or sequestration pen, or a combination thereof. In some embodiments, each of a plurality of sequestration pens has at least one inner surface coated with coating materials. In other embodiments, each of a plurality of flow regions or channels has at least one inner surface coated with coating materials. In some embodiments, at least one inner surface of each of a plurality of sequestration pens and each of a plurality of channels is coated with coating materials.

Coating agent/Solution. Any convenient coating agent/coating solution can be used, including but not limited to: serum or serum factors, bovine serum albumin (BSA), polymers, detergents, enzymes, and any combination thereof.

Polymer-based coating materials. The at least one inner surface may include a coating material that comprises a polymer. The polymer may be covalently or non-covalently bound (or may be non-specifically adhered) to the at least one surface. The polymer may have a variety of structural motifs, such as found in block polymers (and copolymers), star polymers (star copolymers), and graft or comb polymers (graft copolymers), all of which may be suitable for the methods disclosed herein.

The polymer may include a polymer including alkylene ether moieties. A wide variety of alkylene ether containing polymers may be suitable for use in the microfluidic devices described herein. One non-limiting exemplary class of alkylene ether containing polymers are amphiphilic nonionic block copolymers which include blocks of polyethylene oxide (PEO) and polypropylene oxide (PPO) subunits in differing ratios and locations within the polymer chain. Pluronic® polymers (BASF) are block copolymers of this type and are known in the art to be suitable for use when in contact with living cells. The polymers may range in average molecular mass Mw from about 2000 Da to about 20 KDa. In some embodiments, the PEO-PPO block copolymer can have a hydrophilic-lipophilic balance (HLB) greater than about 10 (e.g. 12-18). Specific Pluronic® polymers useful for yielding a coated surface include Pluronic® L44, L64, P85, and F127 (including F127NF). Another class of alkylene ether containing polymers is polyethylene glycol (PEG $M_w$<100,000 Da) or alternatively polyethylene oxide (PEO, $M_w$>100,000). In some embodiments, a PEG may have an Mw of about 1000 Da, 5000 Da, 10,000 Da or 20,000 Da.

In other embodiments, the coating material may include a polymer containing carboxylic acid moieties. The carboxylic acid subunit may be an alkyl, alkenyl or aromatic moiety containing subunit. One non-limiting example is polylactic acid (PLA). In other embodiments, the coating material may include a polymer containing phosphate moieties, either at a terminus of the polymer backbone or pendant from the backbone of the polymer. In yet other embodiments, the coating material may include a polymer containing sulfonic acid moieties. The sulfonic acid subunit may be an alkyl, alkenyl or aromatic moiety containing subunit. One non-limiting example is polystyrene sulfonic acid (PSSA) or polyanethole sulfonic acid. In further embodiments, the coating material may include a polymer including amine moieties. The polyamino polymer may include a natural polyamine polymer or a synthetic polyamine polymer. Examples of natural polyamines include spermine, spermidine, and putrescine.

In other embodiments, the coating material may include a polymer containing saccharide moieties. In a non-limiting example, polysaccharides such as xanthan gum or dextran may be suitable to form a material which may reduce or prevent cell sticking in the microfluidic device. For example, a dextran polymer having a size about 3kDa may be used to provide a coating material for a surface within a microfluidic device.

In other embodiments, the coating material may include a polymer containing nucleotide moieties, i.e. a nucleic acid, which may have ribonucleotide moieties or deoxyribonucleotide moieties, providing a polyelectrolyte surface. The nucleic acid may contain only natural nucleotide moieties or may contain unnatural nucleotide moieties which comprise nucleobase, ribose or phosphate moiety analogs such as 7-deazaadenine, pentose, methyl phosphonate or phosphorothioate moieties without limitation.

In yet other embodiments, the coating material may include a polymer containing amino acid moieties. The polymer containing amino acid moieties may include a natural amino acid containing polymer or an unnatural amino acid containing polymer, either of which may include a peptide, a polypeptide or a protein. In one non-limiting example, the protein may be bovine serum albumin (BSA) and/or serum (or a combination of multiple different sera) comprising albumin and/or one or more other similar proteins as coating agents. The serum can be from any convenient source, including but not limited to fetal calf serum, sheep serum, goat serum, horse serum, and the like. In certain embodiments, BSA in a coating solution is present of from about 1 mg/mL to about 100 mg/mL, including 5 mg/mL, 10 mg/mL, 20 mg/mL, 30 mg/mL, 40 mg/mL, 50 mg/mL, 60 mg/mL, 70 mg/mL, 80 mg/mL, 90 mg/mL, or more or anywhere in between. In certain embodiments, serum in a coating solution may be present of from about 20% (v/v) to about 50% v/v, including 25%, 30%, 35%, 40%, 45%, or more or anywhere in between. In some embodiments, BSA may be present as a coating agent in a coating solution at 5 mg/mL, whereas in other embodiments, BSA may be present as a coating agent in a coating solution at 70 mg/mL. In certain embodiments, serum is present as a coating agent in a coating solution at 30%. In some embodiments, an extracellular matrix (ECM) protein may be provided within the coating material for optimized cell adhesion to foster cell growth. A cell matrix protein, which may be included in a coating material, can include, but is not limited to, a collagen, an elastin, an RGD-containing peptide (e.g. a fibronectin), or a laminin. In yet other embodiments, growth factors, cytokines, hormones or other cell signaling species may be provided within the coating material of the microfluidic device.

In some embodiments, the coating material may include a polymer containing more than one of alkylene oxide moieties, carboxylic acid moieties, sulfonic acid moieties, phosphate moieties, saccharide moieties, nucleotide moieties, or amino acid moieties. In other embodiments, the polymer conditioned surface may include a mixture of more than one polymer each having alkylene oxide moieties, carboxylic acid moieties, sulfonic acid moieties, phosphate moieties, saccharide moieties, nucleotide moieties, and/or amino acid moieties, which may be independently or simultaneously incorporated into the coating material.

Covalently linked coating materials. In some embodiments, the at least one inner surface includes covalently linked molecules that provide a layer of organic and/or hydrophilic molecules suitable for maintenance/expansion of biological micro-object(s) within the microfluidic device, providing a conditioned surface for such cells.

The covalently linked molecules include a linking group, wherein the linking group is covalently linked to one or more surfaces of the microfluidic device, as described below. The linking group is also covalently linked to a moiety configured to provide a layer of organic and/or hydrophilic molecules suitable for maintenance/expansion of biological micro-object(s).

In some embodiments, the covalently linked moiety configured to provide a layer of organic and/or hydrophilic molecules suitable for maintenance/expansion of biological micro-object(s) may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids.

In various embodiments, the covalently linked moiety configured to provide a layer of organic and/or hydrophilic molecules suitable for maintenance/expansion of biological micro-object(s) in the microfluidic device may include non-polymeric moieties such as an alkyl moiety, a substituted alkyl moiety, such as a fluoroalkyl moiety (including but not limited to a perfluoroalkyl moiety), amino acid moiety, alcohol moiety, amino moiety, carboxylic acid moiety, phosphonic acid moiety, sulfonic acid moiety, sulfamic acid moiety, or saccharide moiety. Alternatively, the covalently linked moiety may include polymeric moieties, which may be any of the moieties described above.

In some embodiments, the covalently linked alkyl moiety may include carbon atoms forming a linear chain (e.g., a linear chain of at least 10 carbons, or at least 14, 16, 18, 20, 22, or more carbons) and may be an unbranched alkyl moiety. In some embodiments, the alkyl group may include a substituted alkyl group (e.g., some of the carbons in the alkyl group can be fluorinated or perfluorinated). In some embodiments, the alkyl group may include a first segment, which may include a perfluoroalkyl group, joined to a second segment, which may include a non-substituted alkyl group, where the first and second segments may be joined directly or indirectly (e.g., by means of an ether linkage). The first segment of the alkyl group may be located distal to the linking group, and the second segment of the alkyl group may be located proximal to the linking group.

In other embodiments, the covalently linked moiety may include at least one amino acid, which may include more than one type of amino acid. Thus, the covalently linked moiety may include a peptide or a protein. In some embodiments, the covalently linked moiety may include an amino acid which may provide a zwitterionic surface to support cell growth, viability, portability, or any combination thereof.

In other embodiments, the covalently linked moiety may include at least one alkylene oxide moiety, and may include any alkylene oxide polymer as described above. One useful class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da.

The covalently linked moiety may include one or more saccharides. The covalently linked saccharides may be mono-, di-, or polysaccharides. The covalently linked saccharides may be modified to introduce a reactive pairing moiety which permits coupling or elaboration for attachment to the surface. Exemplary reactive pairing moieties may include aldehyde, alkyne or halo moieties. A polysaccharide may be modified in a random fashion, wherein each of the saccharide monomers may be modified or only a portion of the saccharide monomers within the polysaccharide are modified to provide a reactive pairing moiety that may be coupled directly or indirectly to a surface. One exemplar may include a dextran polysaccharide, which may be coupled indirectly to a surface via an unbranched linker.

The covalently linked moiety may include one or more amino groups. The amino group may be a substituted amine moiety, guanidine moiety, nitrogen-containing heterocyclic moiety or heteroaryl moiety. The amino containing moieties may have structures permitting pH modification of the environment within the microfluidic device, and optionally, within the sequestration pens and/or flow regions (e.g., channels).

The coating material providing a conditioned surface may comprise only one kind of covalently linked moiety or may include more than one different kind of covalently linked moiety. For example, the fluoroalkyl conditioned surfaces (including perfluoroalkyl) may have a plurality of covalently linked moieties which are all the same, e.g., having the same linking group and covalent attachment to the surface, the same overall length, and the same number of fluoromethylene units comprising the fluoroalkyl moiety. Alternatively, the coating material may have more than one kind of covalently linked moiety attached to the surface. For example, the coating material may include molecules having covalently linked alkyl or fluoroalkyl moieties having a specified number of methylene or fluoromethylene units and may further include a further set of molecules having charged moieties covalently attached to an alkyl or fluoroalkyl chain having a greater number of methylene or fluoromethylene units, which may provide capacity to present bulkier moieties at the coated surface. In this instance, the first set of molecules having different, less sterically demanding termini and fewer backbone atoms can help to functionalize the entire substrate surface and thereby prevent undesired adhesion or contact with the silicon/silicon oxide, hafnium oxide or alumina making up the substrate itself. In another example, the covalently linked moieties may provide a zwitterionic surface presenting alternating charges in a random fashion on the surface.

Conditioned surface properties. Aside from the composition of the conditioned surface, other factors such as physical thickness of the hydrophobic material can impact DEP force. Various factors can alter the physical thickness of the conditioned surface, such as the manner in which the conditioned surface is formed on the substrate (e.g. vapor deposition, liquid phase deposition, spin coating, flooding, and electrostatic coating). In some embodiments, the conditioned surface has a thickness in the range of about 1 nm to about 10 nm; about 1 nm to about 7 nm; about 1 nm to about 5 nm; or any individual value therebetween. In other embodiments, the conditioned surface formed by the covalently linked moieties may have a thickness of about 10 nm to about 50 nm. In various embodiments, the conditioned surface prepared as described herein has a thickness of less than 10 nm. In some embodiments, the covalently linked moieties of the conditioned surface may form a monolayer when covalently linked to the surface of the microfluidic device (e.g., a DEP configured substrate surface) and may have a thickness of less than 10 nm (e.g., less than 5 nm, or about 1.5 to 3.0 nm). These values are in contrast to that of a surface prepared by spin coating, for example, which may typically have a thickness in the range of about 30 nm. In some embodiments, the conditioned surface does not require a perfectly formed monolayer to be suitably functional for operation within a DEP-configured microfluidic device.

In various embodiments, the coating material providing a conditioned surface of the microfluidic device may provide desirable electrical properties. Without intending to be limited by theory, one factor that impacts robustness of a surface coated with a particular coating material is intrinsic charge trapping. Different coating materials may trap electrons, which can lead to breakdown of the coating material. Defects in the coating material may increase charge trapping and lead to further breakdown of the coating material. Similarly, different coating materials have different dielectric strengths (i.e. the minimum applied electric field that results in dielectric breakdown), which may impact charge trapping. In certain embodiments, the coating material can have an overall structure (e.g., a densely-packed monolayer structure) that reduces or limits that amount of charge trapping.

In addition to its electrical properties, the conditioned surface may also have properties that are beneficial in use with biological molecules. For example, a conditioned surface that contains fluorinated (or perfluorinated) carbon chains may provide a benefit relative to alkyl-terminated chains in reducing the amount of surface fouling. Surface fouling, as used herein, refers to the amount of indiscriminate material deposition on the surface of the microfluidic device, which may include permanent or semi-permanent deposition of biomaterials such as protein and its degradation products, nucleic acids and respective degradation products and the like.

Unitary or Multi-part conditioned surface. The covalently linked coating material may be formed by reaction of a molecule which already contains the moiety configured to provide a layer of organic and/or hydrophilic molecules suitable for maintenance/expansion of biological micro-object(s) in the microfluidic device, as is described below. Alternatively, the covalently linked coating material may be formed in a two-part sequence by coupling the moiety configured to provide a layer of organic and/or hydrophilic molecules suitable for maintenance/expansion of biological micro-object(s) to a surface modifying ligand that itself has been covalently linked to the surface.

Methods of preparing a covalently linked coating material. In some embodiments, a coating material that is covalently linked to the surface of a microfluidic device (e.g., including at least one surface of the sequestration pens and/or flow regions) has a structure of Formula 1 or Formula 2. When the coating material is introduced to the surface in one step, it has a structure of Formula 1, while when the coating material is introduced in a multiple step process, it has a structure of Formula 2.

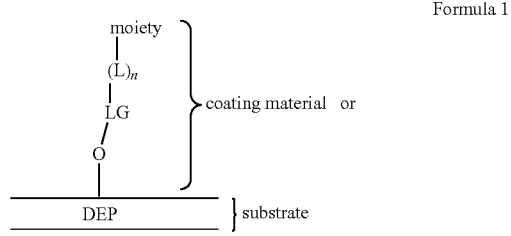

Formula 1

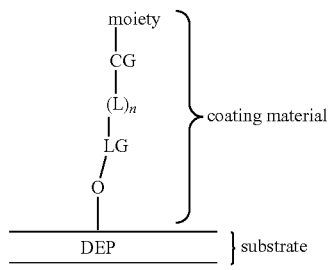

Formula 2

The coating material may be linked covalently to oxides of the surface of a DEP-configured or EW-configured substrate. The DEP- or EW-configured substrate may comprise silicon, silicon oxide, alumina, or hafnium oxide. Oxides may be present as part of the native chemical structure of the substrate or may be introduced as discussed below.

The coating material may be attached to the oxides via a linking group ("LG"), which may be a siloxy or phosphonate ester group formed from the reaction of a siloxane or phosphonic acid group with the oxides. The moiety configured to provide a layer of organic and/or hydrophilic molecules suitable for maintenance/expansion of biological micro-object(s) in the microfluidic device can be any of the moieties described herein. The linking group LG may be directly or indirectly connected to the moiety configured to provide a layer of organic and/or hydrophilic molecules suitable for maintenance/expansion of biological micro-object(s) in the microfluidic device. When the linking group LG is directly connected to the moiety, optional linker ("L") is not present and n is 0. When the linking group LG is indirectly connected to the moiety, linker L is present and n is 1. The linker L may have a linear portion where a backbone of the linear portion may include 1 to 200 non-hydrogen atoms selected from any combination of silicon, carbon, nitrogen, oxygen, sulfur and phosphorus atoms, subject to chemical bonding limitations as is known in the art. It may be interrupted with any combination of one or more moieties chosen from ether, amino, carbonyl, amido, or phosphonate groups, arylene, heteroarylene, or heterocyclic groups. In some embodiments, the backbone of the linker L may include 10 to 20 atoms. In other embodiments, the backbone of the linker L may include about 5 atoms to about 200 atoms; about 10 atoms to about 80 atoms; about 10 atoms to about 50 atoms; or about 10 atoms to about 40 atoms. In some embodiments, the backbone atoms are all carbon atoms.

In some embodiments, the moiety configured to provide a layer of organic and/or hydrophilic molecules suitable for maintenance/expansion of biological micro-object(s) may be added to the surface of the substrate in a multi-step process, and has a structure of Formula 2, as shown above. The moiety may be any of the moieties described above.

In some embodiments, the coupling group CG represents the resultant group from reaction of a reactive moiety $R_x$ and a reactive pairing moiety $R_{px}$ (i.e., a moiety configured to react with the reactive moiety $R_x$). For example, one typical coupling group CG may include a carboxamidyl group, which is the result of the reaction of an amino group with a derivative of a carboxylic acid, such as an activated ester, an acid chloride or the like. Other CG may include a triazolylene group, a carboxamidyl, thioamidyl, an oxime, a mercaptyl, a disulfide, an ether, or alkenyl group, or any other suitable group that may be formed upon reaction of a reactive moiety with its respective reactive pairing moiety. The coupling group CG may be located at the second end (i.e., the end proximal to the moiety configured to provide a layer of organic and/or hydrophilic molecules suitable for maintenance/expansion of biological micro-object(s) in the microfluidic device) of linker L, which may include any combination of elements as described above. In some other embodiments, the coupling group CG may interrupt the backbone of the linker L. When the coupling group CG is triazolylene, it may be the product resulting from a Click coupling reaction and may be further substituted (e.g., a dibenzocylcooctenyl fused triazolylene group).

In some embodiments, the coating material (or surface modifying ligand) is deposited on the inner surfaces of the microfluidic device using chemical vapor deposition. The vapor deposition process can be optionally improved, for example, by pre-cleaning the cover 110, the microfluidic circuit material 116, and/or the substrate (e.g., the inner surface 208 of the electrode activation substrate 206 of a DEP-configured substrate, or a dielectric layer of the support structure 104 of an EW-configured substrate), by exposure to a solvent bath, sonication or a combination thereof. Alternatively, or in addition, such pre-cleaning can include treating the cover 110, the microfluidic circuit material 116, and/or the substrate in an oxygen plasma cleaner, which can remove various impurities, while at the same time introducing an oxidized surface (e.g. oxides at the surface, which may be covalently modified as described herein). Alternatively, liquid-phase treatments, such as a mixture of hydrochloric acid and hydrogen peroxide or a mixture of sulfuric acid and hydrogen peroxide (e.g., piranha solution, which may have a ratio of sulfuric acid to hydrogen peroxide from about 3:1 to about 7:1) may be used in place of an oxygen plasma cleaner.

In some embodiments, vapor deposition is used to coat the inner surfaces of the microfluidic device 200 after the microfluidic device 200 has been assembled to form an enclosure 102 defining a microfluidic circuit 120. Without intending to be limited by theory, depositing such a coating material on a fully-assembled microfluidic circuit 120 may be beneficial in preventing delamination caused by a weakened bond between the microfluidic circuit material 116 and the electrode activation substrate 206 dielectric layer and/or the cover 110. In embodiments where a two-step process is employed the surface modifying ligand may be introduced via vapor deposition as described above, with subsequent introduction of the moiety configured provide a layer of organic and/or hydrophilic molecules suitable for maintenance/expansion of biological micro-object(s). The subsequent reaction may be performed by exposing the surface modified microfluidic device to a suitable coupling reagent in solution.

Figure 2H:
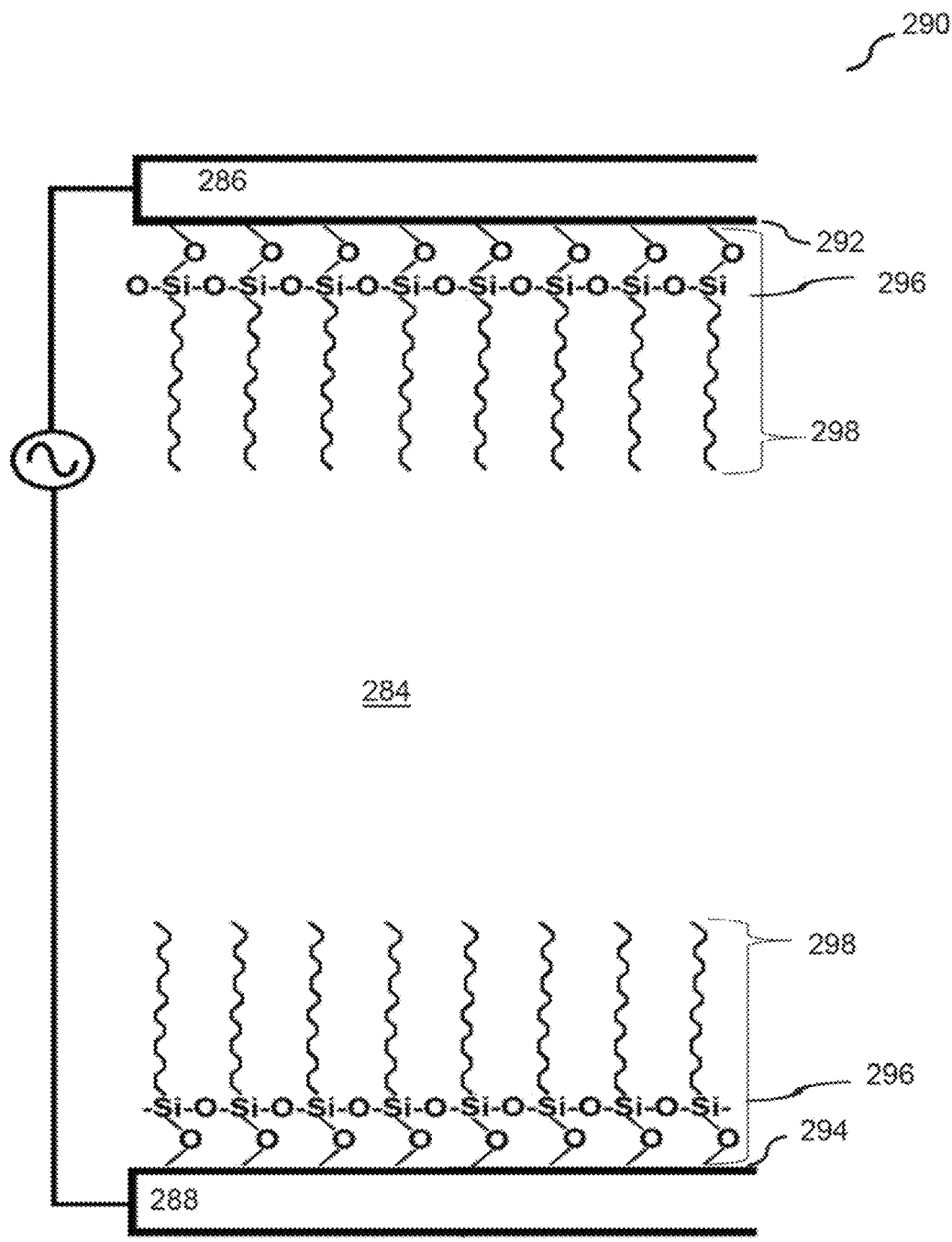
FIG. 2H illustrates a coated surface of the microfluidic device according to an embodiment of the disclosure.

FIG. 2H depicts a cross-sectional view of a microfluidic device 290 having an exemplary covalently linked coating material providing a conditioned surface. As illustrated, the coating materials 298 (shown schematically) can comprise a monolayer of densely-packed molecules covalently bound to both the inner surface 294 of a base 286, which may be a DEP substrate, and the inner surface 292 of a cover 288 of the microfluidic device 290. The coating material 298 can be disposed on substantially all inner surfaces 294, 292 proximal to, and facing inwards towards, the enclosure 284 of the microfluidic device 290, including, in some embodiments and as discussed above, the surfaces of microfluidic circuit material (not shown) used to define circuit elements and/or structures within the microfluidic device 290. In alternate embodiments, the coating material 298 can be disposed on only one or some of the inner surfaces of the microfluidic device 290.

In the embodiment shown in FIG. 2H, the coating material 298 can include a monolayer of organosiloxane molecules, each molecule covalently bonded to the inner surfaces 292, 294 of the microfluidic device 290 via a siloxy linker 296. Any of the above-discussed coating materials 298 can be used (e.g. an alkyl-terminated, a fluoroalkyl terminated moiety, a PEG-terminated moiety, a dextran terminated moiety, or a terminal moiety containing positive or negative charges for the organosiloxy moieties), where the terminal moiety is disposed at its enclosure-facing terminus (i.e. the portion of the monolayer of the coating material 298 that is not bound to the inner surfaces 292, 294 and is proximal to the enclosure 284).

In other embodiments, the coating material 298 used to coat the inner surface(s) 292, 294 of the microfluidic device 290 can include anionic, cationic, or zwitterionic moieties, or any combination thereof. Without intending to be limited by theory, by presenting cationic moieties, anionic moieties, and/or zwitterionic moieties at the inner surfaces of the enclosure 284 of the microfluidic circuit 120, the coating material 298 can form strong hydrogen bonds with water molecules such that the resulting water of hydration acts as a layer (or "shield") that separates the biological micro-objects from interactions with non-biological molecules (e.g., the silicon and/or silicon oxide of the substrate). In addition, in embodiments in which the coating material 298 is used in conjunction with coating agents, the anions, cations, and/or zwitterions of the coating material 298 can form ionic bonds with the charged portions of non-covalent coating agents (e.g. proteins in solution) that are present in a medium 180 (e.g. a coating solution) in the enclosure 284.

In still other embodiments, the coating material may comprise or be chemically modified to present a hydrophilic coating agent at its enclosure-facing terminus. In some embodiments, the coating material may include an alkylene ether containing polymer, such as PEG. In some embodiments, the coating material may include a polysaccharide, such as dextran. Like the charged moieties discussed above (e.g., anionic, cationic, and zwitterionic moieties), the hydrophilic coating agent can form strong hydrogen bonds with water molecules such that the resulting water of hydration acts as a layer (or "shield") that separates the biological micro-objects from interactions with non-biological molecules (e.g., the silicon and/or silicon oxide of the substrate).

Further details of appropriate coating treatments and modifications may be found at U.S. application Ser. No. 15/135,707, filed on Apr. 22, 2016, and is incorporated by reference in its entirety.

Additional system components for maintenance of viability of cells within the sequestration pens of the microfluidic device. In order to promote growth and/or expansion of cell populations, environmental conditions conducive to maintaining functional cells may be provided by additional components of the system. For example, such additional components can provide nutrients, cell growth signaling species, pH modulation, gas exchange, temperature control, and removal of waste products from cells.

EXPERIMENTAL

Example 1

Comparison Between Nucleic Acid Isolation Protocols With or Without the Use of a Nucleic Acid Stabilization Reagent Materials. Emetine (Sigma, catalog No. E2375); Cycloheximide (Sigma, catalog No. C7698); triptolide (Sigma, catalog No. T3652); and sodium azide (Sigma, catalog No. 52002) were all commercially supplied. Lysis reagent was TCL Lysis Buffer (Qiagen, catalog No. 070498). RNA isolation was performed using Agencourt® RNAClean® XP beads (Beckman Coulter, catalog No. A63987). RNA sequencing was performed using Nextera® XT kit (Illumina®, catalog No. FC-131-1024) and Nextera® XT Index kit (Illumina®, catalog No. FC-131-1001).

Biological cells. OKT3 cells, a murine myeloma hybridoma cell line, were obtained from the ATCC (ATCC® Cat. #CRL.-8001™) culture, the cells behave as a suspension cell line. Cultures were maintained by seeding about $2 \times 10^4$ to about $5 \times 10^5$ viable cells/mL and incubating at 37° C., in 20 ml Iscove's Modified Dulbecco's Medium (IMDM) with 20% Fetal Bovine Serum (FBS) and 1% penicillin-streptomycin, using 5% carbon dioxide gaseous environment. Cells were split every 2-3 days. OKT3 cell number and viability were counted and cell density was adjusted to $5 \times 10^5$/ml for loading the cells onto the microfluidic device.

Stock solutions were made as shown in Table 1.

TABLE 1

Stock solutions of stabilization reagent components.

| Component | Concentration and solvent |
|---|---|
| Emetine | 180 mM in DMSO |
| Cycloheximide | 360 mM in DMSO |
| Triptolide | 6 mM in DMSO |
| Sodium azide | 1.6M in water |

A 100× master mix of the stabilization reagent was made as shown in Table 2. The master mix was stored in 30 microliter aliquots at −80° C.

TABLE 2

Master mix composition for stabilization reagent.

| Component | Concentration in master mix | Final concentration as used in 1X stabilizing reaction |
|---|---|---|
| Cycloheximide | 36 mM | 0.36 mM |
| Emetine | 18 mM | 0.18 mM |
| Triptolide | 300 micromolar | 3 micromolar |
| Sodium azide | 310 mM | 3.10 mM |

A single aliquot of OKT3 cells was obtained at approximately $0.5 \times 10^5$ concentration. 50 microliters of cell culture (in Iscove's Modified Dulbecco's Medium (IMDM) with 20% Fetal Bovine Serum (FBS) and 1% penicillin-streptomycin) were aliquoted in triplicate for each of the five conditions tested.

TABLE 3

Conditions tested.

| Condition | | Protocol |
|---|---|---|
| 1. Stabilized nucleic acid sample (In) | a. | Add 0.5 microliter aliquot of stabilization reagent (100x master mix) to 50 microliters of cell culture; |
| | b. | Mix; |
| | c. | Store mixture at 4° C. for 3 days. |
| 2. Lysis control (LC) | a. | Add 50 microliter aliquot of TCL Lysis Buffer (2X) to 50 microliters of cell culture; |
| | b. | Mix; |
| | c. | Store mixture at −80° C. for 3 days. Note: no stabilization reagent is added to cells prior to lysis. |

TABLE 3-continued

Conditions tested.

| Condition | | Protocol |
|---|---|---|
| 3. Negative control (NA) | a. | Store cells at 4° C. for 3 days. Note: no stabilization reagent is added to cells prior to storage. |
| 4. Stabilized nucleic acid sample in PBS (WIn) | a. | Spin down 50 microliters of cell culture; |
| | b. | Remove supernatant and wash cells in PBS; |
| | c. | Spin down cells, remove supernatant, and resuspend cells in 50 microliters of PBS containing 0.5 microliter aliquot of stabilization reagent (100x master mix) |
| | d. | Store suspension at 4° C. for 3 days. |
| 5. Negative control in PBS (W) | a. | Spin down 50 microliters of cell culture; |
| | b. | Remove supernatant and wash cells in PBS; |
| | c. | Spin down cells, remove supernatant, and resuspend cells in 50 microliters of PBS; |
| | d. | Store suspension at 4° C. for 3 days. |
| | e. | Note: no stabilization reagent is added to cells prior to storage. |

Each tube of each replicate was mixed by pipetting up and down. Samples were placed on ice for 15 minutes and then moved to a 4° C. lab refrigerator. Lysis control samples were stored at −80° C., not at 4° C.

Post storage processing of stored samples. After 3 days of storage, samples were processed. For each cell sample stored at 4° C., the sample was washed 2× with PBS containing 3.2 mM sodium azide. Briefly, cells were pelleted by centrifugation at 0.3 g for 2 min.; the supernatant was removed; and the cell pellet was resuspended in 500 microliters PBS containing 3.2 mM sodium azide. This was repeated. After a third centrifugation, cells in each sample were resuspended in 50 microliters PBS containing 3.2 mM sodium azide.

RNA isolation and subsequent sequencing analysis. Two microliters of cell suspension of all stored samples (each of the In, NA, WIn, and W samples) were individually added to 8 microliters of 1.25× TCL Lysis Buffer and pipetted up and down. For each of the Lysis Control (LC) samples, 4 microliters of Cell/TCL Lysis Buffer mix were added to 6 microliters 1× TCL Lysis Buffer and pipetted up and down.

For each sample, RNA was purified using Agencourt® RNAClean® XP beads. Isolated RNA was amplified for 12 cycles using SMART-Seq2 protocol as described in Picelli et al., Nature Methods, 10, 1096-1098 (2013). RNAseq cDNA sequencing libraries were generated using a Nextera® XT kit and barcodes (Nextera XT Index kit). Sequencing was performed on an Illumina® MiSeq, resulting in 3-5million 2×75bp reads per sample.

Figure 4:
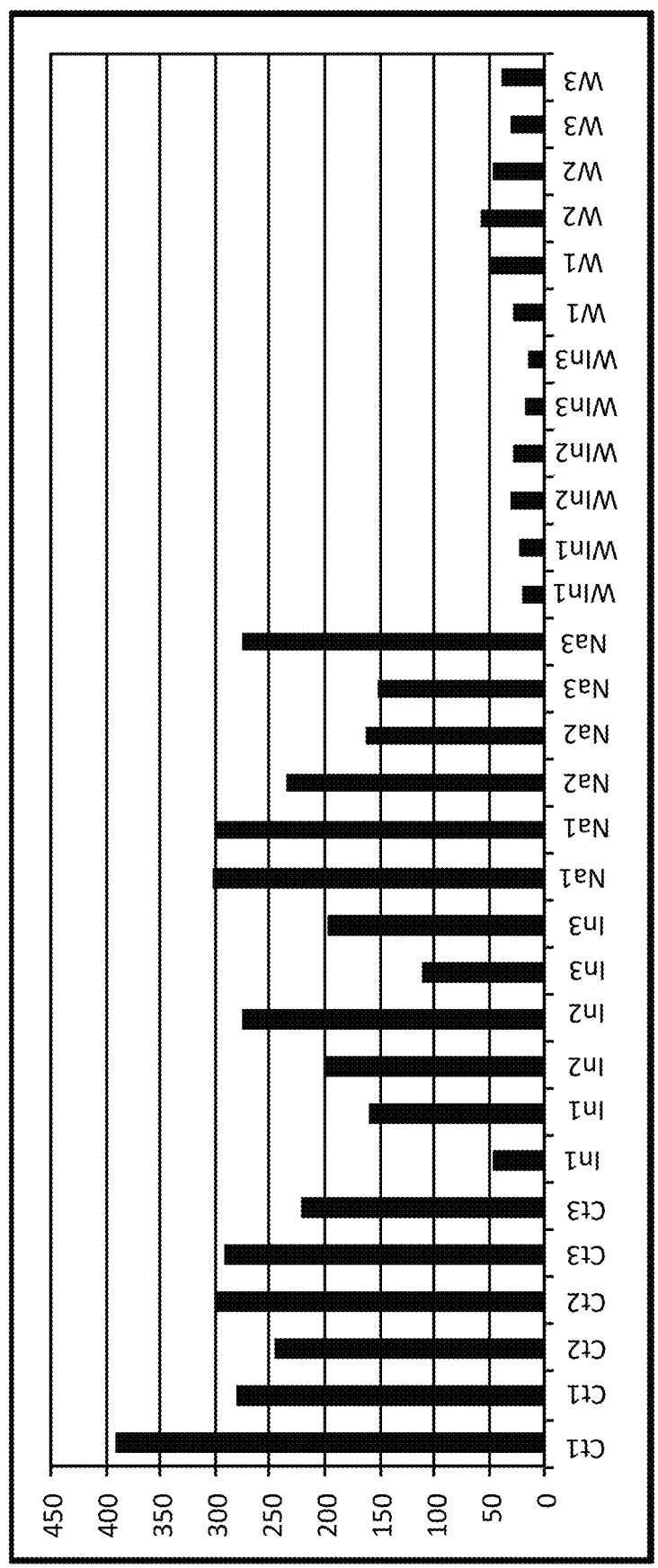
FIG. 4 is a graphical representation of the amount of RNA and DNA recovered from each replicate of five storage preparation methods of Example 1.

Comparison of the amount of cDNA recovered after amplification is shown in FIG. 4. cDNA quantification was measured using fluorometry (Qubit™ fluorometer, ThermoFisher Scientific); amounts shown are total nanograms of recovered cDNA. The first two columns, labeled Ct1, represented technical duplicates of the cDNA amplification reaction using the Lysis Control (LC) sample 1 (Ct1). The remainder of the columns represent, pairwise from left to right: two additional Lysis Control (LC) samples (Ct2 and Ct3); three Inhibited (In) samples treated with the stabilization reagent (In1, In2, In3); three Negative Control (NA) samples (NA1, NA2, NA3); three PBS-Washed samples (WIn) treated with the stabilization reagent (WIn1, WIn2, WIn3); and three PBS-washed samples (W) with no further additions (W1, W2, W3). Each pair of columns (technical duplicates) represents the amount of cDNA recovered under each of that replicate's specific conditions. It can be seen that washing cells into PBS buffer, with (WIn column pairs) or without (W column pairs) addition of the stabilization reagent resulted in very low yields of nucleic acids overall, compared to the recovery of cDNA for the LC, In and NA samples. While the amounts of cDNA recovered from the Ct and NA samples were similar in yield, the quality of the isolated RNA from samples treated with the stabilization reagent was more suitable for library preparation, as discussed below.

Figure 5A:
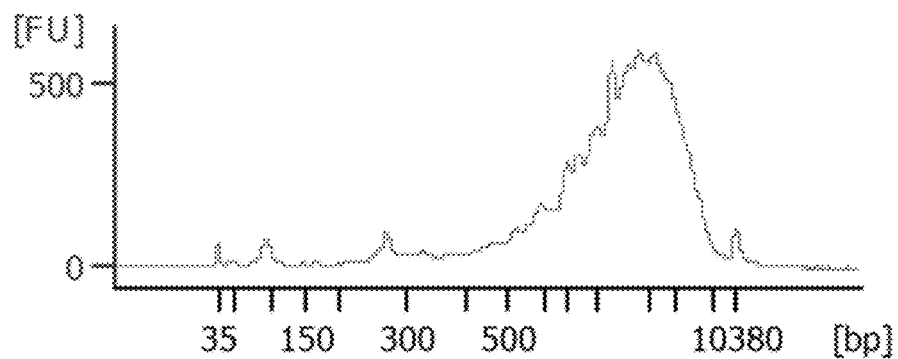
FIG. 5A is a graphical representation of the size distribution of cDNA recovered from the cells treated as the Lysis Control (LC) in Example 1.
Figure 5B:
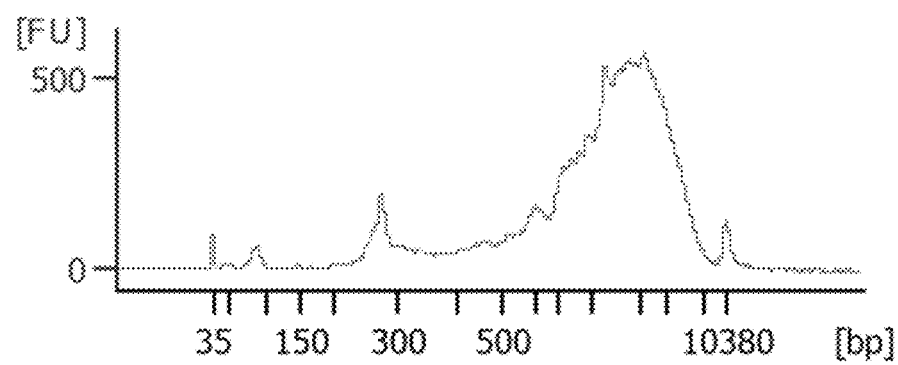
FIG. 5B is a graphical representation of size distribution of cDNA recovered from the cells treated with an embodiment of the stabilization reagent of the disclosure (In) in Example 1.
Figure 5C:
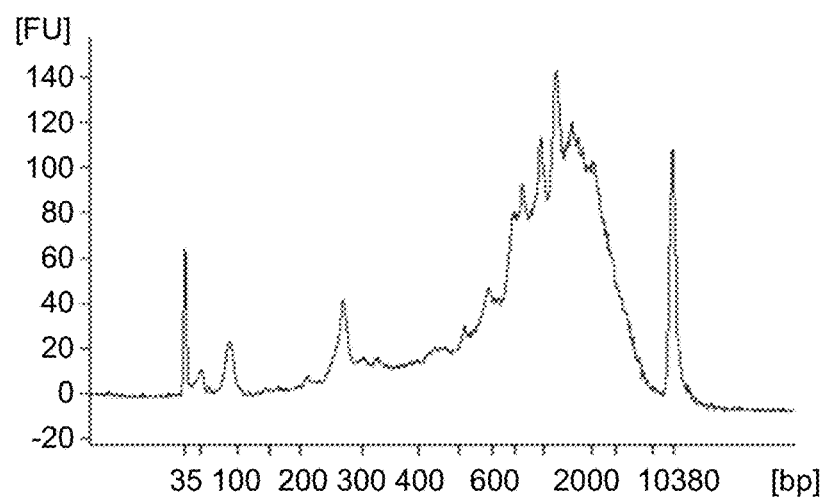
FIG. 5C is a graphical representation of size distribution of cDNA recovered from the cells that were not treated with an embodiment of the stabilization reagent of the disclosure (NA) in Example 1.

The size distributions of the cDNA recovered from a Lysis Control sample (LC), lysed with no stabilization reagent present on day 1 and stored at −80° C. (FIG. 5A), and an Inhibited sample (In), treated with the stabilization reagent and stored for 72 hours at 4° C. and then lysed (FIG. 5B), are shown in FIG. 5. The curves look very similar, showing no significant differences between the size distribution of cDNA of the Inhibited sample (In) as compared to that of the Lysis Control sample (LC). The Bioanalyzer traces for each set of samples show good correlation and relative distribution for entry into sequencing. FIG. 5C shows the distribution of size of the cDNA recovered from a NA sample. Compared to the traces shown in FIGS. 5A and 5B, additional low molecular weight material was evident along the lower molecular weight side of the main distribution peak of the trace. The lower molecular weight cDNA shown in the Bioanalyzer trace indicated that the RNA recovered in the NA sample suffered from increased degradation relative to the LC and In samples. Thus, despite the abundant quantity of cDNA observed (FIG. 4), the NA samples did not provide cDNA libraries optimized for sequencing.

Analysis of the sequencing data was performed using TopHat alignment and Cufflinks DE expression modules, made available through Illumina BaseSpace. Differential Expression (DE) analysis is shown in FIG. 6 for Inhibited samples treated with the stabilization reagent (In1, In2, In3) with the Lysis Control samples (Ct1, Ct2, Ct3) used as reference. DE analysis showed 140 genes in the In samples exhibited altered expression levels ranging from 3.4× to 1.2×. Thirty-eight genes decreased in expression as assessed using a 1.5× cutoff (data not shown). The largest decrease was a 2.09× decrease. Gene ontology analysis did not predict a specific pathway enrichment in the genes that decreased in expression. Eighteen genes increased in expression as assessed using a 1.5× cutoff. The largest increase was 3.4× for Histone protein. Gene ontology analysis predicted one specific enrichment, the amine secretion pathway (2 genes). Overall, the changes appeared to be random and minor. Accordingly, little effect is predicted for profiling experiments of cells having been stabilized before storage at 4° C. (In) compared to direct lysis and storage at −80° C. (LC).

DE analysis is shown in FIG. 7 for Negative Control cells stored at 4° C. with no stabilization (NA1, NA2, NA3), with the Lysis Control cells (Ct1, Ct2, Ct3) used as reference. Three hundred and three genes were differentially expressed, ranging from 8.2× to 1.2× changes. One hundred thirty-nine genes decreased in expression as assessed using a 1.5× cutoff (data not shown). The largest decrease was 8.2×, and gene ontology analysis predicted pathway enrichment for cellular protein modifications (GO:0006464) (28 genes) and for metabolic process (GO:0008152), 66 genes. Eighteen genes increased in expression as assessed using a 1.5× cutoff (data not shown). The largest increase was 5.4×. Gene ontology analysis did not predict any specific pathway enrichment. The genes that were upregulated in the In samples treated with the stabilization agent overlap with the genes upregulated in the NA cells having no stabilization reagent added, which indicated that nothing in the stabilization method itself triggered the increases in expression, but appeared to be due to environmental exposure and/or handling.

DE analysis is shown in FIG. 8 for WIn cells washed with PBS, wherein the stabilization reagent was added afterward, and stored at 4° C. (WIn1, WIn2, WIn3), with the Lysis Control cells used as reference. A large number of genes, 1160, decreased in expression, as assessed using a 1.5× cutoff (data not shown). The largest decrease was 8.2×. Gene ontology analysis predicted enrichment in greater than ten specific pathways. Likewise, a large number of genes, 1108, were increased in expression as assessed using a 1.5× cutoff, with the largest increase being 8.4× (data not shown). Gene ontology analysis predicted enrichment in greater than ten specific pathways. Two specific genes Samd11 and Samd1 were the most highly activated at 8.4× and 7.9× respectively. These two putative transcription factors could have driven the large number of gene expression changes observed.

DE analysis is shown in FIG. 9 for W cells washed with PBS and having no stabilization reagent added (W1, W2. W3), with the Lysis Control samples (Ct1, Ct2, Ct3) used as reference. A large number of genes, 744, decreased in expression, as assessed using a 1.5× cutoff (data not shown). The largest decrease was 13×. Gene ontology analysis predicted enrichment in greater than ten specific pathways. Likewise, a large number of genes, 774, were increased in expression as assessed using a 1.5× cutoff, with the largest increase being 5.1× (data not shown). Gene ontology analysis predicted enrichment in greater than ten specific pathways. Samd11 is again one of the most highly activated genes, having a 4.6× enrichment. This transcription factor is poorly characterized and may be driving a large number of the gene expression changes seen.

The results show that the effect of storing cells in media at 4° C. does not trigger major changes, although metabolic gene expression showed a significant decrease. However, metabolic gene expression changes are blocked by use of the stabilization reagent (more than 60 genes are affected). The stabilization reagent should be added to cells before washing with media such as PBS.

Example 2

Isolation of Stabilized Nucleic Acids Within a Microfluidic Device After Storage System and device: An OptoSelect™ chip, a nanofluidic device manufactured by Berkeley Lights, Inc. and controlled by an optical instrument which was also manufactured by Berkeley Lights, Inc. were employed. The instrument includes: a mounting stage for the chip coupled to a temperature controller; a pump and fluid medium conditioning component; and an optical train including a camera and a structured light source suitable for activating phototransistors within the chip. The OptoSelect chip includes a substrate configured with OptoElectroPositioning (OEP™) technology, which provides a phototransistor-activated OET force. The chip also included a plurality of microfluidic channels, each having a plurality of NanoPen™ chambers (or sequestration pens) fluidically connected thereto. The volume of each sequestration pen is around $1 \times 10^6$ cubic microns.

Cells and culture medium: as above for Example 1.

Microfluidic device priming. 250 microliters of 100% carbon dioxide is flowed in at a rate of 12 microliters/sec, followed by 250 microliters of PBS containing 0.1%

Pluronic® F27 (Life Technologies® Cat#P6866) flowed in at 12 microliters/sec, and finally 250 microliters of PBS flowed in at 12 microliters/sec. Introduction of the culture medium follows.

Media perfusion. Medium is perfused through the microfluidic device according to either of the following two methods:

1. Perfuse at 0.01 microliters/sec for 2 h; perfuse at 2 microliters/sec for 64 sec; and repeat.
2. Perfuse at 0.02 microliters/sec for 100 sec; stop flow 500 sec; perfuse at 2 microliters/sec for 64 sec; and repeat.

Cells are introduced into two OptoSelect devices at the density as described in Example 1, individually placed into NanoPen chambers and cultured at 37° C. for 24 h.

Half of the cultured cells are exported from each of devices 1 and 2 using optically actuated dielectrophoretic forces generated by the OEP technology. These Control samples of OKT3 cells are exported into TCL Lysis Buffer (2×), mixed, and frozen at −80° C.

The cells remaining within the OptoSelect device 1 are stabilized for storage by flowing 50 microliters of the stabilization reagent (2×, diluted from the 100× master mix of Table 2, 0.72 mM cycloheximide, 0.36 mM emetine, 6 micromolar triptolide, 6.20 mM sodium azide), into the microfluidic channel at a rate of 1 microliter/sec, displacing the culture medium. The stabilization reagent is permitted to diffuse into the NanoPen chambers for a period of 5 min, and the OKT3 cells are contacted with the stabilization reagent for a further 15 min period before removing the OptoSelect device 1 from the instrument. The OptoSelect device 1 containing the stabilized cells (Stabilized) is sealed to prevent evaporation and stored at 4° C. overnight.

The cells remaining within OptoSelect device 2 are moved to 4° C. for storage without the addition of stabilization reagent. The OptoSelect device 2 containing the non-stabilized cells (Non-Stabilized) is sealed to prevent evaporation and stored at 4° C. overnight.

The next day, OptoSelect device 1 is returned to the instrument and medium containing stabilization cocktail is flushed through the device to replace the storage medium. The group of stabilized cells is then exported from the OptoSelect device into TCL Lysis Buffer (2×) and processed for library generation, nucleic acid sequencing, and sequence analysis, as described above in Experiment 1. OptoSelect device 2 is also replaced onto the instrument after the same overnight storage period as the OptoSelect device 1, and fresh medium (containing no stabilization reagent) is used to flush and recondition the device. The group of non-stabilized cells (Non-Stabilized) is then exported from the OptoSelect device into TCL Lysis Buffer (2×) and processed for library generation, nucleic acid sequencing, and sequence analysis, as described above in Experiment 1.

Sequencing results from the Stabilized and Control samples are expected to show reduced variability in gene expression between the Stabilized and Control cells, as compared to the variability in gene expression between the Non-Stabilized and Control cells.

Recitation of Embodiments

1. A kit for stabilizing a population of nucleic acids within a biological cell, including: at least one irreversible protein translation inhibitor; at least one ribonucleic acid transcription inhibitor; and at least one electron transport chain agent including an electron transport chain inhibitor and/or an electron transport chain decoupling agent.

2. The kit of embodiment 1, wherein the kit further includes a second protein translation inhibitor.

3. The kit of embodiment 2, wherein the second protein translation inhibitor is a reversible protein translation inhibitor.

4. The kit of any one of embodiments 2-3, wherein the second protein translation inhibitor is fast acting compared to the irreversible protein translation inhibitor.

5. The kit of any one of the embodiments 2-4, wherein the second protein translation inhibitor is cell membrane permeable.

6. The kit of any one of embodiments 2-5, wherein the second protein translation inhibitor is diazooxide, a glutarimide antibiotic, and/or an ipecac alkaloid.

7. The kit of any one of embodiments 2-6, wherein the second protein translation inhibitor is cycloheximide.

8. The kit of any one of the preceding embodiments, wherein the at least one irreversible protein translation inhibitor is cell membrane permeable.

9. The kit of any one of the preceding embodiments, wherein the at least one irreversible protein translation inhibitor is an aminoglycoside antibiotic, D-galactosamine, and/or emetine.

10. The kit of any one of the preceding embodiments, wherein the at least one irreversible protein translation inhibitor is emetine.

11. The kit of any one of the preceding embodiments, wherein the at least one ribonucleic acid transcription inhibitor is cell membrane permeable.

12. The kit of any one of the preceding embodiments, wherein the at least one ribonucleic acid transcription inhibitor is aCDK9 inhibitor, aurethricin, thiolutin, amanitin, and/or triptolide.

13. The kit of any one of the preceding embodiments, wherein the at least one ribonucleic acid transcription inhibitor is an irreversible inhibitor.

14. The kit of any one of the preceding embodiments, wherein the at least one ribonucleic acid transcription inhibitor is triptolide.

15. The kit of any one of the preceding embodiments, wherein the at least one electron transport chain agent has reversible activity.

16. The kit of any one of the preceding embodiments, wherein the at least one electron transport chain agent is cell membrane permeable.

17. The kit of any one of the preceding embodiments, wherein the electron transport chain agent is an electron transport chain inhibitor.

18. The kit of any one of the preceding embodiments wherein the electron transport chain agent is sodium azide.

19. The kit of any one of the preceding embodiments, wherein at least one of the at least one irreversible protein translation inhibitor, the at least one ribonucleic acid transcription inhibitor, and the at least one electron transport chain agent is provided in a solution.

20. The kit of embodiment 19, wherein the at least one irreversible protein translation inhibitor is provided in solution.

21. The kit of embodiment 20, wherein the at least one irreversible protein translation inhibitor is present within the solution at a concentration from 1.0 micromolar to 2 M.

22. The kit of any one of embodiments 1-21, wherein the second protein translation inhibitor is provided in solution.

23. The kit of embodiment 22, wherein the second protein translation inhibitor is present within the solution at a concentration from 1.0 micromolar to 2 M.

24. The kit of any one of embodiments 1-23, wherein the at least one ribonucleic acid transcription inhibitor is provided in solution.

25. The kit of embodiment 24, wherein the at least one ribonucleic acid transcription inhibitor is present within the solution at a concentration from 10 nanomolar to 500 millimolar.

26. The kit of any one of embodiments 1-25, wherein the at least one the electron transport chain agent is provided in solution.

27. The kit of embodiment 26, wherein the at least one electron transport chain agent is present in a concentration from 0.1 micromolar to 1 M.

28. The kit of any one of the preceding embodiments, wherein the kit does not include a RNase inhibitor.

29. The kit of any one of the preceding embodiments, wherein the kit further includes a protease inhibitor.

30. The kit of embodiment 29, wherein the protease inhibitor is a cysteine protease or a serine protease inhibitor.

31. The kit of any one of the preceding embodiments, wherein the stabilized population of nucleic acids comprises a population of ribonucleic acids.

32. The kit of any one of the preceding embodiments, wherein more than one of the at least one irreversible protein translation inhibitor; the at least one ribonucleic acid transcription inhibitor; and the at least one electron transport chain agent are provided in a master mix.

33. The kit of embodiment 32, wherein all three of the at least one irreversible protein translation inhibitor; the at least one ribonucleic acid transcription inhibitor; and the at least one electron transport chain agent are provided in the master mix.

34. The kit of any one of the preceding embodiments, wherein the kit further includes a lysis buffer.

35. The kit of any one of the preceding embodiments, wherein one or more components of the kit is provided in a separate container.

36. The kit of any one of embodiments 1-35, wherein the biological cell is a mammalian cell.

37. The kit of any one of embodiments 1-36, wherein the biological cell is a human cell.

38. The kit of any one of embodiments 1-37, wherein the biological cell is a cancer cell.

39. A method of stabilizing a population of nucleic acids in a biological cell, including the steps of: contacting the biological cell with at least one irreversible protein translation inhibitor; at least one ribonucleic acid transcription inhibitor; and at least one electron transport chain agent comprising an electron transport chain inhibitor and/or an electron transport chain decoupling agent, wherein the contacting is performed for a period of time sufficient to stabilize the population of nucleic acids and thereby convert the biological cell to a stabilized biological cell.

40. The method of embodiment 39, wherein the biological cell is simultaneously contacted with each of the at least one irreversible protein translation inhibitor, at least one ribonucleic acid transcription inhibitor, and at least one electron transport chain agent.

41. The method of embodiment 39 or 40, further including storing the stabilized biological cell in the presence of each of the at least one irreversible protein translation inhibitor, at least one ribonucleic acid transcription inhibitor, and at least one electron transport chain agent.

42. The method of embodiment 41, wherein the step of storing for at least 8 hours.

43. The method of embodiment 41 or 42, wherein the step of storing is performed at a temperature of 0° C. to 4° C.

44. The method of any one of embodiments 39-43, further including: lysing the stabilized biological cell by contacting the stabilized biological cell with a lysis reagent.

45. The method of embodiment 44, further including isolating at least a portion of the stabilized population of nucleic acids released from the lysed stabilized biological cell.

46. The method of embodiment 44 or 45, wherein the step of lysing further includes washing the stabilized biological cell before contacting the stabilized biological cell with the lysis reagent.

47. The method of any one of embodiments 44-46, further including analyzing at least one class of nucleic acid from the at least a portion of the population of nucleic acids released from the stabilized lysed biological cell.

48. The method of embodiment 47, wherein analyzing includes sequencing the at least one class of nucleic acid.

49. The method of embodiment 48, wherein the at least one class of nucleic acid is ribonucleic acid.

50. A method of stabilizing a population of nucleic acids in a biological cell within a microfluidic device including an enclosure, including the steps of: disposing the biological cell within the enclosure of the microfluidic device, wherein the enclosure comprises a flow region and at least one chamber and at least one chamber fluidically connected to the flow region, wherein the flow region and at least one chamber are configured to contain a fluidic medium; and contacting the biological cell with at least one irreversible protein translation inhibitor; at least one ribonucleic acid transcription inhibitor; and at least one electron transport chain agent comprising an electron transport chain inhibitor and/or an electron transport chain decoupling agent, wherein the contacting is performed for a period of time sufficient to stabilize the population of nucleic acids in the biological cell, and thereby convert the biological cell to a stabilized biological cell.

51. The method of embodiment 50, wherein disposing the biological cell within the microfluidic device includes disposing the biological cell within the at least one chamber.

52. The method of embodiment 50 or 51, wherein the at least one chamber includes a sequestration pen having an isolation region; and a connection region fluidically connecting the isolation region to the flow region, wherein the isolation region and the connection region are configured such that components of the medium are exchanged between the flow region and the isolation region of the sequestration pen substantially only by diffusion.

53. The method of embodiment 52, wherein disposing the biological cell within the at least one chamber includes disposing the biological cell within the isolation region of the sequestration pen.

54. The method of embodiment 53, wherein disposing the biological cell within the at least one chamber further includes moving the biological cell using a dielectrophoretic force.

55. The method of embodiment 54, wherein the dielectrophoretic force is optically actuated.

56. The method of any one of embodiments 50-55, further including storing the stabilized biological cell for a period of time.

57. The method of embodiment 56, wherein the step of storing is performed for at least 8 hours.

58. The method of embodiment 56 or 57, wherein the step of storing is performed at a temperature of 0° C. to 4° C.

59. The method of any one of embodiments 50-58, further including a step of exporting the stabilized biological cell out of the microfluidic device.

60. The method of embodiment 59, wherein the step of exporting the stabilized biological cell includes moving the biological cell with a dielectrophoretic force.

61. The method of embodiment 60, wherein the dielectrophoretic force is optically actuated.

62. The method of any one of embodiments 50-61, further including lysing the stabilized biological cell by contacting the stabilized biological cell with a lysis reagent.

63. The method of embodiment 62, further including isolating at least a portion of a stabilized population of nucleic acids released from the lysed stabilized biological cell.

64. The method of embodiment 62 or 63, wherein the step of lysing further includes washing the stabilized biological cell before contacting the stabilized biological cell with the lysis reagent.

65. The method of any one of embodiments 63 or 64, further including analyzing at least one class of nucleic acid from the at least a portion of the stabilized population of nucleic acids released from the lysed stabilized biological cell.

66. The method of embodiment 65, wherein analyzing includes sequencing the at least one class of nucleic acid.

67. The method of embodiment 65 or 66, wherein the at least one class of nucleic acid is ribonucleic acid.

68. The method of any one of embodiments 39-67, wherein the biological cell is a mammalian cell.

69. The method of any one of embodiments 39-68, wherein the biological cell is a human cell.

70. The method of any one of embodiments 39-69, wherein the biological cell is a cancer cell.

71. The method of any one of embodiments 39-70, wherein the biological cell is an immunological cell.

72. The method of embodiment 71, wherein the immunological cell is a T cell, a B cell, a NK cell, or a macrophage.

73. The method of any one of embodiments 50-72, wherein the step of disposing the biological cell within the enclosure including using a dielectrophoretic force to move the biological cell.

74. The method of embodiment 73, wherein the dielectrophoretic force is optically actuated.

75. The method of any one of embodiments 39-74, wherein the step of contacting the biological cell with at least one irreversible protein translation inhibitor; at least one ribonucleic acid transcription inhibitor; and at least one electron transport chain agent comprising an electron transport chain inhibitor and/or an electron transport chain decoupling agent comprises contacting the biological cell with one or more components of the kit of any one of embodiments 1-33.

The foregoing written specification is considered to be sufficient to enable one skilled in the art to practice the embodiments. The foregoing description and Examples detail certain embodiments, describes the best mode contemplated and are exemplary only. It will be appreciated, however, that no matter how detailed the foregoing may appear in text, the embodiment may be practiced in many ways and should be construed in accordance with the appended claims and any equivalents.

What is claimed is:

1. A method of stabilizing a population of ribonucleic acids in a biological cell, wherein the biological cell is an animal cell, comprising:
    contacting the animal cell with at least one irreversible protein translation inhibitor; at least one ribonucleic acid transcription inhibitor; and at least one electron transport chain agent comprising an electron transport chain inhibitor and/or an electron transport chain decoupling agent, wherein the at least one ribonucleic acid transcription inhibitor is a CDK9 inhibitor, aurethricin, thiolutin, amanitin, and/or triptolide; and/or the electron transport chain agent is rotenone, 2-thenoyltrifluoroacetone, carboxin, cyanide, sodium azide, 2,4 dinitrophenol, dicumarol, and/or carbonylcyanide-4-(trifluoromethoxy)-phenylhydrazone; and
    wherein the contacting is performed for a period of time sufficient to retain the size distribution of the population of ribonucleic acids within the animal cell.

2. The method of claim 1, wherein the animal cell is simultaneously contacted with each of the at least one irreversible protein translation inhibitor, at least one ribonucleic acid transcription inhibitor, and at least one electron transport chain agent.

3. The method of claim 1, further comprising storing the stabilized animal cell in the presence of each of the at least one irreversible protein translation inhibitor, at least one ribonucleic acid transcription inhibitor, and at least one electron transport chain agent.

4. The method of claim 3, wherein the step of storing is performed for at least 8 hours and/or at a temperature of 0° C. to 4° C.

5. The method of claim 1, further comprising: lysing the animal cell by contacting the animal cell with a lysis reagent.

6. The method of claim 5, further comprising isolating at least a portion of a population of ribonucleic acids released from the lysed animal cell.

7. The method of claim 6, further comprising analyzing at least one class of ribonucleic acid from the at least a portion of the population of ribonucleic acids released from the lysed animal cell.

8. The method of claim 7, wherein analyzing includes sequencing the at least one class of ribonucleic acid.

9. The method of claim 5, wherein the step of lysing further includes washing the animal cell before contacting the biological animal cell with the lysis reagent.

10. The method of claim 1, wherein the animal cell is a mammalian cell.

11. The method of claim 1, wherein the animal cell is an immunological cell.

12. The method of claim 11, wherein the immunological cell is a T cell, a B cell, a NK cell, or a macrophage.

13. The method of claim 1, wherein more than one of the at least one irreversible protein translation inhibitor; the at least one ribonucleic acid transcription inhibitor;
    and the at least one electron transport chain agent are provided in a master mix.

14. The method of claim 13, wherein all three of the at least one irreversible protein translation inhibitor; the at least one ribonucleic acid transcription inhibitor; and the at least one electron transport chain agent are provided in the master mix.

15. The method of claim 1, wherein the animal cell is a human cell.

16. The method of claim 1, wherein the animal cell is a cancer cell.

17. The method of claim 1, wherein the animal cell is contacted with a second protein translation inhibitor.

18. The method of claim 1, wherein after the contacting, metabolic gene expression changes are disrupted or blocked in the animal cell.

19. The method of claim 1, wherein the at least one irreversible protein translation inhibitor is an aminoglycoside antibiotic, D-galactosamine, and/or emetine.

20. The method of claim 1, wherein the at least one ribonucleic acid transcription inhibitor is a CDK9 inhibitor, aurethricin, thiolutin, amanitin, and/or triptolide; and the electron transport chain agent is rotenone, 2-thenoyltrifluoroacetone, carboxin, cyanide, sodium azide, 2,4 dinitrophenol, dicumarol, and/or carbonylcyanide-4-(trifluoromethoxy)-phenylhydrazone.

21. A method of stabilizing a population of ribonucleic acids in a biological cell, wherein the biological cell is an animal cell, comprising:
  contacting the animal cell with at least one irreversible protein translation inhibitor; at least one ribonucleic acid transcription inhibitor; and at least one electron transport chain agent comprising an electron transport chain inhibitor and/or an electron transport chain decoupling agent, wherein the at least one ribonucleic acid transcription inhibitor is a CDK9 inhibitor, aurethricin, thiolutin, amanitin, and/or triptolide; and/or the electron transport chain agent is rotenone, 2-thenoyltrifluoroacetone, carboxin, cyanide, sodium azide, 2,4 dinitrophenol, dicumarol, and/or carbonylcyanide-4-(trifluoromethoxy)-phenylhydrazone; and
  wherein the contacting is performed for a period of time sufficient to disrupt cellular processes for production and degradation of ribonucleic acids in the population of ribonucleic acids within the animal cell.

\* \* \* \* \*